US007252824B2

(12) United States Patent
Simard et al.

(10) Patent No.: US 7,252,824 B2
(45) Date of Patent: Aug. 7, 2007

(54) ANTI-NEOVASCULATURE PREPARATIONS FOR CANCER

(75) Inventors: John J. L. Simard, Northridge, CA (US); David C. Diamond, West Hills, CA (US)

(73) Assignee: Mannkind Corporation, Valencia, CA (US)

( * ) Notice: Subject to any disclaimer, the term of this patent is extended or adjusted under 35 U.S.C. 154(b) by 708 days.

(21) Appl. No.: 10/094,699

(22) Filed: Mar. 7, 2002

(65) Prior Publication Data

US 2003/0046714 A1 Mar. 6, 2003

Related U.S. Application Data

(60) Provisional application No. 60/274,063, filed on Mar. 7, 2001.

(51) Int. Cl.
*A61K 39/00* (2006.01)

(52) U.S. Cl. ............... 424/184.1; 424/9.1; 424/9.2; 435/69.1; 435/70.1; 435/183; 530/350; 530/380; 530/385; 530/387.1; 530/387.3

(58) Field of Classification Search ............ 530/387.3, 530/350, 380, 385, 387.1, 387.7, 388.1, 388.2, 530/388.4, 384.7; 424/134.1, 135.1, 141.1, 424/9.1, 184.1, 9.2; 435/7.9, 188, 69.1, 70.1, 435/183; 525/54.1

See application file for complete search history.

(56) References Cited

FOREIGN PATENT DOCUMENTS

| WO | WO 99/43801 | 9/1999 |
|---|---|---|
| WO | WO 00/06723 | 2/2000 |
| WO | WO 01/82963 | 11/2001 |

OTHER PUBLICATIONS

Verma et al. (1997) Nature vol. 389, p. 239-242.*
Marshall (1995) Science, vol. 269, p. 1050-1055.*
Eck et al. (Goodman & Gilman's The Pharmacological Basis of Therapeutics (1996), 9th Edition, Chapter 5, McGraw-Hill, NY).*
Ross et al, Human Gene Therapy, 1996, vol. 7, pp. 1781-1790.*
Rubanyi, Mol. Aspects Med. (2001) 22:113-142.*
Juengst British Medical Journal (2003) vol. 326, pp. 1410-1411.*
Ratnov et al (Gene Therapy 2000, 7:1853-1858).*
Borges et al (Current Opinion in Gastroenterology 2002, 18(6): 723-731).*
Shaw and Strong (Frontiers in Bioscience 11, 1189-1198, Jan. 1, 2006).*
Feltquate et al (J Immunology 1997 158:2278-2284).*
Pertmer et al (J. Virology, 1996 70:6119-6125).*
Barry et al (Vaccine 1997 15:788-791).*
Seppa. Science News Online (Aug. 8, 1998): http://www.sciencenews.org/pages/sn_arc98/8_8_98/fob3.htm.*
Drug Discovery and Development (http://www.dddmag.com/Glossary.aspx?RPTID=KWSRCH&SEARCHWORD=vaccine &SEARCHMETHOD=WORD).*
Davidoff et al (Journal of Pediatric Surgery. Jan. 2001. 36:30-36).*
Drabner and Guzman (Biomolecular Engineering. 2001. 17:75-82; Available online Feb. 15, 2001).*
Fomsgaard et al (Vaccine. 1999. 18:681-691).*
Millauer et al. 1994. Nature, 367:576-579.*
Stratmann et al 1997. Anti-angiogenic gene therapy of malignant glioma, S68:105-110.*
Machein et al. 1999. Human Gene Therapy, 10:1117-1128.*
Millauer et al. 1996. Cancer Research, 1996. 56:1615-1620.*
Rockwell and Goldstein (Molecular and Cellular Differentiation. 1995, 3:315-335).*
Siemeister et al (Center and Metastasis Reviews.1998. 17:241-248).*
Prewett et al (Cancer Research. 1999. 59:5209-5218).*
Supplementary Search Report for International Patent Application No. 02715085.3 issued Oct. 5, 2004 by the European Patent Office.
Bellone, et al. "Cancer immunotherapy: synthetic and natural peptides in the balance." *Immunology Today*. 20 (10): 457-462 (1999).
Brekken, et al. "Vascular Endothelial Growth Factor and Vascular Targeting of Solid Tumors." *Anticancer Research*. 21(6B): 4221-4230 (2001).
Dias, et al. "Inhibition of both autocrine and paracrine VEGF/VEGFR-2 angiogenic pathways is essential to induce long term remission of human leukemias xenotransplanted into NOD-SCID mice." Database Biosis Online! (2000) XP002288727 (abstract).
Lorber, et al. "Human Allogeneic Vascular Rejection After Arterial Transplantation and Peripheral Lymphoid Reconstitution in Severe Combined Immunodeficient Mice." *Transplantation*. 67(6): 897-903 (1999).
Marchand, et al. "Blockade of in vivo VEGF-mediated angiogenesis by antisense gene therapy: role of Flk-1 receptors." *Am J Physiol Heart Circ Physiol*. 282:H194-H204 (2002).
Murray, et al. "Human T-cell mediated destruction of allogeneic dermal microvessels in a severe combined immunodeficient mouse." *Proc. Natl. Acad. Sci.* 91(19): 9146-9150 (1994).
Nor, et al. "Engineering and Characterization of Functional Human Microvessels in Immunodeficient Mice." *Laboratory Investigation*. 81(4): 453-463 (2001).
Parast, et al. "Characterization and Kinetic Mechanism of Catalytic Domain of Human Vascular Endothelial Growth Factor Receptor-2 Tyrosine Kinase (VEGFR2 TK), a Key Enzyme in Angiogenesis." *Biochemistry*. 37: 16788-16801 (1998).
Shiroki, et al. "Human Peripheral Blood Leukocyte-Reconstituted Severe Combined Immunodeficient Mouse: Analysis of human immune response against porcine islet transplantation." *Transplantation*. 63(6): 818-823 (1997).

(Continued)

*Primary Examiner*—Larry R. Helms
*Assistant Examiner*—Parithosh K. Tungaturthi
(74) *Attorney, Agent, or Firm*—Sonnenschein Nath & Rosenthal LLP

(57) ABSTRACT

Disclosed herein are immunogenic compositions, methods of designing immunogenic compositions, methods of treatment using immunogenic compositions, methods of evaluating cell-mediated immunity resulting from immunogenic compositions, research models, and methods of making research models, all of which relate to targeting tumor vasculature.

31 Claims, 11 Drawing Sheets

OTHER PUBLICATIONS

Tary-Lehmann, et al. "The human immune system in hu-PBL-SCID mice." *Immunology Today*. 16(11): 529-533 (1995).

Tereb, et al. "Human T Cells Infiltrate and Injure Pig Coronary Artery Grafts with Activated but not Quiescent Endothelium in Immunodeficient Mouse Hosts." *Transplantation*. 71(11): 1622-1630 (2001).

Kershaw et al., "Generation of Gene-Modified T Cells Reactive Against the Angiogenic Kinase Insert Domain-Containing Receptor (KDR) Found on Tumor Vasculature", Human Gene Therapy, 11: 2445-2452 (2000).

Gong, M., et al., "In vivo eradication of prostate cancer tumors in SCID mice using genetically modified human T cells targeted to PSMA," J. Urol., Apr. 2000, vol. 163, No. 4 Suppl., p. 36, abstract #155.

Mincheff, M., et al., "Naked DNA and adenoviral immunizations for immunotherapy of prostate cancer: A phase I/II clinical trial," Eur. Urol., Aug. 2000, vol. 38, No. 2, pp. 208-217.

O'Connell, K., et al., "Endothelial cells transformed by SV40 T antigen cause Kaposi's sarcomalike tumors in nude mice," Am. J. Pathol., Oct. 1991, vol. 139, No. 4, pp. 743-749.

Salgaller, M.L., et al., "Report of immune monitoring of prostate cancer patients undergoing T-cell therapy using dendritic cells pulsed with HLA-A2-specific peptides from prostate-specific membrane antigen (PSMA)," The Prostate, May 1998, vol. 35, No. 2, pp. 144-151.

Yang, J., et al., "Telomerized human microvasculature is functional in vivo," Nat. Biotech., Mar. 1, 2001, vol. 19, No. 3, pp. 219-224.

U.S. Appl. No. 09/380,534, "A Method of Inducing at CTL Response," filed Sep. 1, 1999.

U.S. Appl. No. 09/560,465, "Epitope Synchronization in Antigen Presenting Cells," filed Apr. 28, 2000.

U.S. Appl. No. 09/561,074, "Method of Epitope Discovery," filed Apr. 28, 2000.

U.S. Appl. No. 09/561,571, "Epitope Clusters," filed Apr. 28, 2000.

U.S. Appl. No. 09/561,572, "Expression Vectors Encoding Epitopes or Target-Associated Antigens," filed Apr. 28, 2000.

U.S. Appl. No. 09/776,232, "Method of Inducing a CTL Response," filed Feb. 2, 2001.

U.S. Appl. No. 10/005,905, "Epitope Synchronization in Antigen Presenting Cells," filed Nov. 7, 2001.

U.S. Appl. No. 10/026,066, "Epitope Synchronization in Antigen Presenting Cells," filed Dec. 7, 2001.

U.S. Appl. No. 60/282,211, "Epitope Sequences," filed Apr. 6, 2001.

U.S. Appl. No. 60/336,968, "Expression Vectors Encoding Epitopes of Target-Associated Antigens and Methods for Their Design," filed Nov. 7, 2001.

U.S. Appl. No. 60/337,017, "Epitope Sequences," filed Nov. 7, 2001.

U.S. Appl. No. 60/363,131, "HLA-Transgenic Murine Tumor Cell Line," filed Mar. 7, 2002.

U.S. Appl. No. 60/363,210, "Epitope Sequences," filed Mar. 7, 2002.

Borsi et al., "Differential Expression of the Fibronectin Isoform Containing the ED-B Oncofetal Domain in Normal Human Fibroblast Cell Lines Originating from Different Tissues," *Experimental Cell Research* 199: 98-105 (1992).

Camemolla et al., "A Tumor-associated Fibronectin Isoform Generated by Alternative Splicing of Messenger RNA Precursors," *Eur. Mol. Biol. Organ. J.* 6: 2337-2342 (1987).

Castellani et al., "The Angiogenesis Marker ED-B+ Fibronectin Isoform in Intracranial Meningiomas," *Acta Neurochir (Wien)* 142: 277-282 (2000).

Castellani et al., "The Fibronectin Isoform Containing the ED-B Oncofetal Domain: A Marker of Angiogenesis," *Int. J. Cancer* 59: 612-618 (1994).

Chang et al., "Five Different Anti-Prostate-specific Membrane Antigen (PSMA) Antibodies Confirm PSMA Expression in Tumor-associated Neovasculature," *Cancer Research* 59: 3192-3198 (1999).

Chang et al., "Prostate-specific Membrane Antigen is produced in Tumor-associated Neovasculature," *Clinical Cancer Research* 5: 2674-2681 (1999).

Chang et al., "Mosaic blood vessels in tumors: Frequency of cancer cells in contact with flowing blood," *PNAS* 97: 14608-14613 (2000).

Chevalier et al., "Increased Expression of the Ed-B-Containing Fibronectin (An Embryonic Isoform of Fibronectin) in Human Osteoarthritic Cartilage," *British Journal of Rheumatology* 35: 407-415 (1996).

Chung et al., "Induction of Cytotoxic T Lymphocytes with Peptides In Vitro: Identification of Candidate T-Cell Epitopes in Hepatitis B Virus X Antigen," *Journal of Immunotherapy* 22(4): 279-287 (1999).

Drobyski et al., "Protection from lethal murine graft-versus-host disease without compromise of alloengraftment using transgenic donor T cells expressing a thymidine kinase suicide gene," *Blood* 97: 2506-2513 (2001).

Famound et al., "Fibronectin Isoforms are Differentially Expressed in Normal and Adenomatous Human Anteriro Pituitaries," *Int. J. Cancer* 61: 27-34 (1995).

Gabler et al., "Matrix remodelling in dilated cardimyopathy entails the occurrence of oncofetal fibronectin molecular variants," *Heart* 75: 358-362 (1996).

Kaczmarek et al., "Distribution of Oncofetal Fibronectin Isoforms in Normal, Hyperplastic and Neoplastic Human Breast Tissues," *Int. J. Cancer* 58: 11-16 (1994).

Kanwar et al., "Vascular Attach by 5,6-Dimethylxanthenone-4-acetic Acid Combined with B7.1 (CD80)-mediated Immunotherapy Overcomes Immune Resistance and Leads to the Eradication of Large Tumors and Multiple Tumor Foci," *Cancer Research* 61: 1948-1956 (2001).

Karelina et al., "Interstitial Collagenase and the ED-B Oncofetal Domain of Fibronectin Are Markers of Angiogenesis in Human Skin Tumors," *Cancer Detection and Prevention* 22(5): 438-444 (1998).

Kurokawa et al., "Induction and Clonal Expansion of Tumor-Specific Cytotoxic T Lymphocytes from Renal Cell Carcinoma Patients After Stimulation with Autologous Dendritic Celis Loaded with Tumor Cells," *Int. J. Cancer* 91: 749-756 (2001).

Loridon-Rosa et al., "Distribution of Oncofetal Fibronectin in Human Mammary Tumors: Immunofluorescence Study on Histological Sections," *Cancer Research* 50: 1608-1612 (1990).

Mandel et al., "Oncofetal fibronectins in oral carcinomas: Correlation of two different types," *APMIS* 102:695-702 (1994).

Maniotis et al., "Vascular Channel Formation by Human Melanoma Cells in Vivo and in Vitro: Vasculogenic Mimicry," *American Journal of Pathology* 155: 739-752 (1999).

Matsuura et al., "The oncofetal domain of fibronectin defined by monoclonal antibody FDC-6: Its presence in fibronections from fetal and tumor tissues and its absence in those from normal adult tissues and plasma," *Proc. Natl. Acad. Sci. USA* 82: 6517-6521 (1985).

Midulla et al., "Source of Oncofetal ED-B-containing Fibronectin: Implications of Production by Both Tumor and Endothelial Cells," *Cancer Research* 60: 164-169 (2000).

Neri et al., "Targeting by affinity-matured recombinant antibody fragments of an angiogenesis associated fibronectin isoform," *Nature Biotechnology* 15: 1271-1275 (1997).

Nicolo et al., "Expression of tenascin and of the ED-B containing oncofetal fibronectin isoform in human cancer," *Cell Differentiation and Development* 32: 401-408 (1990).

Nilsson et al., "Targeted Delivery of Tissues Factor to the ED-B Domain of Fibronectin, a Marker of Angiogenesis, Mediates the Infarction of Solid Tumors in Mice," *Cancer Research* 61: 711-716 (2001).

Oyama et al., "Coordinate Oncodevelopmental Modulation of Alternative Splicing of Fibronectin Pre-Messenger RNA at ED-A, ED-B, and CS1 Regions in Human Liver Tumors," *Cancer Research* 53: 2005-2011 (1993).

Pascolo et al., "HLA-A2.1-restricted Education and Cytolytic Activity of CD8+ T Lymphocytes from β2 Microglobulin (β2m)

HLA-A2.1 Monochain Transgenic H-2D$^b$ β2m Double Knockout Mice," *J. Exp. Med.* 185: 2043-2051 (1997).

Pujuguet et al., "Expression of Fibronectin ED-A$^+$ and ED-B$^+$ Isoforms by Human and Experimental Colorectal Cancer," *American Journal of Pathology* 148: 579-592 (1998).

Salgaller et al., "Recognition of Multiple Epitopes in the Human Melanoma Antigen gp100 by Peripheral Blood Lymphocytes Stimulated in Vitro with Synthetic Peptides," *Cancer Research* 55: 4972-4979 (1995).

Scheibenbogen et al., "Analysis of the T Cell Response to Tumor and Viral Peptide Antigens by an IFNγ-Elispot Assay," *Int. J. Cancer* 71: 932-936 (1997).

Seeley et al., "Potent effector function of tumor-sensitized L-selection$^{low}$ T cells against subcutaneous tumors requires LFA-1 co-stimulation," *Otolaryngol Head Neck Surg* 124: 438-441 (2001).

Stauss et al., "Induction of cytotoxic T lymphocytes with peptides in vitro: Identification of candidate T-cell epitopes in human papilloma virus," *Proc. Natl. Acad. Sci. USA* 89: 7871-7875 (1992).

Tarti et al., "A High-Affinity Human Antibody That Targets Tumoral Blood Vessels," *Blood* 94: 192-198 (1999).

Tsai et al., "Identification of Subdominant CTL Epitopes of the GP100 Melanoma-Associated Tumor Antigen by Primary In Vitro Immunization with Peptide-Pulsed Dendritic Cells," *The Journal of Immunology* 158: 1796-1802 (1997).

Yang et al., "Telomerized human microvasculature is functional in vivo," *Nature Biotechnology* 19: 219-224 (2001).

Brekken et al. "Selective inhibition of vascular endothelial growth factor (VEGF) receptor 2 (KDR/Flk-1) activity by a monoclonal anti-VEGF antibody blocks tumor growth in mice." *Cancer Research*, 60(18):5117-5124 (2000).

European Search Report for European Application No. EP 05 01 4175 dated Oct. 10, 2005.

Gouttefangeas et al. "Problem solving for tumor immunotherapy." *Nature Biotechnology*, 18(5):491-492 (2000).

Hadden et al. "Induction of lung fibroblast apoptosis by soluble fibronectin peptides." *American Journal of Respiratory and Critical Care Medicine*, 162(4):1553-1560 (Part 1) (2000).

Kessler et al. "Efficient identification of novel HLA-A*0201-presented cytotoxic T lymphocyte epitopes in the widely expressed tumor antigen PRAME by proteasome-mediated digestion analysis." *Journal of Experimental Medicine*, 193(1):73-88 (2001).

Marty et al. "Production of functionalized single-chain Fv antibody fragments binding to the ED-B domain of B-isoform of fibronectin in the Pichia pastoris." *Protein Expression and Purification*, 21(1):156-164 (2001).

Melief, C.J. "Towards T-cell immunotherapy of cancer (Meeting abstract)." *Cancerlit.* 1996.

Morel et al. "Processing of some antigens by the standard proteasome but not by the immunoproteasome results in poor presentation by dendritic cells." *Immunity*, 12(1)107-117 (2000).

Pamer et al. "Mechanisms of MHC class I-restricted antigen processing." *Annual Review of Immunology.* pp. 323-358 (1998).

Rock et al. "Degradation of cell proteins and the generation of MHC class I-presented peptides." *Annual Review of Immunology*, 17:739-779 (1999).

\* cited by examiner

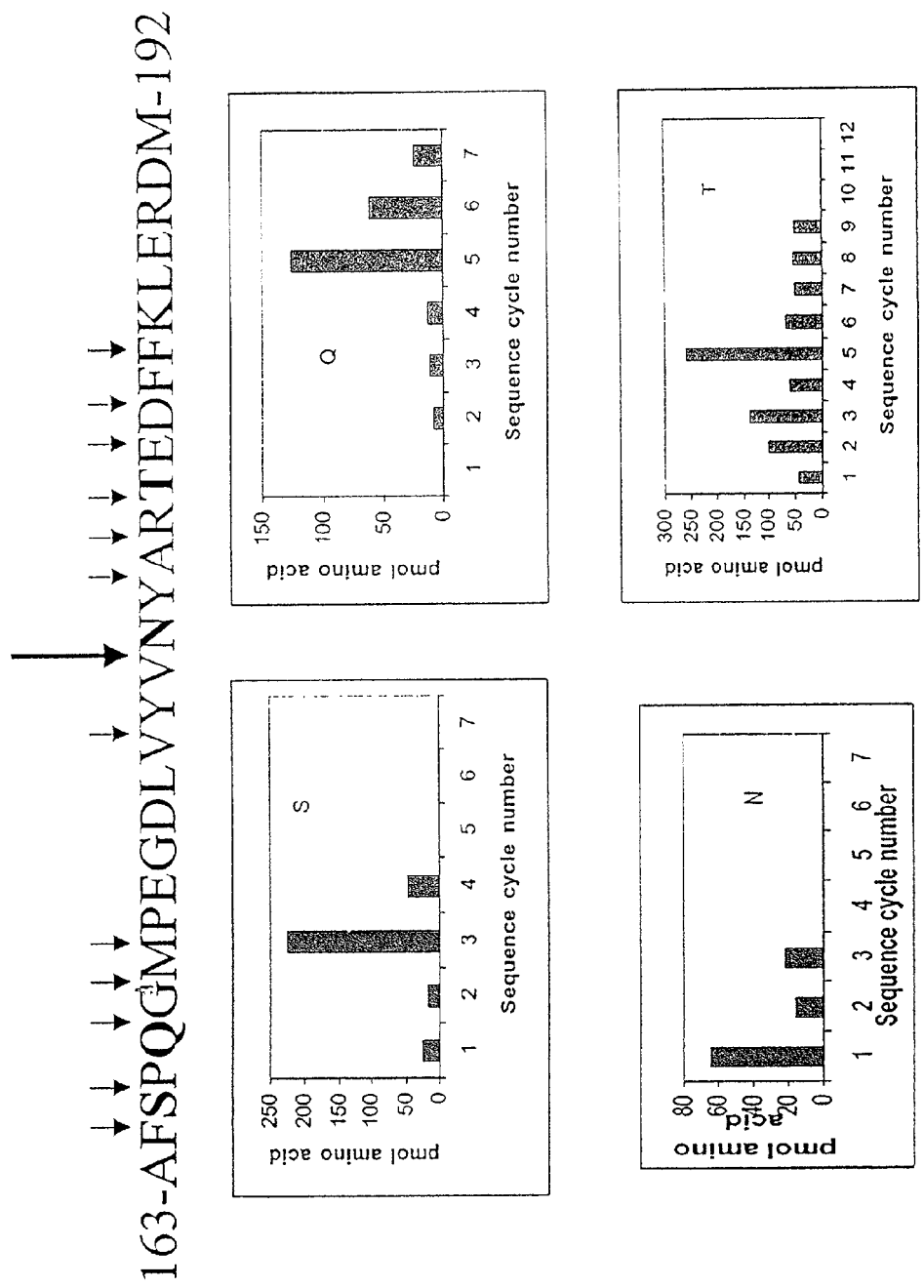
Fig. Pool sequencing of PSMA_163-192 Digested for 60 min by Proteasome   FIG 1A Fig. Pool sequencing of PSMA_163-192 Digested for 60 min by Proteasome Fig. Pool sequencing of PSMA_163-192 Digested for 60 min by Proteasome Fig. Pool sequencing of PSMA_281-310 digested for 60 min by Proteasome

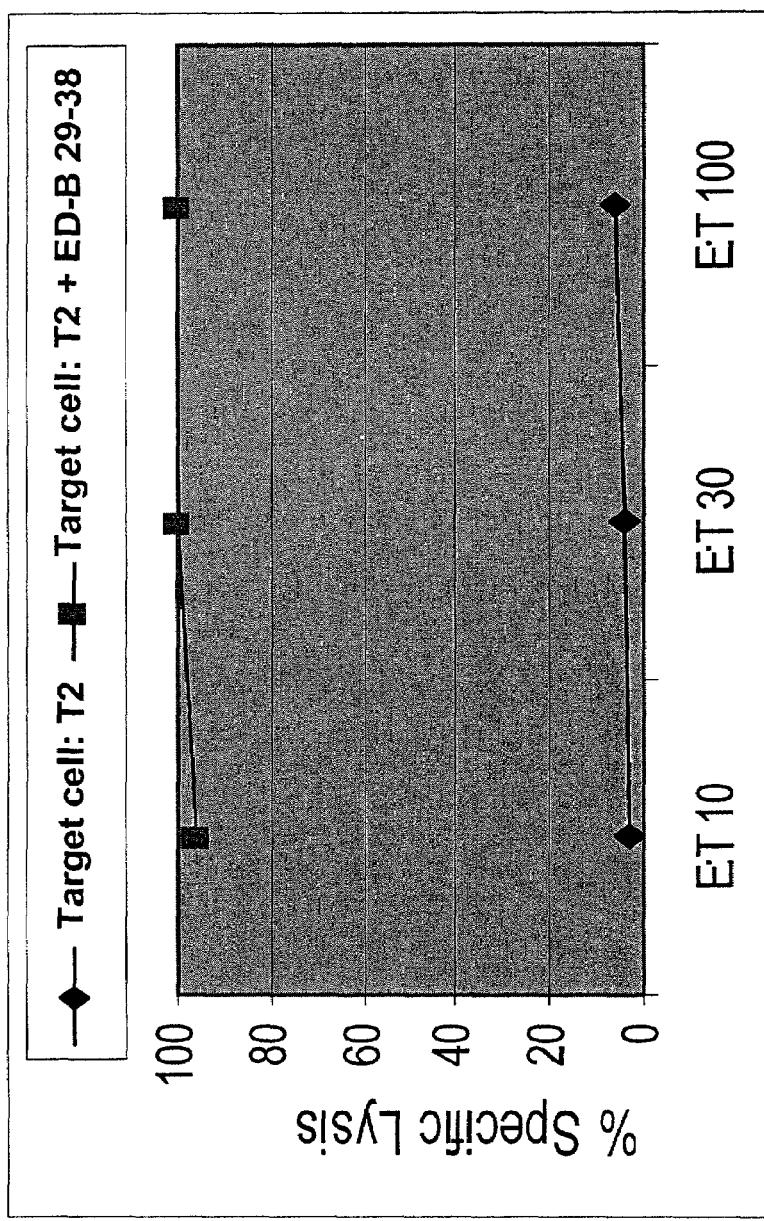

SEQUENCE LISTING

<160> NUMBER OF SEQ ID NOS: 159

<210> SEQ ID NO 1
<211> LENGTH: 750
<212> TYPE: PRT
<213> ORGANISM: Homo sapien

<400> SEQUENCE: 1

```
Met Trp Asn Leu Leu His Glu Thr Asp Ser Ala Val Ala Thr Ala Arg
 1               5                  10                  15

Arg Pro Arg Trp Leu Cys Ala Gly Ala Leu Val Leu Ala Gly Gly Phe
            20                  25                  30

Phe Leu Leu Gly Phe Leu Phe Gly Trp Phe Ile Lys Ser Ser Asn Glu
        35                  40                  45

Ala Thr Asn Ile Thr Pro Lys His Asn Met Lys Ala Phe Leu Asp Glu
    50                  55                  60

Leu Lys Ala Glu Asn Ile Lys Lys Phe Leu Tyr Asn Phe Thr Gln Ile
65                  70                  75                  80

Pro His Leu Ala Gly Thr Glu Gln Asn Phe Gln Leu Ala Lys Gln Ile
                85                  90                  95

Gln Ser Gln Trp Lys Glu Phe Gly Leu Asp Ser Val Glu Leu Ala His
            100                 105                 110

Tyr Asp Val Leu Leu Ser Tyr Pro Asn Lys Thr His Pro Asn Tyr Ile
        115                 120                 125

Ser Ile Ile Asn Glu Asp Gly Asn Glu Ile Phe Asn Thr Ser Leu Phe
    130                 135                 140

Glu Pro Pro Pro Gly Tyr Glu Asn Val Ser Asp Ile Val Pro Pro
145                 150                 155                 160

Phe Ser Ala Phe Ser Pro Gln Gly Met Pro Glu Gly Asp Leu Val Tyr
                165                 170                 175

Val Asn Tyr Ala Arg Thr Glu Asp Phe Phe Lys Leu Glu Arg Asp Met
            180                 185                 190

Lys Ile Asn Cys Ser Gly Lys Ile Val Ile Ala Arg Tyr Gly Lys Val
        195                 200                 205

Phe Arg Gly Asn Lys Val Lys Asn Ala Gln Leu Ala Gly Ala Lys Gly
    210                 215                 220

Val Ile Leu Tyr Ser Asp Pro Ala Asp Tyr Phe Ala Pro Gly Val Lys
225                 230                 235                 240

Ser Tyr Pro Asp Gly Trp Asn Leu Pro Gly Gly Val Gln Arg Gly
                245                 250                 255

Asn Ile Leu Asn Leu Asn Gly Ala Gly Asp Pro Leu Thr Pro Gly Tyr
            260                 265                 270

Pro Ala Asn Glu Tyr Ala Tyr Arg Arg Gly Ile Ala Glu Ala Val Gly
        275                 280                 285

Leu Pro Ser Ile Pro Val His Pro Ile Gly Tyr Tyr Asp Ala Gln Lys
    290                 295                 300

Leu Leu Glu Lys Met Gly Gly Ser Ala Pro Pro Asp Ser Ser Trp Arg
305                 310                 315                 320

Gly Ser Leu Lys Val Pro Tyr Asn Val Gly Pro Gly Phe Thr Gly Asn
                325                 330                 335

Phe Ser Thr Gln Lys Val Lys Met His Ile His Ser Thr Asn Glu Val
            340                 345                 350

Thr Arg Ile Tyr Asn Val Ile Gly Thr Leu Arg Gly Ala Val Glu Pro
```

```
                355                 360                 365
Asp Arg Tyr Val Ile Leu Gly Gly His Arg Asp Ser Trp Val Phe Gly
    370                 375                 380

Gly Ile Asp Pro Gln Ser Gly Ala Ala Val His Glu Ile Val Arg
385                 390                 395                 400

Ser Phe Gly Thr Leu Lys Lys Glu Gly Trp Arg Pro Arg Thr Ile
                405                 410                 415

Leu Phe Ala Ser Trp Asp Ala Glu Glu Phe Gly Leu Leu Gly Ser Thr
                420                 425                 430

Glu Trp Ala Glu Glu Asn Ser Arg Leu Leu Gln Glu Arg Gly Val Ala
                435                 440                 445

Tyr Ile Asn Ala Asp Ser Ser Ile Glu Gly Asn Tyr Thr Leu Arg Val
450                 455                 460

Asp Cys Thr Pro Leu Met Tyr Ser Leu Val His Asn Leu Thr Lys Glu
465                 470                 475                 480

Leu Lys Ser Pro Asp Glu Gly Phe Glu Gly Lys Ser Leu Tyr Glu Ser
                485                 490                 495

Trp Thr Lys Lys Ser Pro Ser Pro Glu Phe Ser Gly Met Pro Arg Ile
                500                 505                 510

Ser Lys Leu Gly Ser Gly Asn Asp Phe Glu Val Phe Phe Gln Arg Leu
                515                 520                 525

Gly Ile Ala Ser Gly Arg Ala Arg Tyr Thr Lys Asn Trp Glu Thr Asn
                530                 535                 540

Lys Phe Ser Gly Tyr Pro Leu Tyr His Ser Val Tyr Glu Thr Tyr Glu
545                 550                 555                 560

Leu Val Glu Lys Phe Tyr Asp Pro Met Phe Lys Tyr His Leu Thr Val
                565                 570                 575

Ala Gln Val Arg Gly Gly Met Val Phe Glu Leu Ala Asn Ser Ile Val
                580                 585                 590

Leu Pro Phe Asp Cys Arg Asp Tyr Ala Val Val Leu Arg Lys Tyr Ala
                595                 600                 605

Asp Lys Ile Tyr Ser Ile Ser Met Lys His Pro Gln Glu Met Lys Thr
                610                 615                 620

Tyr Ser Val Ser Phe Asp Ser Leu Phe Ser Ala Val Lys Asn Phe Thr
625                 630                 635                 640

Glu Ile Ala Ser Lys Phe Ser Glu Arg Leu Gln Asp Phe Asp Lys Ser
                645                 650                 655

Asn Pro Ile Val Leu Arg Met Met Asn Asp Gln Leu Met Phe Leu Glu
                660                 665                 670

Arg Ala Phe Ile Asp Pro Leu Gly Leu Pro Asp Arg Pro Phe Tyr Arg
                675                 680                 685

His Val Ile Tyr Ala Pro Ser Ser His Asn Lys Tyr Ala Gly Glu Ser
                690                 695                 700

Phe Pro Gly Ile Tyr Asp Ala Leu Phe Asp Ile Glu Ser Lys Val Asp
705                 710                 715                 720

Pro Ser Lys Ala Trp Gly Glu Val Lys Arg Gln Ile Tyr Val Ala Ala
                725                 730                 735

Phe Thr Val Gln Ala Ala Ala Glu Thr Leu Ser Glu Val Ala
                740                 745                 750

<210> SEQ ID NO 2
<211> LENGTH: 2653
<212> TYPE: DNA
<213> ORGANISM: Homo sapien
```

-continued

<400> SEQUENCE: 2

```
ctcaaaaggg gccggatttc cttctcctgg aggcagatgt tgcctctctc tctcgctcgg      60
attggttcag tgcactctag aaacactgct gtggtggaga aactggaccc caggtctgga     120
gcgaattcca gcctgcaggg ctgataagcg aggcattagt gagattgaga gagactttac     180
cccgccgtgg tggttggagg gcgcgcagta gagcagcagc acaggcgcgg gtcccgggag     240
gccggctctg ctcgcgccga gatgtggaat ctccttcacg aaaccgactc ggctgtggcc     300
accgcgcgcc gcccgcgctg gctgtgcgct ggggcgctgg tgctggcggg tggcttcttt     360
ctcctcggct tcctcttcgg gtggtttata aaatcctcca atgaagctac taacattact     420
ccaaagcata atatgaaagc attttttggat gaattgaaag ctgagaacat caagaagttc     480
ttatataatt ttacacagat accacattta gcaggaacag aacaaaactt tcagcttgca     540
aagcaaattc aatcccagtg aaagaatttt ggcctggatt ctgttgagct agcacattat     600
gatgtcctgt tgtcctaccc aaataagact catcccaact acatctcaat aattaatgaa     660
gatgaaaatg agattttcaa cacatcatta tttgaaccac ctcctccagg atatgaaaat     720
gtttcggata ttgtaccacc tttcagtgct ttctctcctc aaggaatgcc agagggcgat     780
ctagtgtatg ttaactatgc acgaactgaa gacttcttta aattggaacg ggacatgaaa     840
atcaattgct ctgggaaaat tgtaattgcc agatatggga agttttcag aggaaataag      900
gttaaaaatg cccagctggc aggggccaaa ggagtcattc tctactccga ccctgctgac     960
tactttgctc ctggggtgaa gtcctatcca gatggttgga tcttcctgg aggtggtgtc     1020
cagcgtggaa atatcctaaa tctgaatggt gcaggagacc ctctcacacc aggttaccca     1080
gcaaatgaat atgcttatag gcgtggaatt gcagaggctg ttggtcttcc aagtattcct     1140
gttcatccaa ttggatacta tgatgcacag aagctcctag aaaaaatggg tggctcagca     1200
ccaccagata gcagctggag aggaagtctc aaagtgccct acaatgttgg acctggcttt     1260
actggaaact tttctacaca aaaagtcaag atgcacatcc actctaccaa tgaagtgaca     1320
agaatttaca atgtgatagg tactctcaga ggagcagtgg aaccagacag atatgtcatt     1380
ctgggaggtc accgggactc atgggtgttt ggtggtattg accctcagag tggagcagct     1440
gttgttcatg aaattgtgag gagctttgga acactgaaaa aggaagggtg gagacctaga     1500
agaacaattt tgtttgcaag ctgggatgca gaagaatttg gtcttcttgg ttctactgag     1560
tgggcagagg agaattcaag actccttcaa gagcgtggcg tggcttatat taatgctgac     1620
tcatctatag aaggaaacta cactctgaga gttgattgta caccgctgat gtacagcttg     1680
gtacacaacc taacaaaaga gctgaaaagc cctgatgaag ctttgaagg caaatctctt     1740
tatgaaagtt ggactaaaaa aagtccttcc ccagagttca gtggcatgcc aggataagc     1800
aaattgggat ctgaaatga ttttgaggtg ttcttccaac gacttggaat tgcttcaggc     1860
agagcacggt atactaaaaa ttgggaaaca acaaattca gcggctatcc actgtatcac     1920
agtgtctatg aaacatatga gttggtggaa agtttttatg atccaatgtt taaatatcac     1980
ctcactgtgg cccaggttcg aggagggatg gtgtttgagc tagccaattc catagtgctc     2040
cctttttgatt gtcgagatta tgctgtagtt ttaagaaagt atgctgacaa aatctacagt     2100
atttctatga acatccaca ggaaatgaag acatacagtg tatcatttga ttcacttttt     2160
tctgcagtaa agaatttttac agaaattgct tccaagttca gtgagagact ccaggacttt     2220
gacaaaagca acccaatagt attaagaatg atgaatgatc aactcatgtt tctggaagga    2280
```

-continued

```
gcatttattg atccattagg gttaccagac aggccttttt ataggcatgt catctatgct    2340
ccaagcagcc acaacaagta tgcaggggag tcattcccag gaatttatga tgctctgttt    2400
gatattgaaa gcaaagtgga cccttccaag gcctggggag aagtgaagag acagatttat    2460
gttgcagcct tcacagtgca ggcagctgca gagactttga gtgaagtagc ctaagaggat    2520
tctttagaga atccgtattg aatttgtgtg gtatgtcact cagaaagaat cgtaatgggt    2580
atattgataa attttaaaat tggtatattt gaaataaagt tgaatattat ataaaaaaa    2640 aaaaaaaaaa aaa                                                      2653
```

<210> SEQ ID NO 3
<211> LENGTH: 30
<212> TYPE: PRT
<213> ORGANISM: Homo sapien

<400> SEQUENCE: 3

```
Ala Phe Ser Pro Gln Gly Met Pro Glu Gly Asp Leu Val Tyr Val Asn
 1               5                  10                  15

Tyr Ala Arg Thr Glu Asp Phe Phe Lys Leu Glu Arg Asp Met
            20                  25                  30
```

<210> SEQ ID NO 4
<211> LENGTH: 23
<212> TYPE: PRT
<213> ORGANISM: Homo sapien

<400> SEQUENCE: 4

```
Gly Met Pro Glu Gly Asp Leu Val Tyr Val Asn Tyr Ala Arg Thr Glu
 1               5                  10                  15

Asp Phe Phe Lys Leu Glu Arg
            20
```

<210> SEQ ID NO 5
<211> LENGTH: 9
<212> TYPE: PRT
<213> ORGANISM: Homo sapien

<400> SEQUENCE: 5

```
Met Pro Glu Gly Asp Leu Val Tyr Val
 1               5
```

<210> SEQ ID NO 6
<211> LENGTH: 10
<212> TYPE: PRT
<213> ORGANISM: Homo sapien

<400> SEQUENCE: 6

```
Gly Met Pro Glu Gly Asp Leu Val Tyr Val
 1               5                  10
```

<210> SEQ ID NO 7
<211> LENGTH: 9
<212> TYPE: PRT
<213> ORGANISM: Homo sapien

<400> SEQUENCE: 7

```
Gly Met Pro Glu Gly Asp Leu Val Tyr
 1               5
```

<210> SEQ ID NO 8
<211> LENGTH: 10
<212> TYPE: PRT

<213> ORGANISM: Homo sapien

<400> SEQUENCE: 8

Gln Gly Met Pro Glu Gly Asp Leu Val Tyr
 1               5                  10

<210> SEQ ID NO 9
<211> LENGTH: 8
<212> TYPE: PRT
<213> ORGANISM: Homo sapien

<400> SEQUENCE: 9

Met Pro Glu Gly Asp Leu Val Tyr
 1               5

<210> SEQ ID NO 10
<211> LENGTH: 9
<212> TYPE: PRT
<213> ORGANISM: Homo sapien

<400> SEQUENCE: 10

Glu Gly Asp Leu Val Tyr Val Asn Tyr
 1               5

<210> SEQ ID NO 11
<211> LENGTH: 10
<212> TYPE: PRT
<213> ORGANISM: Homo sapien

<400> SEQUENCE: 11

Pro Glu Gly Asp Leu Val Tyr Val Asn Tyr
 1               5                  10

<210> SEQ ID NO 12
<211> LENGTH: 10
<212> TYPE: PRT
<213> ORGANISM: Homo sapien

<400> SEQUENCE: 12

Leu Val Tyr Val Asn Tyr Ala Arg Thr Glu
 1               5                  10

<210> SEQ ID NO 13
<211> LENGTH: 9
<212> TYPE: PRT
<213> ORGANISM: Homo sapien

<400> SEQUENCE: 13

Val Asn Tyr Ala Arg Thr Glu Asp Phe
 1               5

<210> SEQ ID NO 14
<211> LENGTH: 10
<212> TYPE: PRT
<213> ORGANISM: Homo sapien

<400> SEQUENCE: 14

Tyr Val Asn Tyr Ala Arg Thr Glu Asp Phe
 1               5                  10

<210> SEQ ID NO 15
<211> LENGTH: 9
<212> TYPE: PRT
<213> ORGANISM: Homo sapien

```
<400> SEQUENCE: 15

Asn Tyr Ala Arg Thr Glu Asp Phe Phe
 1               5

<210> SEQ ID NO 16
<211> LENGTH: 8
<212> TYPE: PRT
<213> ORGANISM: Homo sapien

<400> SEQUENCE: 16

Tyr Ala Arg Thr Glu Asp Phe Phe
 1               5

<210> SEQ ID NO 17
<211> LENGTH: 9
<212> TYPE: PRT
<213> ORGANISM: Homo sapien

<400> SEQUENCE: 17

Arg Thr Glu Asp Phe Phe Lys Leu Glu
 1               5

<210> SEQ ID NO 18
<211> LENGTH: 30
<212> TYPE: PRT
<213> ORGANISM: Homo sapien

<400> SEQUENCE: 18

Arg Gly Ile Ala Glu Ala Val Gly Leu Pro Ser Ile Pro Val His Pro
 1               5                  10                  15

Ile Gly Tyr Tyr Asp Ala Gln Lys Leu Leu Glu Lys Met Gly
             20                  25                  30

<210> SEQ ID NO 19
<211> LENGTH: 25
<212> TYPE: PRT
<213> ORGANISM: Homo sapien

<400> SEQUENCE: 19

Ile Ala Glu Ala Val Gly Leu Pro Ser Ile Pro Val His Pro Ile Gly
 1               5                  10                  15

Tyr Tyr Asp Ala Gln Lys Leu Leu Glu
             20                  25

<210> SEQ ID NO 20
<211> LENGTH: 9
<212> TYPE: PRT
<213> ORGANISM: Homo sapien

<400> SEQUENCE: 20

Leu Pro Ser Ile Pro Val His Pro Ile
 1               5

<210> SEQ ID NO 21
<211> LENGTH: 10
<212> TYPE: PRT
<213> ORGANISM: Homo sapien

<400> SEQUENCE: 21

Gly Leu Pro Ser Ile Pro Val His Pro Ile
 1               5                  10

<210> SEQ ID NO 22
```

<211> LENGTH: 9
<212> TYPE: PRT
<213> ORGANISM: Homo sapien

<400> SEQUENCE: 22

Ile Gly Tyr Tyr Asp Ala Gln Lys Leu
1               5

<210> SEQ ID NO 23
<211> LENGTH: 10
<212> TYPE: PRT
<213> ORGANISM: Homo sapien

<400> SEQUENCE: 23

Pro Ile Gly Tyr Tyr Asp Ala Gln Lys Leu
1               5                   10

<210> SEQ ID NO 24
<211> LENGTH: 9
<212> TYPE: PRT
<213> ORGANISM: Homo sapien

<400> SEQUENCE: 24

Ser Ile Pro Val His Pro Ile Gly Tyr
1               5

<210> SEQ ID NO 25
<211> LENGTH: 10
<212> TYPE: PRT
<213> ORGANISM: Homo sapien

<400> SEQUENCE: 25

Pro Ser Ile Pro Val His Pro Ile Gly Tyr
1               5                   10

<210> SEQ ID NO 26
<211> LENGTH: 8
<212> TYPE: PRT
<213> ORGANISM: Homo sapien

<400> SEQUENCE: 26

Ile Pro Val His Pro Ile Gly Tyr
1               5

<210> SEQ ID NO 27
<211> LENGTH: 9
<212> TYPE: PRT
<213> ORGANISM: Homo sapien

<400> SEQUENCE: 27

Tyr Tyr Asp Ala Gln Lys Leu Leu Glu
1               5

<210> SEQ ID NO 28
<211> LENGTH: 27
<212> TYPE: PRT
<213> ORGANISM: Homo sapien

<400> SEQUENCE: 28

Ser Ser Ile Glu Gly Asn Tyr Thr Leu Arg Val Asp Cys Thr Pro Leu
1               5                   10                  15

Met Tyr Ser Leu Val His Leu Thr Lys Glu Leu
            20                  25

```
<210> SEQ ID NO 29
<211> LENGTH: 9
<212> TYPE: PRT
<213> ORGANISM: Homo sapien

<400> SEQUENCE: 29

Ile Glu Gly Asn Tyr Thr Leu Arg Val
 1               5

<210> SEQ ID NO 30
<211> LENGTH: 10
<212> TYPE: PRT
<213> ORGANISM: Homo sapien

<400> SEQUENCE: 30

Ser Ile Glu Gly Asn Tyr Thr Leu Arg Val
 1               5                   10

<210> SEQ ID NO 31
<211> LENGTH: 8
<212> TYPE: PRT
<213> ORGANISM: Homo sapien

<400> SEQUENCE: 31

Glu Gly Asn Tyr Thr Leu Arg Val
 1               5

<210> SEQ ID NO 32
<211> LENGTH: 9
<212> TYPE: PRT
<213> ORGANISM: Homo sapien

<400> SEQUENCE: 32

Thr Leu Arg Val Asp Cys Thr Pro Leu
 1               5

<210> SEQ ID NO 33
<211> LENGTH: 10
<212> TYPE: PRT
<213> ORGANISM: Homo sapien

<400> SEQUENCE: 33

Tyr Thr Leu Arg Val Asp Cys Thr Pro Leu
 1               5                   10

<210> SEQ ID NO 34
<211> LENGTH: 9
<212> TYPE: PRT
<213> ORGANISM: Homo sapien

<400> SEQUENCE: 34

Leu Arg Val Asp Cys Thr Pro Leu Met
 1               5

<210> SEQ ID NO 35
<211> LENGTH: 9
<212> TYPE: PRT
<213> ORGANISM: Homo sapien

<400> SEQUENCE: 35

Arg Val Asp Cys Thr Pro Leu Met Tyr
 1               5

<210> SEQ ID NO 36
<211> LENGTH: 10
```

<212> TYPE: PRT
<213> ORGANISM: Homo sapien

<400> SEQUENCE: 36

Leu Arg Val Asp Cys Thr Pro Leu Met Tyr
1               5                   10

<210> SEQ ID NO 37
<211> LENGTH: 35
<212> TYPE: PRT
<213> ORGANISM: Homo sapien

<400> SEQUENCE: 37

Phe Asp Lys Ser Asn Pro Ile Val Leu Arg Met Met Asn Asp Gln Leu
1               5                   10                  15

Met Phe Leu Glu Arg Ala Phe Ile Asp Pro Leu Gly Leu Pro Asp Arg
            20                  25                  30

Pro Phe Tyr
        35

<210> SEQ ID NO 38
<211> LENGTH: 22
<212> TYPE: PRT
<213> ORGANISM: Homo sapien

<400> SEQUENCE: 38

Val Leu Arg Met Met Asn Asp Gln Leu Met Phe Leu Glu Arg Ala Phe
1               5                   10                  15

Ile Asp Pro Leu Gly Leu
            20

<210> SEQ ID NO 39
<211> LENGTH: 9
<212> TYPE: PRT
<213> ORGANISM: Homo sapien

<400> SEQUENCE: 39

Met Met Asn Asp Gln Leu Met Phe Leu
1               5

<210> SEQ ID NO 40
<211> LENGTH: 10
<212> TYPE: PRT
<213> ORGANISM: Homo sapien

<400> SEQUENCE: 40

Arg Met Met Asn Asp Gln Leu Met Phe Leu
1               5                   10

<210> SEQ ID NO 41
<211> LENGTH: 9
<212> TYPE: PRT
<213> ORGANISM: Homo sapien

<400> SEQUENCE: 41

Arg Met Met Asn Asp Gln Leu Met Phe
1               5

<210> SEQ ID NO 42
<211> LENGTH: 9
<212> TYPE: PRT
<213> ORGANISM: Homo sapien

<400> SEQUENCE: 42

```
Leu Leu His Glu Thr Asp Ser Ala Val
 1               5
```

<210> SEQ ID NO 43
<211> LENGTH: 9
<212> TYPE: PRT
<213> ORGANISM: Homo sapien

<400> SEQUENCE: 43

```
Ala Thr Ala Arg Arg Pro Arg Trp Leu
 1               5
```

<210> SEQ ID NO 44
<211> LENGTH: 9
<212> TYPE: PRT
<213> ORGANISM: Homo sapien

<400> SEQUENCE: 44

```
Thr Pro Lys His Asn Met Lys Ala Phe
 1               5
```

<210> SEQ ID NO 45
<211> LENGTH: 10
<212> TYPE: PRT
<213> ORGANISM: Homo sapien

<400> SEQUENCE: 45

```
Glu Leu Lys Ala Glu Asn Ile Lys Lys Phe
 1               5                  10
```

<210> SEQ ID NO 46
<211> LENGTH: 9
<212> TYPE: PRT
<213> ORGANISM: Homo sapien
<220> FEATURE:
<221> NAME/KEY: VARIANT
<222> LOCATION: (7)...(7)
<223> OTHER INFORMATION: Xaa = His or Tyr

<400> SEQUENCE: 46

```
Asn Ile Lys Lys Phe Leu Xaa Asn Phe
 1               5
```

<210> SEQ ID NO 47
<211> LENGTH: 10
<212> TYPE: PRT
<213> ORGANISM: Homo sapien
<220> FEATURE:
<221> NAME/KEY: VARIANT
<222> LOCATION: (8)...(8)
<223> OTHER INFORMATION: Xaa = His or Tyr

<400> SEQUENCE: 47

```
Glu Asn Ile Lys Lys Phe Leu Xaa Asn Phe
 1               5                  10
```

<210> SEQ ID NO 48
<211> LENGTH: 9
<212> TYPE: PRT
<213> ORGANISM: Homo sapien

<400> SEQUENCE: 48

```
Ala Gly Ala Lys Gly Val Ile Leu Tyr
 1               5
```

```
<210> SEQ ID NO 49
<211> LENGTH: 10
<212> TYPE: PRT
<213> ORGANISM: Homo sapien

<400> SEQUENCE: 49

Pro Leu Met Tyr Ser Leu Val His Asn Leu
 1               5                  10

<210> SEQ ID NO 50
<211> LENGTH: 9
<212> TYPE: PRT
<213> ORGANISM: Homo sapien

<400> SEQUENCE: 50

Leu Met Tyr Ser Leu Val His Asn Leu
 1               5

<210> SEQ ID NO 51
<211> LENGTH: 9
<212> TYPE: PRT
<213> ORGANISM: Homo sapien

<400> SEQUENCE: 51

Arg Val Asp Cys Thr Pro Leu Met Tyr
 1               5

<210> SEQ ID NO 52
<211> LENGTH: 9
<212> TYPE: PRT
<213> ORGANISM: Homo sapien

<400> SEQUENCE: 52

Asp Cys Thr Pro Leu Met Tyr Ser Leu
 1               5

<210> SEQ ID NO 53
<211> LENGTH: 9
<212> TYPE: PRT
<213> ORGANISM: Homo sapien

<400> SEQUENCE: 53

Ser Gly Met Pro Arg Ile Ser Lys Leu
 1               5

<210> SEQ ID NO 54
<211> LENGTH: 10
<212> TYPE: PRT
<213> ORGANISM: Homo sapien

<400> SEQUENCE: 54

Phe Ser Gly Met Pro Arg Ile Ser Lys Leu
 1               5                  10

<210> SEQ ID NO 55
<211> LENGTH: 8
<212> TYPE: PRT
<213> ORGANISM: Homo sapien

<400> SEQUENCE: 55

Gly Asn Lys Val Lys Asn Ala Gln
 1               5

<210> SEQ ID NO 56
<211> LENGTH: 8
```

```
<212> TYPE: PRT
<213> ORGANISM: Homo sapien

<400> SEQUENCE: 56

Ile Ala Arg Tyr Gly Lys Val Phe
1               5

<210> SEQ ID NO 57
<211> LENGTH: 9
<212> TYPE: PRT
<213> ORGANISM: Homo sapien

<400> SEQUENCE: 57

Ala Gln Leu Ala Gly Ala Lys Gly Val
1               5

<210> SEQ ID NO 58
<211> LENGTH: 9
<212> TYPE: PRT
<213> ORGANISM: Homo sapien

<400> SEQUENCE: 58

Lys Val Phe Arg Gly Asn Lys Val Lys
1               5

<210> SEQ ID NO 59
<211> LENGTH: 9
<212> TYPE: PRT
<213> ORGANISM: Homo sapien

<400> SEQUENCE: 59

Gly Asn Lys Val Lys Asn Ala Gln Leu
1               5

<210> SEQ ID NO 60
<211> LENGTH: 9
<212> TYPE: PRT
<213> ORGANISM: Homo sapien

<400> SEQUENCE: 60

Thr Pro Gly Tyr Pro Ala Asn Glu Tyr
1               5

<210> SEQ ID NO 61
<211> LENGTH: 10
<212> TYPE: PRT
<213> ORGANISM: Homo sapien

<400> SEQUENCE: 61

Leu Thr Pro Gly Tyr Pro Ala Asn Glu Tyr
1               5                   10

<210> SEQ ID NO 62
<211> LENGTH: 9
<212> TYPE: PRT
<213> ORGANISM: Homo sapien

<400> SEQUENCE: 62

Gly Tyr Pro Ala Asn Glu Tyr Ala Tyr
1               5

<210> SEQ ID NO 63
<211> LENGTH: 10
<212> TYPE: PRT
<213> ORGANISM: Homo sapien
```

```
<400> SEQUENCE: 63

Pro Gly Tyr Pro Ala Asn Glu Tyr Ala Tyr
 1               5                  10

<210> SEQ ID NO 64
<211> LENGTH: 9
<212> TYPE: PRT
<213> ORGANISM: Homo sapien

<400> SEQUENCE: 64

Asp Pro Leu Thr Pro Gly Tyr Pro Ala
 1               5

<210> SEQ ID NO 65
<211> LENGTH: 9
<212> TYPE: PRT
<213> ORGANISM: Homo sapien

<400> SEQUENCE: 65

Ser Leu Tyr Glu Ser Trp Thr Lys Lys
 1               5

<210> SEQ ID NO 66
<211> LENGTH: 10
<212> TYPE: PRT
<213> ORGANISM: Homo sapien

<400> SEQUENCE: 66

Lys Ser Leu Tyr Glu Ser Trp Thr Lys Lys
 1               5                  10

<210> SEQ ID NO 67
<211> LENGTH: 9
<212> TYPE: PRT
<213> ORGANISM: Homo sapien

<400> SEQUENCE: 67

Glu Gly Phe Glu Gly Lys Ser Leu Tyr
 1               5

<210> SEQ ID NO 68
<211> LENGTH: 10
<212> TYPE: PRT
<213> ORGANISM: Homo sapien

<400> SEQUENCE: 68

Asp Glu Gly Phe Glu Gly Lys Ser Leu Tyr
 1               5                  10

<210> SEQ ID NO 69
<211> LENGTH: 9
<212> TYPE: PRT
<213> ORGANISM: Homo sapien

<400> SEQUENCE: 69

Thr Lys Lys Ser Pro Ser Pro Glu Phe
 1               5

<210> SEQ ID NO 70
<211> LENGTH: 10
<212> TYPE: PRT
<213> ORGANISM: Homo sapien

<400> SEQUENCE: 70
```

Trp Thr Lys Ser Pro Ser Pro Glu Phe
1               5                   10

<210> SEQ ID NO 71
<211> LENGTH: 10
<212> TYPE: PRT
<213> ORGANISM: Homo sapien

<400> SEQUENCE: 71

Ser Leu Tyr Glu Ser Trp Thr Lys Lys Ser
1               5                   10

<210> SEQ ID NO 72
<211> LENGTH: 8
<212> TYPE: PRT
<213> ORGANISM: Homo sapien

<400> SEQUENCE: 72

Trp Gly Glu Val Lys Arg Gln Ile
1               5

<210> SEQ ID NO 73
<211> LENGTH: 9
<212> TYPE: PRT
<213> ORGANISM: Homo sapien

<400> SEQUENCE: 73

Ala Trp Gly Glu Val Lys Arg Gln Ile
1               5

<210> SEQ ID NO 74
<211> LENGTH: 10
<212> TYPE: PRT
<213> ORGANISM: Homo sapien

<400> SEQUENCE: 74

Lys Ala Trp Gly Glu Val Lys Arg Gln Ile
1               5                   10

<210> SEQ ID NO 75
<211> LENGTH: 8
<212> TYPE: PRT
<213> ORGANISM: Homo sapien

<400> SEQUENCE: 75

Lys Ala Trp Gly Glu Val Lys Arg
1               5

<210> SEQ ID NO 76
<211> LENGTH: 9
<212> TYPE: PRT
<213> ORGANISM: Homo sapien

<400> SEQUENCE: 76

Ser Lys Ala Trp Gly Glu Val Lys Arg
1               5

<210> SEQ ID NO 77
<211> LENGTH: 9
<212> TYPE: PRT
<213> ORGANISM: Homo sapien

<400> SEQUENCE: 77

Gln Ile Tyr Val Ala Ala Phe Thr Val

```
<210> SEQ ID NO 78
<211> LENGTH: 9
<212> TYPE: PRT
<213> ORGANISM: Homo sapien

<400> SEQUENCE: 78

Tyr Val Ala Ala Phe Thr Val Gln Ala
 1               5

<210> SEQ ID NO 79
<211> LENGTH: 9
<212> TYPE: PRT
<213> ORGANISM: Homo sapien

<400> SEQUENCE: 79

Trp Gly Glu Val Lys Arg Gln Ile Tyr
 1               5

<210> SEQ ID NO 80
<211> LENGTH: 9
<212> TYPE: PRT
<213> ORGANISM: Homo sapien

<400> SEQUENCE: 80

Glu Val Lys Arg Gln Ile Tyr Val Ala
 1               5

<210> SEQ ID NO 81
<211> LENGTH: 9
<212> TYPE: PRT
<213> ORGANISM: Homo sapien

<400> SEQUENCE: 81

Thr Val Gln Ala Ala Ala Glu Thr Leu
 1               5

<210> SEQ ID NO 82
<211> LENGTH: 10
<212> TYPE: PRT
<213> ORGANISM: Homo sapien

<400> SEQUENCE: 82

Phe Thr Val Gln Ala Ala Ala Glu Thr Leu
 1               5                  10

<210> SEQ ID NO 83
<211> LENGTH: 9
<212> TYPE: PRT
<213> ORGANISM: Homo sapien

<400> SEQUENCE: 83

Lys Arg Gln Ile Tyr Val Ala Ala Phe
 1               5

<210> SEQ ID NO 84
<211> LENGTH: 9
<212> TYPE: PRT
<213> ORGANISM: Homo sapien

<400> SEQUENCE: 84

Pro Ser Lys Ala Trp Gly Glu Val Lys
 1               5
```

-continued

```
<210> SEQ ID NO 85
<211> LENGTH: 9
<212> TYPE: PRT
<213> ORGANISM: Homo sapien

<400> SEQUENCE: 85

Lys Ala Trp Gly Glu Val Lys Arg Gln
 1               5

<210> SEQ ID NO 86
<211> LENGTH: 9
<212> TYPE: PRT
<213> ORGANISM: Homo sapien

<400> SEQUENCE: 86

Trp Lys Glu Phe Gly Leu Asp Ser Val
 1               5

<210> SEQ ID NO 87
<211> LENGTH: 10
<212> TYPE: PRT
<213> ORGANISM: Homo sapien

<400> SEQUENCE: 87

Gln Trp Lys Glu Phe Gly Leu Asp Ser Val
 1               5                  10

<210> SEQ ID NO 88
<211> LENGTH: 10
<212> TYPE: PRT
<213> ORGANISM: Homo sapien

<400> SEQUENCE: 88

Glu Phe Gly Leu Asp Ser Val Glu Leu Ala
 1               5                  10

<210> SEQ ID NO 89
<211> LENGTH: 91
<212> TYPE: PRT
<213> ORGANISM: Homo sapien

<400> SEQUENCE: 89

Glu Val Pro Gln Leu Thr Asp Leu Ser Phe Val Asp Ile Thr Asp Ser
 1               5                  10                  15

Ser Ile Gly Leu Arg Trp Thr Pro Leu Asn Ser Ser Thr Ile Ile Gly
                20                  25                  30

Tyr Arg Ile Thr Val Val Ala Ala Gly Glu Gly Ile Pro Ile Phe Glu
            35                  40                  45

Asp Phe Val Asp Ser Ser Val Gly Tyr Tyr Thr Val Thr Gly Leu Glu
        50                  55                  60

Pro Gly Ile Asp Tyr Asp Ile Ser Val Ile Thr Leu Ile Asn Gly Gly
 65                  70                  75                  80

Glu Ser Ala Pro Thr Thr Leu Thr Gln Gln Thr
                85                  90

<210> SEQ ID NO 90
<211> LENGTH: 147
<212> TYPE: PRT
<213> ORGANISM: Homo sapien

<400> SEQUENCE: 90

Cys Thr Phe Asp Asn Leu Ser Pro Gly Leu Glu Tyr Asn Val Ser Val
```

```
              1               5              10              15
Tyr Thr Val Lys Asp Asp Lys Glu Ser Val Pro Ile Ser Asp Thr Ile
             20              25              30
Ile Pro Glu Val Pro Gln Leu Thr Asp Leu Ser Phe Val Asp Ile Thr
             35              40              45
Asp Ser Ser Ile Gly Leu Arg Trp Thr Pro Leu Asn Ser Ser Thr Ile
             50              55              60
Ile Gly Tyr Arg Ile Thr Val Val Ala Ala Gly Glu Gly Ile Pro Ile
 65              70              75              80
Phe Glu Asp Phe Val Asp Ser Ser Val Gly Tyr Tyr Thr Val Thr Gly
                 85              90              95
Leu Glu Pro Gly Ile Asp Tyr Asp Ile Ser Val Ile Thr Leu Ile Asn
            100             105             110
Gly Gly Glu Ser Ala Pro Thr Thr Leu Thr Gln Gln Thr Ala Val Pro
            115             120             125
Pro Pro Thr Asp Leu Arg Phe Thr Asn Ile Gly Pro Asp Thr Met Arg
    130             135             140
Val Thr Trp
145

<210> SEQ ID NO 91
<211> LENGTH: 2823
<212> TYPE: DNA
<213> ORGANISM: Homo sapien

<400> SEQUENCE: 91
ctgcactttt gataacctga gtcccggcct ggagtacaat gtcagtgttt acactgtcaa      60
ggatgacaag gaaagtgtcc ctatctctga taccatcatc ccaggtaata gaaaataagc     120
tgctatcctg agagtgacat tccaataaga gtggggatta gcatcttaat ccccagatgc     180
ttaagggtgt caactatatt tgggatttaa ttccgatctc ccagctgcac tttccaaaac     240
caagaagtca agcagcgatt tggacaaaaa tgcttgctgt taacactgct ttactgtctg     300
tgcttcactg ggatgctgtg tgttgcagcg agtatgtaat ggagtggcag ccatggcttt     360
aactctgtat tgtctgctca catggaagta tgactaaaac actgtcacgt gtctgtactc     420
agtactgata ggctcaaagt aatatggtaa atgcatccca tcagtacatt tctgcccgat     480
tttacaatcc atatcaattt ccaacagctg cctatttcat cttgcagttt caaatccttc     540
ttttgaaaa ttgattttta aaaaaagtt aagtaaagt cacaccttca gggttgttct     600
ttcttgtggc cttgaaagac aacattgcaa aggcctgtcc taaggatagg cttgtttgtc     660
cattgggtta aacataatg aaagcattgg acagatcgtg tcccccttg gactcttcag     720
tagaatgctt ttactaacgc taattacatg ttttgattat gaatgaacct aaaatagtgg     780
caatggcctt aacctaggcc tgtctttcct cagcctgaat gtgcttttga atggcacatt     840
tcacaccata cattcataat gcattagcgt tatggccatg atgttgtcat gagttttgta     900
tgggagaaaa aaaatcaatt tatcacccat ttattatttt ttccggttgt tcatgcaagc     960
ttatttttcta ctaaaacagt tttggaatta ttaaaagcat tgctgatact tacttcagat    1020
attatgtcta ggctctaaga atggtttcga catcctaaac agccatatga ttttaggaa     1080
tctgaacagt tcaaattgta ccctttaagg atgttttcaa aatgtaaaaa atatatatat    1140
atatatat tccctaaaag aatattcctg tttattcttc tagggaagca aactgttcat    1200
gatgcttagg aagtcttttc agagaattta aaacagattg catattacca tcattgcttt    1260
```

-continued

```
aacattccac caattttact actagtaacc tgatatacac tgcttttattt tttcctcttt      1320 ttttccctct attttccttt tgcctccccc tcccttttgct ttgtaactca atagaggtgc      1380
cccaactcac tgacctaagc tttgttgata taaccgattc aagcatcggc ctgaggtgga      1440
ccccgctaaa ctcttccacc attattgggt accgcatcac agtagttgcg gcaggagaag      1500
gtatccctat ttttgaagat tttgtggact cctcagtagg atactacaca gtcacagggc      1560
tggagccggg cattgactat gatatcagcg ttatcactct cattaatggc ggcgagagtg      1620
cccctactac actgacacaa caaacgggtg aattttgaaa acttctgcgt ttgagacata      1680
gatggtgttg catgctgcca ccagttactc cggttaaata tggatgtttc atgggggaag      1740
tcagcaattg gccaaagatt cagataggtg gaattggggg gataaggaat caaatgcatc      1800
tgctaaactg attggagaaa aacacatgca atatcttcag tacactctca tttaaaccac      1860
aagtagatat aaagcctaga gaaatacaga tgtctgctct gttaaatata aaatagcaaa      1920
tgttcattca atttgaagac ctagaatttt tcttcttaaa taccaaacac gaataccaaa      1980
ttgcgtaagt accaattgat aagaatatat caccaaaatg taccatcatg ctcttccttc      2040 tacccttga taaactctac catgctcctt ctttgtagct aaaaacccat caaaatttag      2100
ggtagagtgg atgggcattg ttttgaggta ggagaaaagt aaacttggga ccattctagg      2160
ttttgttgct gtcactaggt aaagaaacac ctctttaacc acagtctggg acaagcatg      2220 caacatttta aggttctct gctgtgcatg ggaaaagaaa catgctgaga accaatttgc      2280
atgaacatgt tcacttgtaa gtagaattca ctgaatggaa ctgtagctct agatatctca      2340
catgggggga agtttaggac cctcttgtct ttttgtctgt gtgcatgtat ttctttgtaa      2400
agtactgcta tgtttctctt tgctgtgtgg caacttaagc ctcttcggcc tgggataaaa      2460
taatctgcag tggtattaat aatgtacata aagtcaacat atttgaaagt agattaaaat      2520
cttttttaaa tatatcaatg atggcaaaaa ggttaaaggg ggcctaacag tactgtgtgt      2580
agtgttttat ttttaacagt agtacactat aacttaaaat agacttagat tagactgttt      2640
gcatgattat gattctgttt cctttatgca tgaaatattg attttacctt tccagctact      2700
tcgttagctt taattttaaa atacattaac tgagtcttcc ttcttgttcg aaaccagctg      2760
ttcctcctcc cactgacctg cgattcacca acattggtcc agacaccatg cgtgtcacct      2820
ggg                                                                    2823
```

<210> SEQ ID NO 92
<211> LENGTH: 9
<212> TYPE: PRT
<213> ORGANISM: Homo sapien

<400> SEQUENCE: 92

Thr Ile Ile Pro Glu Val Pro Gln Leu
 1               5

<210> SEQ ID NO 93
<211> LENGTH: 10
<212> TYPE: PRT
<213> ORGANISM: Homo sapien

<400> SEQUENCE: 93

Asp Thr Ile Ile Pro Glu Val Pro Gln Leu
 1               5                  10

<210> SEQ ID NO 94
<211> LENGTH: 10

<212> TYPE: PRT
<213> ORGANISM: Homo sapien

<400> SEQUENCE: 94

Glu Val Pro Gln Leu Thr Asp Leu Ser Phe
1               5                   10

<210> SEQ ID NO 95
<211> LENGTH: 8
<212> TYPE: PRT
<213> ORGANISM: Homo sapien

<400> SEQUENCE: 95

Thr Pro Leu Asn Ser Ser Thr Ile
1               5

<210> SEQ ID NO 96
<211> LENGTH: 8
<212> TYPE: PRT
<213> ORGANISM: Homo sapien

<400> SEQUENCE: 96

Ile Gly Leu Arg Trp Thr Pro Leu
1               5

<210> SEQ ID NO 97
<211> LENGTH: 9
<212> TYPE: PRT
<213> ORGANISM: Homo sapien

<400> SEQUENCE: 97

Ser Ile Gly Leu Arg Trp Thr Pro Leu
1               5

<210> SEQ ID NO 98
<211> LENGTH: 9
<212> TYPE: PRT
<213> ORGANISM: Homo sapien

<400> SEQUENCE: 98

Leu Asn Ser Ser Thr Ile Ile Gly Tyr
1               5

<210> SEQ ID NO 99
<211> LENGTH: 10
<212> TYPE: PRT
<213> ORGANISM: Homo sapien

<400> SEQUENCE: 99

Pro Leu Asn Ser Ser Thr Ile Ile Gly Tyr
1               5                   10

<210> SEQ ID NO 100
<211> LENGTH: 9
<212> TYPE: PRT
<213> ORGANISM: Homo sapien

<400> SEQUENCE: 100

Thr Pro Leu Asn Ser Ser Thr Ile Ile
1               5

<210> SEQ ID NO 101
<211> LENGTH: 8
<212> TYPE: PRT
<213> ORGANISM: Homo sapien

```
<400> SEQUENCE: 101

Ile Gly Tyr Arg Ile Thr Val Val
1               5

<210> SEQ ID NO 102
<211> LENGTH: 9
<212> TYPE: PRT
<213> ORGANISM: Homo sapien

<400> SEQUENCE: 102

Ile Ile Gly Tyr Arg Ile Thr Val Val
1               5

<210> SEQ ID NO 103
<211> LENGTH: 10
<212> TYPE: PRT
<213> ORGANISM: Homo sapien

<400> SEQUENCE: 103

Thr Ile Ile Gly Tyr Arg Ile Thr Val Val
1               5                   10

<210> SEQ ID NO 104
<211> LENGTH: 9
<212> TYPE: PRT
<213> ORGANISM: Homo sapien

<400> SEQUENCE: 104

Ile Gly Tyr Arg Ile Thr Val Val Ala
1               5

<210> SEQ ID NO 105
<211> LENGTH: 10
<212> TYPE: PRT
<213> ORGANISM: Homo sapien

<400> SEQUENCE: 105

Ile Ile Gly Tyr Arg Ile Thr Val Val Ala
1               5                   10

<210> SEQ ID NO 106
<211> LENGTH: 10
<212> TYPE: PRT
<213> ORGANISM: Homo sapien

<400> SEQUENCE: 106

Glu Leu Ala Gly Ile Gly Ile Leu Thr Val
1               5                   10

<210> SEQ ID NO 107
<211> LENGTH: 10
<212> TYPE: PRT
<213> ORGANISM: Homo sapien

<400> SEQUENCE: 107

Glu Ala Ala Gly Ile Gly Ile Leu Thr Val
1               5                   10

<210> SEQ ID NO 108
<211> LENGTH: 10
<212> TYPE: PRT
<213> ORGANISM: Homo sapien

<400> SEQUENCE: 108
```

```
Phe Leu Pro Ser Asp Tyr Phe Pro Ser Val
1               5                   10
```

<210> SEQ ID NO 109
<211> LENGTH: 9
<212> TYPE: PRT
<213> ORGANISM: Homo sapien

<400> SEQUENCE: 109

```
Ala Glu Met Gly Lys Tyr Ser Phe Tyr
1               5
```

<210> SEQ ID NO 110
<211> LENGTH: 15
<212> TYPE: PRT
<213> ORGANISM: Homo sapien

<400> SEQUENCE: 110

```
Ala Phe Ser Pro Gln Gly Met Pro Glu Gly Asp Leu Val Tyr Val
1               5                   10                  15
```

<210> SEQ ID NO 111
<211> LENGTH: 12
<212> TYPE: PRT
<213> ORGANISM: Homo sapien

<400> SEQUENCE: 111

```
Asn Tyr Ala Arg Thr Glu Asp Phe Phe Lys Leu Glu
1               5                   10
```

<210> SEQ ID NO 112
<211> LENGTH: 20
<212> TYPE: PRT
<213> ORGANISM: Homo sapien

<400> SEQUENCE: 112

```
Pro Glu Gly Asp Leu Val Tyr Val Asn Tyr Ala Arg Thr Glu Asp Phe
1               5                   10                  15
Phe Lys Leu Glu
            20
```

<210> SEQ ID NO 113
<211> LENGTH: 14
<212> TYPE: PRT
<213> ORGANISM: Homo sapien

<400> SEQUENCE: 113

```
Asn Tyr Ala Arg Thr Glu Asp Phe Phe Lys Leu Glu Arg Asp
1               5                   10
```

<210> SEQ ID NO 114
<211> LENGTH: 22
<212> TYPE: PRT
<213> ORGANISM: Homo sapien

<400> SEQUENCE: 114

```
Pro Glu Gly Asp Leu Val Tyr Val Asn Tyr Ala Arg Thr Glu Asp Phe
1               5                   10                  15
Phe Lys Leu Glu Arg Asp
            20
```

<210> SEQ ID NO 115
<211> LENGTH: 15

```
<212> TYPE: PRT
<213> ORGANISM: Homo sapien

<400> SEQUENCE: 115

Asn Tyr Ala Arg Thr Glu Asp Phe Phe Lys Leu Glu Arg Asp Met
 1               5                  10                  15

<210> SEQ ID NO 116
<211> LENGTH: 14
<212> TYPE: PRT
<213> ORGANISM: Homo sapien

<400> SEQUENCE: 116

Ala Phe Ser Pro Gln Gly Met Pro Glu Gly Asp Leu Val Tyr
 1               5                  10

<210> SEQ ID NO 117
<211> LENGTH: 16
<212> TYPE: PRT
<213> ORGANISM: Homo sapien

<400> SEQUENCE: 117

Val Asn Tyr Ala Arg Thr Glu Asp Phe Phe Lys Leu Glu Arg Asp Met
 1               5                  10                  15

<210> SEQ ID NO 118
<211> LENGTH: 17
<212> TYPE: PRT
<213> ORGANISM: Homo sapien

<400> SEQUENCE: 118

Ala Phe Ser Pro Gln Gly Met Pro Glu Gly Asp Leu Val Tyr Val Asn
 1               5                  10                  15

Tyr

<210> SEQ ID NO 119
<211> LENGTH: 13
<212> TYPE: PRT
<213> ORGANISM: Homo sapien

<400> SEQUENCE: 119

Ala Arg Thr Glu Asp Phe Phe Lys Leu Glu Arg Asp Met
 1               5                  10

<210> SEQ ID NO 120
<211> LENGTH: 21
<212> TYPE: PRT
<213> ORGANISM: Homo sapien

<400> SEQUENCE: 120

Ala Phe Ser Pro Gln Gly Met Pro Glu Gly Asp Leu Val Tyr Val Asn
 1               5                  10                  15

Tyr Ala Arg Thr Glu
                20

<210> SEQ ID NO 121
<211> LENGTH: 9
<212> TYPE: PRT
<213> ORGANISM: Homo sapien

<400> SEQUENCE: 121

Asp Phe Phe Lys Leu Glu Arg Asp Met
 1               5
```

<210> SEQ ID NO 122
<211> LENGTH: 17
<212> TYPE: PRT
<213> ORGANISM: Homo sapien

<400> SEQUENCE: 122

Tyr Val Asn Tyr Ala Arg Thr Glu Asp Phe Phe Lys Leu Glu Arg Asp
 1               5                  10                  15
Met

<210> SEQ ID NO 123
<211> LENGTH: 19
<212> TYPE: PRT
<213> ORGANISM: Homo sapien

<400> SEQUENCE: 123

Gln Gly Met Pro Glu Gly Asp Leu Val Tyr Val Asn Tyr Ala Arg Thr
 1               5                  10                  15
Glu Asp Phe

<210> SEQ ID NO 124
<211> LENGTH: 9
<212> TYPE: PRT
<213> ORGANISM: Homo sapien

<400> SEQUENCE: 124

Asn Tyr Ala Arg Thr Glu Asp Phe Phe
 1               5

<210> SEQ ID NO 125
<211> LENGTH: 17
<212> TYPE: PRT
<213> ORGANISM: Homo sapien

<400> SEQUENCE: 125

Arg Gly Ile Ala Glu Ala Val Gly Leu Pro Ser Ile Pro Val His Pro
 1               5                  10                  15
Ile

<210> SEQ ID NO 126
<211> LENGTH: 12
<212> TYPE: PRT
<213> ORGANISM: Homo sapien

<400> SEQUENCE: 126

Ala Val Gly Leu Pro Ser Ile Pro Val His Pro Ile
 1               5                  10

<210> SEQ ID NO 127
<211> LENGTH: 11
<212> TYPE: PRT
<213> ORGANISM: Homo sapien

<400> SEQUENCE: 127

Val Gly Leu Pro Ser Ile Pro Val His Pro Ile
 1               5                  10

<210> SEQ ID NO 128
<211> LENGTH: 10
<212> TYPE: PRT
<213> ORGANISM: Homo sapien

<400> SEQUENCE: 128

Gly Leu Pro Ser Ile Pro Val His Pro Ile
1               5                   10

<210> SEQ ID NO 129
<211> LENGTH: 13
<212> TYPE: PRT
<213> ORGANISM: Homo sapien

<400> SEQUENCE: 129

Gly Tyr Tyr Asp Ala Gln Lys Leu Leu Glu Lys Met Gly
1               5                   10

<210> SEQ ID NO 130
<211> LENGTH: 8
<212> TYPE: PRT
<213> ORGANISM: Homo sapien

<400> SEQUENCE: 130

Gly Tyr Tyr Asp Ala Gln Lys Leu
1               5

<210> SEQ ID NO 131
<211> LENGTH: 25
<212> TYPE: PRT
<213> ORGANISM: Homo sapien

<400> SEQUENCE: 131

Arg Gly Ile Ala Glu Ala Val Gly Leu Pro Ser Ile Pro Val His Pro
1               5                   10                  15

Ile Gly Tyr Tyr Asp Ala Gln Lys Leu
            20                  25

<210> SEQ ID NO 132
<211> LENGTH: 27
<212> TYPE: PRT
<213> ORGANISM: Homo sapien

<400> SEQUENCE: 132

Arg Gly Ile Ala Glu Ala Val Gly Leu Pro Ser Ile Pro Val His Pro
1               5                   10                  15

Ile Gly Tyr Tyr Asp Ala Gln Lys Leu Leu Glu
            20                  25

<210> SEQ ID NO 133
<211> LENGTH: 22
<212> TYPE: PRT
<213> ORGANISM: Homo sapien

<400> SEQUENCE: 133

Ala Val Gly Leu Pro Ser Ile Pro Val His Pro Ile Gly Tyr Tyr Asp
1               5                   10                  15

Ala Gln Lys Leu Leu Glu
            20

<210> SEQ ID NO 134
<211> LENGTH: 21
<212> TYPE: PRT
<213> ORGANISM: Homo sapien

<400> SEQUENCE: 134

Val Gly Leu Pro Ser Ile Pro Val His Pro Ile Gly Tyr Tyr Asp Ala
1               5                   10                  15

-continued

```
Gln Lys Leu Leu Glu
         20

<210> SEQ ID NO 135
<211> LENGTH: 20
<212> TYPE: PRT
<213> ORGANISM: Homo sapien

<400> SEQUENCE: 135

Gly Leu Pro Ser Ile Pro Val His Pro Ile Gly Tyr Tyr Asp Ala Gln
 1               5                  10                  15

Lys Leu Leu Glu
         20

<210> SEQ ID NO 136
<211> LENGTH: 19
<212> TYPE: PRT
<213> ORGANISM: Homo sapien

<400> SEQUENCE: 136

Arg Gly Ile Ala Glu Ala Val Gly Leu Pro Ser Ile Pro Val His Pro
 1               5                  10                  15

Ile Gly Tyr

<210> SEQ ID NO 137
<211> LENGTH: 14
<212> TYPE: PRT
<213> ORGANISM: Homo sapien

<400> SEQUENCE: 137

Ala Val Gly Leu Pro Ser Ile Pro Val His Pro Ile Gly Tyr
 1               5                  10

<210> SEQ ID NO 138
<211> LENGTH: 13
<212> TYPE: PRT
<213> ORGANISM: Homo sapien

<400> SEQUENCE: 138

Val Gly Leu Pro Ser Ile Pro Val His Pro Ile Gly Tyr
 1               5                  10

<210> SEQ ID NO 139
<211> LENGTH: 12
<212> TYPE: PRT
<213> ORGANISM: Homo sapien

<400> SEQUENCE: 139

Gly Leu Pro Ser Ile Pro Val His Pro Ile Gly Tyr
 1               5                  10

<210> SEQ ID NO 140
<211> LENGTH: 24
<212> TYPE: PRT
<213> ORGANISM: Homo sapien

<400> SEQUENCE: 140

Val Gly Leu Pro Ser Ile Pro Val His Pro Ile Gly Tyr Tyr Asp Ala
 1               5                  10                  15

Gln Lys Leu Leu Glu Lys Met Gly
         20

<210> SEQ ID NO 141
```

```
<211> LENGTH: 23
<212> TYPE: PRT
<213> ORGANISM: Homo sapien

<400> SEQUENCE: 141

Gly Leu Pro Ser Ile Pro Val His Pro Ile Gly Tyr Tyr Asp Ala Gln
 1               5                  10                  15

Lys Leu Leu Glu Lys Met Gly
            20

<210> SEQ ID NO 142
<211> LENGTH: 11
<212> TYPE: PRT
<213> ORGANISM: Homo sapien

<400> SEQUENCE: 142

Ser Ser Ile Glu Gly Asn Tyr Thr Leu Arg Val
 1               5                  10

<210> SEQ ID NO 143
<211> LENGTH: 16
<212> TYPE: PRT
<213> ORGANISM: Homo sapien

<400> SEQUENCE: 143

Ser Ser Ile Glu Gly Asn Tyr Thr Leu Arg Val Asp Cys Thr Pro Leu
 1               5                  10                  15

<210> SEQ ID NO 144
<211> LENGTH: 17
<212> TYPE: PRT
<213> ORGANISM: Homo sapien

<400> SEQUENCE: 144

Ser Ser Ile Glu Gly Asn Tyr Thr Leu Arg Val Asp Cys Thr Pro Leu
 1               5                  10                  15

Met

<210> SEQ ID NO 145
<211> LENGTH: 9
<212> TYPE: PRT
<213> ORGANISM: Homo sapien

<400> SEQUENCE: 145

Arg Val Asp Cys Thr Pro Leu Met Tyr
 1               5

<210> SEQ ID NO 146
<211> LENGTH: 18
<212> TYPE: PRT
<213> ORGANISM: Homo sapien

<400> SEQUENCE: 146

Ser Ser Ile Glu Gly Asn Tyr Thr Leu Arg Val Asp Cys Thr Pro Leu
 1               5                  10                  15

Met Tyr

<210> SEQ ID NO 147
<211> LENGTH: 10
<212> TYPE: PRT
<213> ORGANISM: Homo sapien

<400> SEQUENCE: 147
```

Ser Leu Val His Asn Leu Thr Lys Glu Leu
1               5                   10

<210> SEQ ID NO 148
<211> LENGTH: 12
<212> TYPE: PRT
<213> ORGANISM: Homo sapien

<400> SEQUENCE: 148

Met Tyr Ser Leu Val His Asn Leu Thr Lys Glu Leu
1               5                   10

<210> SEQ ID NO 149
<211> LENGTH: 7
<212> TYPE: PRT
<213> ORGANISM: Homo sapien

<400> SEQUENCE: 149

Leu Pro Asp Arg Pro Phe Tyr
1               5

<210> SEQ ID NO 150
<211> LENGTH: 11
<212> TYPE: PRT
<213> ORGANISM: Homo sapien

<400> SEQUENCE: 150

Asp Pro Leu Gly Leu Pro Asp Arg Pro Phe Tyr
1               5                   10

<210> SEQ ID NO 151
<211> LENGTH: 12
<212> TYPE: PRT
<213> ORGANISM: Homo sapien

<400> SEQUENCE: 151

Ile Asp Pro Leu Gly Leu Pro Asp Arg Pro Phe Tyr
1               5                   10

<210> SEQ ID NO 152
<211> LENGTH: 13
<212> TYPE: PRT
<213> ORGANISM: Homo sapien

<400> SEQUENCE: 152

Phe Ile Asp Pro Leu Gly Leu Pro Asp Arg Pro Phe Tyr
1               5                   10

<210> SEQ ID NO 153
<211> LENGTH: 14
<212> TYPE: PRT
<213> ORGANISM: Homo sapien

<400> SEQUENCE: 153

Ala Phe Ile Asp Pro Leu Gly Leu Pro Asp Arg Pro Phe Tyr
1               5                   10

<210> SEQ ID NO 154
<211> LENGTH: 15
<212> TYPE: PRT
<213> ORGANISM: Homo sapien

<400> SEQUENCE: 154

Arg Ala Phe Ile Asp Pro Leu Gly Leu Pro Asp Arg Pro Phe Tyr
1               5                   10                  15

```
<210> SEQ ID NO 155
<211> LENGTH: 20
<212> TYPE: PRT
<213> ORGANISM: Homo sapien

<400> SEQUENCE: 155

Phe Asp Lys Ser Asn Pro Ile Val Leu Arg Met Met Asn Asp Gln Leu
 1               5                  10                  15

Met Phe Leu Glu
            20

<210> SEQ ID NO 156
<211> LENGTH: 16
<212> TYPE: PRT
<213> ORGANISM: Homo sapien

<400> SEQUENCE: 156

Glu Arg Ala Phe Ile Asp Pro Leu Gly Leu Pro Asp Arg Pro Phe Tyr
 1               5                  10                  15

<210> SEQ ID NO 157
<211> LENGTH: 19
<212> TYPE: PRT
<213> ORGANISM: Homo sapien

<400> SEQUENCE: 157

Phe Asp Lys Ser Asn Pro Ile Val Leu Arg Met Met Asn Asp Gln Leu
 1               5                  10                  15

Met Phe Leu

<210> SEQ ID NO 158
<211> LENGTH: 17
<212> TYPE: PRT
<213> ORGANISM: Homo sapien

<400> SEQUENCE: 158

Leu Glu Arg Ala Phe Ile Asp Pro Leu Gly Leu Pro Asp Arg Pro Phe
 1               5                  10                  15

Tyr

<210> SEQ ID NO 159
<211> LENGTH: 18
<212> TYPE: PRT
<213> ORGANISM: Homo sapien

<400> SEQUENCE: 159

Phe Asp Lys Ser Asn Pro Ile Val Leu Arg Met Met Asn Asp Gln Leu
 1               5                  10                  15

Met Phe
```

ANTI-NEOVASCULATURE PREPARATIONS FOR CANCER

CROSS REFERENCE

This application claims priority under 35 U.S.C. § 119(e) to U.S. Provisional Patent Application Ser. No. 60/274,063, filed on Mar. 7, 2001, entitled "ANTI-NEOVASCULATURE PREPARATIONS FOR CANCER," which is hereby incorporated by reference in its entirety.

BACKGROUND OF THE INVENTION

Description of the Related Art

The treatment of cancer has remained challenging despite the advances in biomedicine. In recent years two approaches have been described showing much promise: therapeutic vaccines and anti-angiogenesis.

Therapeutic vaccines rely on the observation that cancerous tissues generally express certain antigens preferentially, collectively tumor-associated antigens (TuAA). TuAA include proteins normally expressed selectively by the tissue from which the cancer derives (differentiation antigens), proteins that are associated with a different stage of development (oncofetal and cancer-testis antigens), proteins that are created by aberrant chromosomal rearrangement, or proteins that are derived from oncogenic viruses. These TuAA, or fragments of them, are then used as immunogens in vaccines intended to stimulate cellular immunity, particularly cytotoxic T lymphocytes (CTL), capable of killing the tumor cells.

The anti-angiogenesis approach takes advantage of the need of tumors to recruit a blood supply to support their continued growth. To accomplish this, tumors secrete angiogenic factors that promote the growth of new blood vessels. The anti-angiogenesis approach aims to disrupt a tumor's supply of nutrients to cause it to die, or at least limit its growth. Attempts at this approach have sought chemotherapeutic drugs used directly against a variety of anti-angiogenic factors and angiogenesis.

SUMMARY OF THE INVENTION

The invention disclosed herein is directed to compositions designed to stimulate cellular immune responses targeting tumor-associated neovasculature (TuNV). In one embodiment of the invention the compositions stimulate a CTL response. Such compositions may include one or more epitopes of the target antigen. One aspect of this embodiment specifically includes a housekeeping epitope, another specifically includes an immune epitope or epitope cluster, and another aspect specifically combines housekeeping and immune epitopes.

Embodiments of the invention relate to the use of prostate specific membrane antigen (PSMA) as the target antigen of the composition. Aspects of this embodiment include various epitopes derived from PSMA provided directly as polypeptide, or as a nucleic acid capable of conferring expression of the epitope. Other embodiments relate to the use of other TuNV-associated antigens.

In other embodiments of the invention, compositions are directed against both the TuNV and against TuAA expressed by the cancerous cells, by combining immunogens derived from both sources into a single formulation or method or treatment.

Preclinical evaluation of the compositions of this invention can be accomplished using adoptive transfer of immunized T cells into SCID mice bearing microvasculature formed from implanted human dermal microvascular endothelial cells (HDMEC). Preclinical evaluation can also be accomplished through the use of HLA-transgenic mice immunized with compositions comprised of epitopes conserved between mice and humans.

Embodiments of the invention relate to methods of evaluating cell-mediated immunity. The methods can include the steps of implanting vascular cells into an immunodeficient mammal; establishing an immune response in the mammal; and assaying a characteristic to determine cell-mediated immunity in the mammal. The cell-mediated immunity can be directed against a neovasculature antigen, for example. The neovasculature antigen can be preferentially expressed by tumor-associated neovasculature, for example, and in preferred embodiments can be prostate specific membrane antigen (PSMA), vascular endothelial growth factor receptor 2 (VEGFR2), and the like. The establishing step can be achieved, for example, by adoptive transfer of T-cells to the mammal, by contacting the mammal with an antigen, and the like. The cell-mediated immunity can be mediated by cytotoxic T lymphocytes. The vascular cells can be vascular endothelial cells, such as, for example, human dermal microvascular endothelial cells (HDMEC), telomerase-transformed endothelial cells, and the like. The immunodeficient mammal can be a mouse, such as for example a SCID mouse. The characterizing step can include assessing a parameter, such as for example, vessel formation, vessel destruction, vessel density, proportion of vessels carrying blood of the host mammal, and the like.

The methods can further include the step of implanting tumor cells or tumor tissue in the mouse. The characterizing step can include assessing a parameter, such as, for example, tumor presence, tumor growth, tumor size, rapidity of tumor appearance, dose of vaccine required to inhibit or prevent tumor establishment, tumor vascularization, a proportion of necrotic tissue within the tumor, and the like.

The methods can further include the steps of providing a first population of mammals and a second populations of mammals; establishing cell-mediated immunity in the first population; differentially establishing cell-mediated immunity in the second population; and comparing a result obtained from the first population of mammals to a result obtained from the second population of mammals. The cell-mediated immunity of the first population can include, for example, naive immunity, immunity to an irrelevant epitope, and the like.

Other embodiments relate to methods of evaluating cell-mediated immunity, including immunity directed against a neovasculature antigen. The methods can include the steps of implanting or injecting MHC-transgenic tumor cells into an MHC-transgenic mammal; establishing an immune response in the mammal; and assaying a characteristic to determine cell-mediated immunity in the mammal. The MHC-transgenic mammal can be an HLA-transgenic mammal, such as, for example an HLA-A2 transgenic mammal. In preferred embodiments the mammal can be a mouse. The cell-mediated immunity can be established by vaccination, which in preferred embodiments can take place prior to, concurrent with, or subsequent to transfer of the tumor cells, for example. In preferred embodiments the cell-mediated immunity can be mediated by cytotoxic T lymphocytes. The neovasculature antigen can be preferentially expressed by tumor-associated neovasculature and can also be a tumor-associated antigen. Preferably, the antigen can be the ED-B domain of fibronectin. The characterizing step can include, for example, assessing a parameter, including tumor presence, tumor growth, tumor size, rapidity of tumor appearance, dose of vaccine required to inhibit or prevent tumor establishment, tumor vascularization, a proportion of necrotic tissue within the tumor, and the like. The methods can further include the steps of providing a first population of mammals and a second populations of mammals; establishing cell-mediated immunity in the first population; differentially establishing cell-mediated immunity in the second population; and comparing a result obtained from the first population of mammals to a result obtained from the second population of mammals. The cell-mediated immunity of the first population can include naïve immunity, immunity to an irrelevant epitope, and the like.

Still further embodiments relate to methods of treating neoplastic disease, including the step of immunizing a mammal to induce a cellular immune response directed against an antigen differentially expressed by tumor-associated neovasculature. The differentially expressed antigen can be a protein, such as, for example prostate specific membrane antigen, vascular endothelial growth factor receptor 2 (VEGFR2), and the like. In other preferred embodiments, the antigen can be the ED-B domain of fibronectin. The immunization can be carried out, for example, with at least one peptide derived from the sequence of the protein, with a nucleic acid capable of conferring expression of the protein or peptides, and the like. The at least one peptide can include a housekeeping epitope, for example, and in preferred embodiments can be co-C-terminal with the housekeeping epitope. The methods can further include at least one additional peptide, wherein the at least one additional peptide includes an immune epitope. The methods can include an additional step wherein the mammal is treated with an anti-tumor therapy active directly against cancerous cells. The anti-tumor therapy can be immunization against a tumor-associated antigen. Preferably, the cellular immune response can include a CTL response.

Other embodiments relate to immunogenic compositions. The immunogenic compositions can include at least one immunogen corresponding to an antigen expressed by tumor-associated neovasculature, wherein the composition can induce a cellular immune response. The immunogen can be one that is not associated with a cell conspecific with the recipient. The antigen can be a protein, such as, for example prostate specific membrane antigen, vascular endothelial growth factor receptor 2 (VEGFR2), and the like. In other preferred embodiments the antigen can be the ED-B domain of fibronectin. The immunogen can include at least one peptide. The compositions can include a nucleic acid capable of conferring expression of the antigen, and wherein the antigen is a protein or a peptide. The compositions can include at least one peptide that includes a housekeeping epitope, and in preferred embodiments the at least one peptide can be co-C-terminal with the housekeeping epitope. Also, the compositions can additionally include at least one peptide that includes an immune epitope. The compositions can include at least one immunogen corresponding to a tumor-associated antigen. In preferred embodiments the cellular immune response can include a CTL response.

Embodiments relate to methods of anti-tumor vaccine design. The methods can include the steps of identifying an antigen differentially expressed by tumor-associated neovasculature; and incorporating a component of the antigen into a vaccine. The component can include, for example, a polypeptide fragment of the antigen, a nucleic acid encoding the antigen or a fragment of the antigen, and the like.

Further embodiments relate to methods of making a research model. The methods can include implanting a vascular cell and a tumor cell into an immunodeficient mammal. The tumor cell and the vascular cell can be implanted adjacent to one another. The vascular cell can be a vascular endothelial cell, such as for example HDMEC. In preferred embodiments the vascular endothelial cell can be telomerase-transformed. The immunodeficient mammal can be a mouse, such as, for example, a SCID mouse.

Other embodiments relate to research models. The research models can include an immunodeficient mammal. The mammal can include an implanted vascular cell and an implanted tumor cell. The vascular cell and the tumor cell can be implanted adjacent to one another.

BRIEF DESCRIPTION OF THE DRAWINGS

FIG. 9 shows epitope specific lysis by CTL from HHD-A2 mice immunized with ED-B 29-38 peptide.

DETAILED DESCRIPTION OF THE PREFERRED EMBODIMENT

Figure 1B:
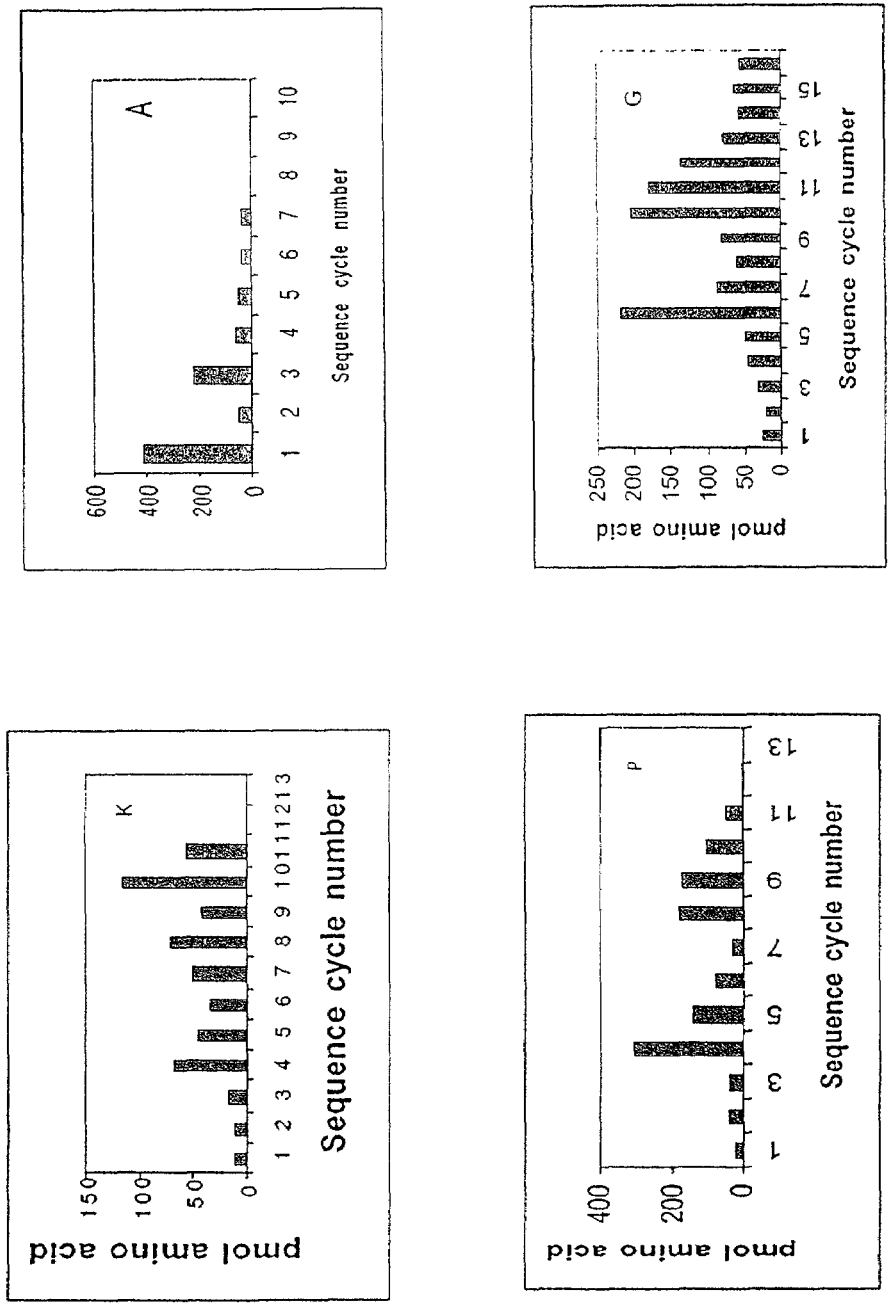
FIGS. 1A, B, and C show results of N-terminal pool sequencing of a T=60 min. time point aliquot of the $PSMA_{163-192}$ proteasomal digest.

Embodiments of the invention disclosed herein provide compositions, methods of composition or vaccine design, and methods of treatment related to the generation of a cellular immune response, preferably, a T cell response and, more preferably, a CTL response, directed against the neovasculature of tumors. Such methods and compositions are particularly useful in the treatment and prevention of cancer. Other embodiments relate to composition evaluation models.

Compositions, Composition Design, and Treatment Using the Compositions

Embodiments of the invention relate to immunogenic compositions, including vaccines, for the generation of a cellular immune response, particularly a T cell response and specifically a CTL response, directed against tumor neovasculature (TuNV). "Tumor neovasculature" is broadly meant to include any vasculature found in or around tumor masses, vasculature which supports or is necessary for tumor growth, and the like. It should be noted, and one of skill in the art will appreciate, that although the discussion herein refers generally to the tumors and tumor neovasculature, the embodiments of the present invention also can be applied to other conditions or disease states associated with inappropriate angiogenesis.

Until now the design of anti-tumor vaccines has concentrated on antigens expressed by the malignant cells themselves. However, larger tumors are complex structures and not simply a homogeneous mass of cells. All cells, particularly rapidly growing cells, need a supply of nutrients (oxygen, glucose, amino acids, etc.), as well as a means of removal of metabolic wastes, in order to remain metabolically active and intact. This is normally accomplished by the flow of blood and lymph through the various organs of the body. At a cellular level, the tissues of the body are permeated by a fine network of capillaries—tiny vessels through which nutrients and waste products can be exchanged with the surrounding cells by diffusion. Diffusion is effective over relatively short distances. The capillary beds are so extensive that generally cells are at most located only a few cells away from a capillary. If a tumor merely grew by propagation of its malignant cells, soon those cells in the interior of the mass would be unable to sustain themselves. In fact, the interiors of unvascularized tumors often contain necrotic tissue. Thus, in order to grow unchecked, tumors secrete factors that promote the in-growth of new blood vessels, namely TuNV. Since the TuNV expresses antigens differentiating it from other tissues, cancer can be treated with therapeutic compositions directed against the TuNV, instead of directly targeting the cancerous cells themselves. Suitable TuNV antigens can include those that are expressed generally in neovasculature or preferentially by TuNV, for example.

In some embodiments of the invention the compositions can include, for example, an epitopic peptide or peptides. Immune epitopes may be provided embedded in epitope clusters and protein fragments. Housekeeping epitopes can be provided with the proper C-terminus. In other embodiments of the invention the compositions can include nucleic acids capable of conferring expression of these epitopes on pAPC, for example.

In preferred embodiments, the compositions can be administered directly to the lymphatic system of a mammal being treated. This can be applied to both polypeptide and nucleic acid based compositions. Administration methods of this type, and related technologies, are disclosed in U.S. patent application Ser. No. 09/380,534, filed on Sep. 1, 1999, and a Continuation-in-Part thereof, filed on Feb. 2, 2001; U.S. patent application Ser. No. 09/776,232, both entitled "A METHOD OF INDUCING A CTL RESPONSE," which are incorporated by reference in their entirety.

In a preferred embodiment, destruction of the blood vessels in a tumor by action of a composition of the invention can eliminate all of the cells in a tumor. However, small tumors, including micrometastases, are typically unvasculaturized. Additionally, unvascularized tumors that instead apparently rely on blood flow through channels penetrating the tumor mass have been reported (Maniotis, A. J., et al. Am. J. Pathol. 155: 739-752, 1999). Thus in other embodiments, the compositions are generally effective as tumor control agents that may not eradicate all cancer cells. Accordingly, the invention provides tools for eliminating tumors, controlling tumor growth, reducing tumor burden, improving overall clinical status, and the like. In some embodiments, it can be desirable to combine these compositions with other treatments that target the cancerous cells directly. Additionally there is evidence that the vasculature in tumors can be mosaic in nature consisting of both endothelial and cancer cells (Chang, Y. S., et al. Proc. Natl. Acad. Sci. USA 97:14608-14613, 2000). Thus, in some embodiments of the invention a course of composition treatment can be followed by administration of a bio- or chemotherapeutic agent. In a particularly preferred embodiment, treatment can include administration of a TuAA directed composition concurrent or subsequent to administration of the anti-TuNV composition.

As mentioned above, suitable TuNV antigens for the compositions can include those that are expressed generally in neovasculature or preferentially by TuNV, for example. A variety of techniques for discovery of TuAA are known in the art. Examples of these techniques include, without limitation, differential hybridization and subtractive hybridization, including use of microarrays; expression cloning; SAGE (serial analysis of gene expression); SEREX (serological identification of antigens by recombinant expression cloning); in situ RT-PCT; immunohistochemistry (as was the case for PSMA); EST analysis; variously using bulk, sectioned, and/or microdissected tissue; and the like. Utilization of these and other methods provides one of skill in the art the techniques necessary to identify genes and gene products contained within a target cell that may be used as antigens of immunogenic compositions. The techniques are applicable to TuAA discovery regardless of whether the target cell is a cancer cell or an endothelial cell. Any identified antigen can be scrutinized for epitopes, which can be used in embodiments of the invention.

The endothelial cells making up the lining of the vasculature can express housekeeping proteasomes. Thus, compositions targeting endothelial cells can be comprised of peptides, or nucleic acids conferring expression of the peptides, corresponding to the digestion products of the housekeeping proteasome (i.e. housekeeping epitopes). IFN-γ (gamma), secreted by activated cells of the immune system, can induce expression of the immunoproteasome in the target cells. Generally, the immunoproteasome is constitutive in professional antigen presenting cells (pAPC). Thus, it can be helpful to include immune epitopes or epitope clusters in CTL-inducing compositions to ensure that there are CTL able to recognize the target cell regardless of the state that the target cell is in. This can be particularly true with endothelial cells, which readily assume antigen presentation functions. These concepts are more fully explained in U.S. patent application Ser. No. 09/560,465, filed on Apr., 28, 2000; Ser. No. 10/005,905, filed on Nov. 7, 2001; and a continuation thereof, U.S. application Ser. No. 11/683,397 filed on Dec. 7, 2001, each of which is entitled "EPITOPE SYNCHRONIZATION IN ANTIGEN PRESENTING CELLS," and each of which is hereby incorporated by reference in its entirety.

As discussed above, the immunogenic compositions, including in preferred embodiments, vaccines, can include TuNV antigens and epitopes, for example. The epitopes can include one or more housekeeping epitopes and/or one or more immune epitopes. Specific epitopes useful in compositions can be identified using the methods disclosed in U.S. patent application Ser. No. 09/561,074 entitled "METHOD OF EPITOPE DISCOVERY," filed on Apr. 28, 2000. For example, peptide sequences that are known or predicted to bind to some MHC restriction element can be compared to fragments produced by proteasomal digestion in order to identify those that are co-C-terminal.

Examples of useful epitopes for the embodiments of the invention, including epitopes of ED-B and PSMA, are disclosed in a U.S. Provisional Patent Application No. 60/363,210, entitled "EPITOPE SEQUENCES," filed on even date with this application, Mar. 7, 2002, and two U.S.

Provisional Patent Applications, each entitled "EPITOPE SEQUENCES;" Application Nos. 60/282,211, filed on Apr. 6, 2001 and 60/337,017, filed on Nov. 7, 2001. Each of these applications is incorporated herein by reference in its entirety.

PSMA is one example of a TuAA that can be targeted in some embodiments. PSMA is expressed in the neovasculature of most tumor types, but not by the vascular endothelium of normal tissues (Chang, S. M. et al., *Cancer Res.* 59(13):3192-8,1999; *Clin Cancer Res.* 10:2674-81, 1999). PSMA is a membrane antigen, and as such, it may be possible to attack PSMA-expressing TuNV with monoclonal antibody (mAb). However, the effectiveness of mAb in the treatment of cancer has proved to be more difficult than initially anticipated. Moreover, as other antigens are discovered to be associated with the TuNV, it is likely that many of them will prove not to be expressed at the vasculature surface, making them inaccessible to mAb attack.

T cells, particularly CTL, on the other hand, survey the expression of internal components of the cell through the process of major histocompatability complex (MHC)-restricted antigen presentation. The parameters for determining the effectiveness of T cell-activating vaccines and compositions against self-antigens are subtle. Some of the critical features and parameters relating to appropriate epitope selection are disclosed in U.S. patent application Ser. No. 09/560,465 entitled "EPITOPE SYNCHRONIZATION IN ANTIGEN PRESENTING CELLS," filed on Apr. 28, 2001; U.S. patent application Ser. No. 09/561,074 entitled "METHOD OF EPITOPE DISCOVERY," filed on Apr. 28, 2001; and U.S. patent application Ser. No. 09/561,571 entitled "EPITOPE CLUSTERS," filed on Apr. 28, 2001. Features of DNA vaccine design promoting epitope synchronization are disclosed in U.S. patent application Ser. No. 09/561,572 entitled "EXPRESSION VECTORS ENCODING EPITOPES OF TARGET-ASSOCIATED ANTIGENS," filed on Apr. 28, 2001 and U.S. Provisional Application No. 60/336,968 entitled "EXPRESSION VECTORS ENCODING EPITOPES OF TARGET-ASSOCIATED ANTIGENS AND METHODS FOR THEIR DESIGN," filed on Nov. 7, 2001. Particularly effective means of vaccine delivery are described in U.S. patent application Ser. No. 09/380,534, filed on Sep. 1, 1999, and a Continuation-in-Part thereof, U.S. patent application Ser. No. 09/776,232, filed on Feb. 2, 2001, both entitled "A METHOD OF INDUCING A CTL RESPONSE." Each of the above-mentioned references is incorporated herein by reference in its entirety.

Another example of a TuNV antigen that can be used in embodiments is fibronectin, preferably the ED-B domain. Fibronectin is subject to developmentally regulated alternative splicing, with the ED-B domain being encoded by a single exon that is used primarily in oncofetal tissues. Matsuura, H. and S. Hakomori *Proc. Natl. Acad. Sci. USA* 82:6517-6521, 1985; Carnemolla, B. et al. *J. Cell Biol.* 108:1139-1148, 1989; Loridon-Rosa, B. et al. *Cancer Res.* 50:1608-1612, 1990; Nicolo, G. et al. *Cell Differ. Dev.* 32:401-408, 1990; Borsi, L. et al. *Exp. Cell Res.* 199:98-105, 1992; Oyama, F. et al. *Cancer Res.* 53:2005-2011, 1993; Mandel, U. et al. *APMIS* 102:695-702, 1994; Farnoud, M. R. et al. *Int. J. Cancer* 61:27-34, 1995; Pujuguet, P. et al. Am. J. Pathol. 148:579-592, 1996; Gabler, U. et al. *Heart* 75:358-362, 1996; Chevalier, X. *Br. J. Rheumatol.* 35:407-415, 1996; Midulla, M. *Cancer Res.* 60:164-169, 2000.

The ED-B domain is also expressed in fibronectin of the neovasculature Kaczmarek, J. et al. *Int. J. Cancer* 59:11-16, 1994; Castellani, P. et al. *Int. J. Cancer* 59:612-618, 1994; Neri, D. et al. *Nat. Biotech.* 15:1271-1275, 1997; Karelina, T. V. and A. Z. Eisen *Cancer Detect. Prev.* 22:438-444, 1998; Tarli, L. et al. *Blood* 94:192-198, 1999; Castellani, P. et al. *Acta Neurochir.* (*Wien*) 142:277-282, 2000. As an oncofetal domain, the ED-B domain is commonly found in the fibronectin expressed by neoplastic cells, in addition to being expressed by the TuNV. Therefore, CTL-inducing compositions targeting the ED-B domain can exhibit two mechanisms of action: direct lysis of tumor cells, and disruption of tumor blood supply through destruction of the TuNV.

It should be noted that expression of the fibronectin ED-B domain has been reported in both tumor-associated and normal neovasculature (Castellani, P. et al. *Int. J. Cancer* 59:612-618, 1994). Thus, compositions based on it, or similarly expressed antigens, can be effective against other conditions associated with inappropriate angiogenesis. Further, as CTL activity can decay rapidly after withdrawal of the composition, interference with normal angiogenesis can be minimal.

Other targets for the immunogenic compositions include growth factor receptors, including those associated with vascular cells. One such example is the vascular endothelial growth factor receptor 2 (VEGFR2). U.S. Pat. No. 6,342,221 includes discussion of VEGF and VEGFR2, and is hereby incorporated by reference in its entirety. One of skill in the art will appreciate that any other antigen or protein associated with vascular cells can be a target for the immunogenic compositions, including those that are presently known and those yet to be identified.

Animal Models, Methods of Making the Models, and Composition Evaluation

Compositions designed based upon the preceding considerations are effective against the various targets. However, additional evaluation can be easily performed at any time, but preferably in a pre-clinical setting. For example, such evaluation can be used in order to further aid in composition design. Other embodiments of the invention relate to methods of evaluating the immunogenic compositions. The compositions of the present invention can be easily evaluated by one of skill in the art using animal models for composition evaluation. For example, following the routine procedures below, one of skill in the art can evaluate TuNV compositions quickly and efficiently. Thus, using the models or guidance described herein, one of skill in the art can evaluate any TuNV composition for any TuNV antigen with little or no experimentation. Further embodiments relate to methods of making the animal research models. Other embodiments relate to the research model animals. These embodiments are set forth more fully below.

Xenotransplanted Human Vasculature-Based Model

Some embodiments relate to a model system for studying the mechanisms of human microvessel formation. For example, in some embodiments, the model system can be used for preclinical evaluation of compositions. The model involves the subcutaneous implantation of telomerase-transformed human dermal microvascular endothelial cells (HDMEC) mixed with MATRIGEL (Becton Dickinson) into SCID mice. Subcutaneous implantation of telomerase-transformed HCMEC is described in Yang, J. et al. Nature Biotech 19:219-224, 2001, which is hereby incorporated by reference in its entirety. T cells activated by the compositions of this invention can be adoptively transferred, for example, into such implanted mice, and the ability of the T cells to destroy, or prevent the formation of, such human microvessels can be assessed. In other embodiments, the mouse can be directly vaccinated and evaluated. Also, in still further embodiments, the model system can be further adapted for testing compositions effective in non-human species by substituting DMEC from other species and species-matched telomerase, and by using analogous reagents to those described below for the human system.

The MHC-restriction elements presenting the epitopes of the composition being tested, preferably, are shared by the HDMEC line implanted into the mice. The T cells can be derived from in vitro immunization of human T cells, or by immunization of HLA-transgenic mice (procedures for which are well known in the art and examples of which are provided in the above incorporated patent applications). Use of T cells generated in HLA-transgeneic mice allows matching of genetic backgrounds between the adoptively transferred T cells and the host, thereby reducing the possibility of allogeneic or xenogeneic reactions that might complicate interpretation of the results. However, depending on the mouse strains available, this might require cross-breeding to get the HLA-transgene and SCID phenotype on the same genetic background. In the alternative, the donor T cells (human or murine) can be subjected to one or more rounds of in vitro stimulation to enrich for the desired population or establish a clone, and thereby similarly avoid undesired reactivities.

Techniques for in vitro immunization are know in the art, for example, Stauss et al., *Proc. Natl. Acad. Sci. USA* 89:7871-7875, 1992; Salgaller et al. *Cancer Res.* 55:4972-4979, 1995; Tsai et al., *J. Immunol.* 158:1796-1802, 1997; and Chung et al., *J. Immunother.* 22:279-287, 1999. Once generated, whether in vivo or in vitro, sufficient numbers of such T cells can be obtained by expansion in vitro through stimulation with the compositions of this invention and/or cytokines (see for example Kurokawa, T. et al., *Int. J. Cancer* 91:749-746, 2001) or other mitogens. These T cells can constitute a clone or a polyclonal population recognizing one or more epitopes. In preferred embodiments, on the order of $10^5$ to $10^8$ cells are transferred for adoptive transfer experiments in mice. (See for example Drobyski, W. R. et al. *Blood* 97:2506-2513, 2001; Seeley B. M. et al. *Otolaryngol. Head Neck Surg.* 124:436-441, 2001; Kanwar, J. R. et al. *Cancer Res.* 61:1948-1956, 2001). Clones and otherwise more enriched populations generally require the transfer of fewer cells.

Transfer of the T cells can take place shortly before, concurrent with, or subsequent to implantation or establishment of the HDMEC. Parameters that can be assessed to evaluate effectiveness of the compositions include vessel formation, changes in vessel density, and ability to carry mouse blood (as described in Yang et al.), and the like. Assessment can be carried out as early as one week, and at least as long as 6 weeks, after implantation of telomerase-transformed HDMEC, preferably after 2 weeks; and from a day to more than 6 weeks after T cell transfer, preferably after 1 to 3 weeks. Generally, assessment can include comparison of mice receiving T cells reactive with the target antigen with mice receiving naïve (including sham-immunized), or irrelevant epitope-reactive T cells.

Relevant antigens can be expressed generally in neovasculature or preferentially by TuNV. Expression can be confirmed by a variety of techniques known in the art, including immunohistochemistry and RT-PCR. For example, tumor cells can be implanted along with the HDMEC. This can result in inducing expression of antigens preferentially expressed by TuNV. In one example, this can be accomplished by implanting a block of tumor tissue adjacent to the HDMEC-containing MATRIGEL implant, injecting tumor cells at the site of the implant, implanting tumor cell-containing MATRIGEL adjacent to the HDMEC-containing MATRIGEL implant, incorporating both tumor cells and HDMEC into the same MATRIGEL implant or by any other suitable method. As discussed above, in some embodiments, tumor cells can be implanted along with vascular cells. The animals so made, can be used as research models. Additional variations will be apparent to one of skill in the art.

HLA-Transgenic Animal Model

For antigens that are conserved, in sequence and/or expression profile, between human and the model species, HLA-transgenic strains allow another approach, namely vaccination of the model animal to combat a syngeneic tumor. The ED-B domain of fibronectin provides such an opportunity, as it is a marker of angiogenesis and has identical amino acid sequence in both humans and mice (Nilsson, F. et al. *Cancer Res.* 61:711-716, 2001). Moreover, spontaneous tumor tissue from a strain of HLA-A2 transgenic mice has been isolated and propagated. Epitope discovery and selection, and composition design and delivery for CTL inducing compositions are discussed above.

The tumor cell line, M1, is derived from a spontaneous salivary glandular cystadenocarcinoma. The M1 tumor cell line and methods of using the same is disclosed in U.S. Provisional Application No. 60/363,131, filed on even date with this application, Mar. 7, 2001, entitled "AN HLA-TRANSGENIC MURINE TUMOR CELL LINE," which is hereby incorporated by reference in its entirety. The tumor cell line, can arise in individuals of the HHD-A2 transgenic mouse strain of S. Pascolo et al. (J. Exp. Med. 185:2043-2051, 1997). These mice express a single monochain class I molecule comprising human β (beta)2-microglobulin, and α1 (alpha-1), and α2 (alpha-2) domains of HLA-A2.1 with the balance of the molecule derived from the murine class I molecule $H2D^b$. Blocks of tumor can be transplanted into new individuals where the tumor will re-grow, commonly within 1-3 weeks, with 3 mm blocks growing to 3 cm. Alternatively, tumor tissue can be disaggregated and the tumor cells grown in vitro. Upon harvest, the tumor cells can be injected subcutaneously into the neck or abdomen (2.5× $10^6$ cells for 1-3 successive days), to result in a visible tumor in approximately 5-12 weeks for early passage cells. After the cells have become better adapted to growth in vitro, single injections of $1\times10^6$ to $1\times10^7$ cells lead to visible tumor in ten days. Generally, the initial tumor consistently occurs in the vicinity of the salivary glands, but secondary tumors can also occur in a variety of locations, including kidney, lung, liver, and abdominal muscle.

To evaluate the efficacy of a composition, it can be administered before, concurrent with, or subsequent to establishment of the tumor, depending on the expected mechanism of the composition. For therapeutic compositions intended to be used with some sort of debulking technique (e.g. surgery), concurrent administration can be appropriate. The better established the tumor is before treatment begins, the more stringent the test.

Both animal evaluation models have been described for the testing of human compositions. However, application to veterinary compositions is analogous, requiring only the substitution of species-matched endothelial cells, MHC, TuAA, etc.

All patents, patent applications, and publications referred to herein are hereby incorporated by reference in their entirety.

The following examples are intended for illustration purposes only, and should not be construed as limiting the scope of the invention in any way.

EXAMPLES

Example 1

A preclinical study was carried out using the already identified antigens PSMA and ED-B disclosed herein. The results of the study revealed excellent candidate epitopes. See table 9 below.

Example 1.1

Cluster Analysis (PSMA$_{163-192}$)

A peptide, AFSPQGMPEGDLVYVNYARTED-FFKLERDM, PSMA$_{163-192}$, (SEQ ID NO. 3), containing an A1 epitope cluster from prostate specific membrane antigen, PSMA$_{168-190}$ (SEQ ID NO. 4) was synthesized using standard solid-phase F-moc chemistry on a 433A ABI Peptide synthesizer. After side chain deprotection and cleavage from the resin, peptide first dissolved in formic acid and then diluted into 30% Acetic acid, was run on a reverse-phase preparative HPLC C4 column at following conditions: linear AB gradient (5% B/min) at a flow rate of 4 ml/min, where eluent A is 0.1% aqueous TFA and eluent B is 0.1% TFA in acetonitrile. A fraction at time 16.642 min containing the expected peptide, as judged by mass spectrometry, was pooled and lyophilized. The peptide was then subjected to proteasome digestion and mass spectrum analysis essentially as described above. Prominent peaks from the mass spectra are summarized in Table 1.

N-terminal Pool Sequence Analysis

One aliquot at one hour of the proteasomal digestion was subjected to N-terminal amino acid sequence analysis by an ABI 473A Protein Sequencer (Applied Biosystems, Foster City, Calif.). Determination of the sites and efficiencies of cleavage was based on consideration of the sequence cycle, the repetitive yield of the protein sequencer, and the relative yields of amino acids unique in the analyzed sequence. That is if the unique (in the analyzed sequence) residue X appears only in the nth cycle a cleavage site exists n-1 residues before it in the N-terminal direction. In addition to helping resolve any ambiguity in the assignment of mass to sequences, these data also provide a more reliable indication of the relative yield of the various fragments than does mass spectrometry.

Figure 1C:
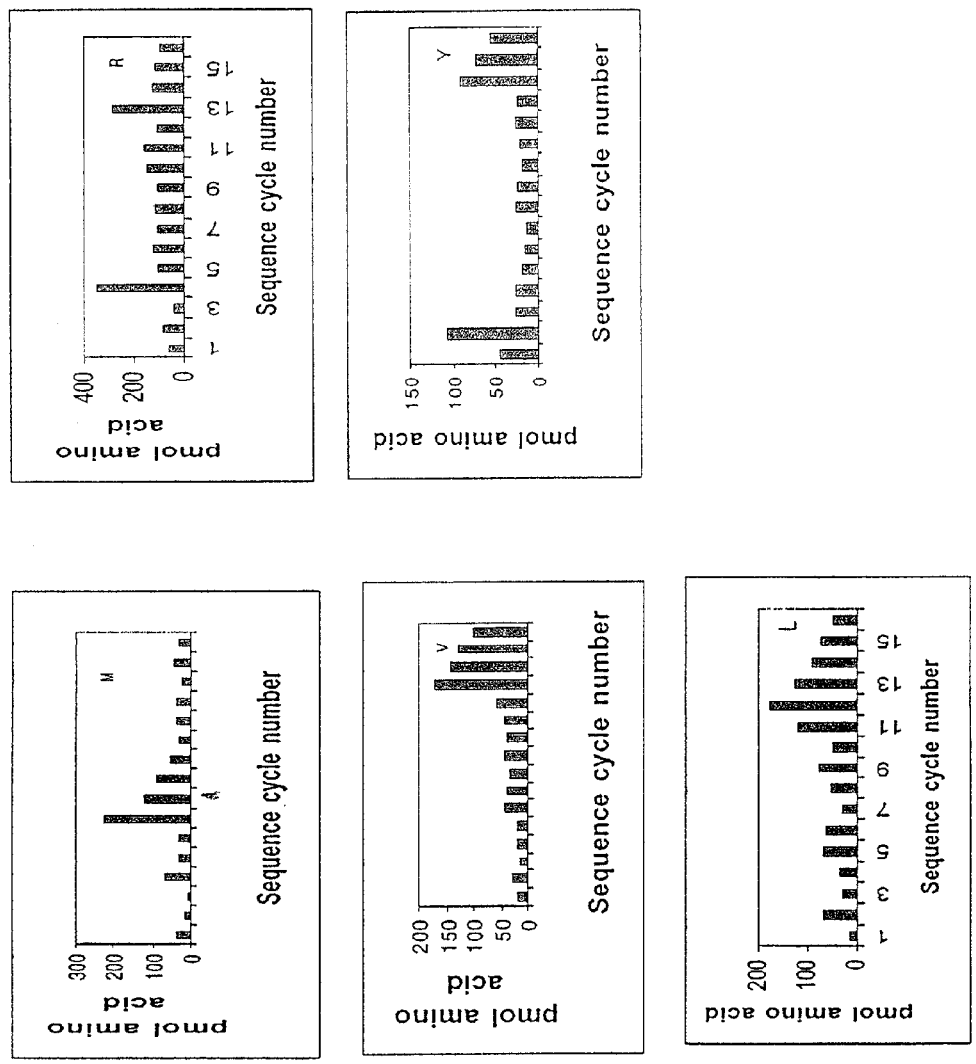

For PSMA$_{163-192}$ (SEQ ID NO. 3) this pool sequencing supports a single major cleavage site after V$_{177}$ and several minor cleavage sites, particularly one after Y$_{179}$. Reviewing the results presented in FIGS. 1A-C reveals the following:

S at the 3$^{rd}$ cycle indicating presence of the N-terminus of the substrate.

Q at the 6$^{th}$ cycle indicating presence of the N-terminus of the substrate.

N at the 1$^{st}$ cycle indicating cleavage after V$_{177}$.

N at the 3$^{rd}$ cycle indicating cleavage after V$_{175}$. Note the fragment 176-192 in Table 1.

T at the 5$^{th}$ cycle indicating cleavage after V$_{177}$.

T at the 1$^{st}$-3$^{rd}$ cycles, indicating increasingly common cleavages after R$_{181}$, A$_{180}$ and Y$_{179}$. Only the last of these correspond to peaks detected by mass spectrometry; 163-179 and 180-192, see Table 1. The absence of

TABLE 1

PSMA$_{163-192}$ Mass Peak Identification.

| SEQ ID NO. | PEPTIDE | SEQUENCE | CALCULATED MASS (MH$^+$) |
|---|---|---|---|
| 110 | 163-177 | AFSPQGMPEGDLVYV | 1610.0 |
| 111 | 178-189 | NYARTEDFFKLE | 1533.68 |
| 112 | 170-189 | PEGDLVYVNYARTEDFPKLE | 2406.66 |
| 113 | 178-191 | NYARTEDFFKLERD | 1804.95 |
| 114 | 170-191 | PEGDLVYVNYARTEDFFKLERD | 2677.93 |
| 115 | 178-192 | NYARTEDFFKLERDM | 1936.17 |
| 116 | 163-176 | AFSPQGMPEGDLVY | 1511.70 |
| 117 | 177-192 | VNYARTEDFFKLERDM | 2035.30 |
| 118 | 163-179 | AFSPQGMPEGDLVYVNY | 1888.12 |
| 119 | 180-192 | ARTEDFFKLERDM | 1658.89 |
| 120 | 163-183 | AFSPQGMPEGDLVYVNYARTE | 2345.61 |
| 121 | 184-192 | DFFKLERDM | 1201.40 |
| 122 | 176-192 | YVNYARTEDFFKLERDM | 2198.48 |
| 123 | 167-185 | QGMPEGDLVYVNYARTEDF | 2205.41 |
| 124 | 178-186 | NYARTEDFF | 1163.22 |

Boldface sequences correspond to peptides predicted to bind to MHC, see Table 2.

the others can indicate that they are on fragments smaller than were examined in the mass spectrum.

K at the $4^{th}$, $8^{th}$, and $10^{th}$ cycles indicating cleavages after $E_{183}$, $Y_{179}$, and $V_{177}$, respectively, all of which correspond to fragments observed by mass spectroscopy. See Table 1.

A at the $1^{st}$ and $3^{rd}$ cycles indicating presence of the N-terminus of the substrate and cleavage after $V_{177}$, respectively.

P at the $4^{th}$ and $8^{th}$ cycles indicating presence of the N-terminus of the substrate.

G at the $6^{th}$ and $10^{th}$ cycles indicating presence of the N-terminus of the substrate.

M at the $7^{th}$ cycle indicating presence of the N-terminus of the substrate and/or cleavage after $F_{185}$.

M at the $15^{th}$ cycle indicating cleavage after $V_{177}$.

The $1^{st}$ cycle can indicate cleavage after $D_{191}$, see Table 1.

R at the $4^{th}$ and $13^{th}$ cycle indicating cleavage after $V_{177}$.

R at the $2^{nd}$ and $11^{th}$ cycle indicating cleavage after $Y_{179}$.

V at the $2^{nd}$, $6^{th}$, and $13^{th}$ cycle indicating cleavage after $V_{175}$, $M_{169}$ and presence of the N-terminus of the substrate, respectively. Note fragments beginning at 176 and 170 in Table 1.

Y at the $1^{st}$, $2^{nd}$, and $14^{th}$ cycles indicating cleavage after $V_{175}$, $V_{177}$, and presence of the N-terminus of the substrate, respectively.

L at the $11^{th}$ and $12^{th}$ cycles indicating cleavage after $V_{177}$, and presence of the N-terminus of the substrate, respectively, is the interpretation most consistent with the other data. Comparing to the mass spectrometry results we see that L at the $2^{nd}$, $5^{th}$, and $9^{th}$ cycles is consistent with cleavage after $F_{186}$, $E_{183}$ or $M_{169}$, and $Y_{179}$, respectively. See Table 1.

Epitope Identification

Fragments co-C-terminal with 8-10 amino acid long sequences predicted to bind HLA by the SYFPEITHI or NIH algorithms were chosen for further analysis. The digestion and prediction steps of the procedure can be usefully practiced in any order. Although the substrate peptide used in proteasomal digest described here was specifically designed to include a predicted HLA-A1 binding sequence, the actual products of digestion can be checked after the fact for actual or predicted binding to other MHC molecules. Selected results are shown in Table 2.

TABLE 2

Predicted HLA binding by proteasomally generated fragments

| I. SEQ ID NO | II. PEPTIDE | HLA | SYFPEITHI | NIH |
|---|---|---|---|---|
| 5 & (6) | (G)MPEGDLVYVA | A*0201 | 17 (27) | (2605) |
| | | B*0702 | 20 | <5 |
| | | B*5101 | 22 | 314 |
| 7 & (8) | (Q)GMPEGDLVY | A1 | 24(26) | <5 |
| | | A3 | 16(18) | 36 |
| | | B*2705 | 17 | 25 |
| 9 | MPEGDLVY | B*5101 | 15 | NP† |
| 10 & (11) | (P)EGDLVYVNY | A1 | 27(15) | 12 |
| | | A26 | 23(17) | NP |
| 12 | LVYVNYARTE | A3 | 21 | <5 |
| 13 & (14) | (Y)VNYARTEDF | A26 | (20) | NP |
| | | B*08 | 15 | <5 |
| | | B*2705 | 12 | 50 |

TABLE 2-continued

Predicted HLA binding by proteasomally generated fragments

| I. SEQ ID NO | II. PEPTIDE | HLA | SYFPEITHI | NIH |
|---|---|---|---|---|
| 15 | NYARTEDFF | A24 | NP\ | 100 |
| | | Cw*0401 | NP | 120 |
| 16 | YARTEDFF | B*08 | 16 | <5 |
| 17 | RTEDFFKLE | A1 | 21 | <5 |
| | | A26 | 15 | NP |

†No prediction

HLA-A*0201 Binding assay:

Binding of the candidate epitope $PSMA_{168-177}$, GMPEGDLVYV, (SEQ ID NO. 6) to HLA-A2.1 was assayed using a modification of the method of Stauss et al., (Proc Natl Acad Sci USA 89(17):7871-5 (1992)). Specifically, T2 cells, which express empty or unstable MHC molecules on their surface, were washed twice with Iscove's modified Dulbecco's medium (IMDM) and cultured overnight in serum-free AIM-V medium (Life Technologies, Inc., Rockville, Md.) supplemented with human β2-microglobulin at 3 μg/ml (Sigma, St. Louis, Mo.) and added peptide, at 800, 400, 200, 100, 50, 25, 12.5, and 6.25 μg/ml. in a 96-well flat-bottom plate at 3×10⁵ cells/200 μl/well. Peptide was mixed with the cells by repipeting before distributing to the plate (alternatively peptide can be added to individual wells), and the plate was rocked gently for 2 minutes. Incubation was in a 5% $CO_2$ incubator at 37° C. The next day the unbound peptide was removed by washing twice with serum free RPMI medium and a saturating amount of anti-class I HLA monoclonal antibody, fluorescein isothiocyanate (FITC)-conjugated anti-HLA A2, A28 (One Lambda, Canoga Park, Calif.) was added. After incubation for 30 minutes at 4° C., cells were washed 3 times with PBS supplemented with 0.5% BSA, 0.05% (w/v) sodium azide, pH 7.4-7.6 (staining buffer). (Alternatively W6/32 (Sigma) can be used as the anti-class I HLA monoclonal antibody the cells washed with staining buffer and then incubated with fluorescein isothiocyanate (FITC)-conjugated goat F(ab') antimouse-IgG (Sigma) for 30 min at 4° C. and washed 3 times as before.) The cells were resuspended in 0.5 ml staining buffer. The analysis of surface HLA-A2.1 molecules stabilized by peptide binding was performed by flow cytometry using a FACScan (Becton Dickinson, San Jose, Calif.). If flow cytometry is not to be performed immediately the cells can be fixed by adding a quarter volume of 2% paraformaldehyde and storing in the dark at 4 C.

Figure 2:
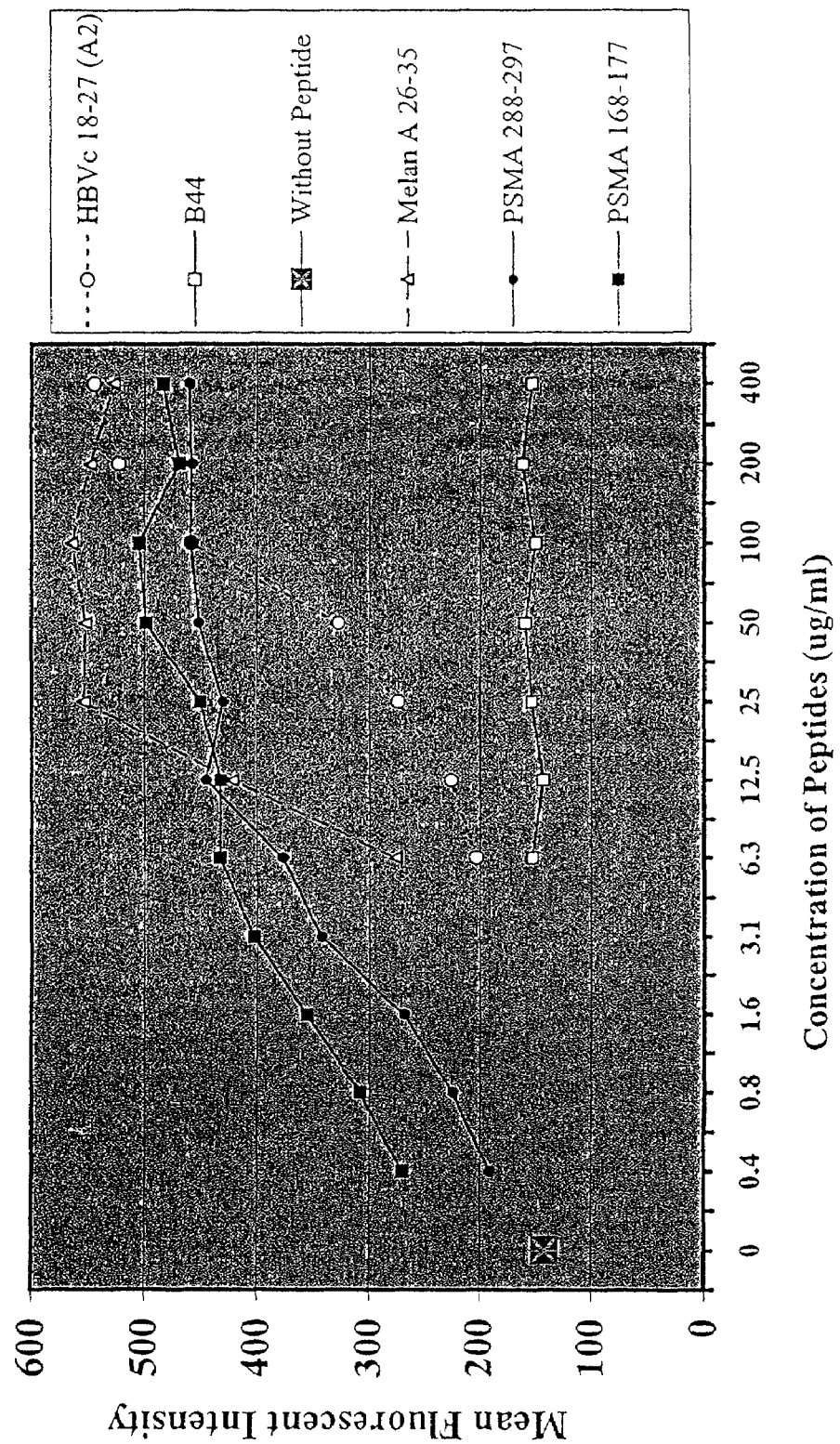
FIG. 2 shows binding curves for HLA-A2:$PSMA_{168-177}$ and HLA-A2:$PSMA_{288-297}$ with controls.

As seen in FIG. 2, this epitope exhibits significant binding at even lower concentrations than the positive control peptides. The Melan-A peptide used as a control in this assay (and throughout this disclosure), ELAGIGILTV (SEQ ID NO: 106), is actually a variant of the natural sequence (EAAGIGILTV; SEQ ID NO: 107)) and exhibits a high affinity in this assay. The known A2.1 binder FLPSDYFPSV ($HBV_{18-27}$; SEQ ID NO: 107) was also used as a positive control. An HLA-B44 binding peptide, AEMGKYSFY (SEQ ID NO: 109), was used as a negative control. The fluorescence obtained from the negative control was similar to the signal obtained when no peptide was used in the assay. Positive and negative control peptides were chosen from Table 18.3.1 in *Current Protocols in Immunology* p. 18.3.2, John Wiley and Sons, New York, 1998.

Example 1.2

Cluster Analysis ($PSMA_{281-310}$).

Another peptide, RGIAEAVGLPSIPVHPIGYY-DAQKLLEKMG, $PSMA_{281-310}$, (SEQ ID NO. 18), containing an A1 epitope cluster from prostate specific membrane antigen, $PSMA_{283-307}$ (SEQ ID NO. 19), was synthesized using standard solid-phase F-moc chemistry on a 433A ABI Peptide synthesizer. After side chain deprotection and cleavage from the resin, peptide in ddH2O was run on a reverse-phase preparative HPLC C18 column at following conditions: linear AB gradient (5% B/min) at a flow rate of 4 ml/min, where eluent A is 0.1% aqueous TFA and eluent B is 0.1% TFA in acetonitrile. A fraction at time 17.061 min containing the expected peptide as judged by mass spectrometry, was pooled and lyophilized. The peptide was then subjected to proteasome digestion and mass spectrum analysis essentially as described above. Prominent peaks from the mass spectra are summarized in Table 3.

N-terminal Pool Sequence Analysis

One aliquot at one hour of the proteasomal digestion (see Example 3 part 3 above) was subjected to N-terminal amino acid sequence analysis by an ABI 473A Protein Sequencer (Applied Biosystems, Foster City, Calif.). Determination of the sites and efficiencies of cleavage was based on consideration of the sequence cycle, the repetitive yield of the protein sequencer, and the relative yields of amino acids unique in the analyzed sequence. That is if the unique (in the analyzed sequence) residue X appears only in the nth cycle a cleavage site exists n-1 residues before it in the N-terminal direction. In addition to helping resolve any ambiguity in the assignment of mass to sequences, these data also provide a more reliable indication of the relative yield of the various fragments than does mass spectrometry.

Figure 3:
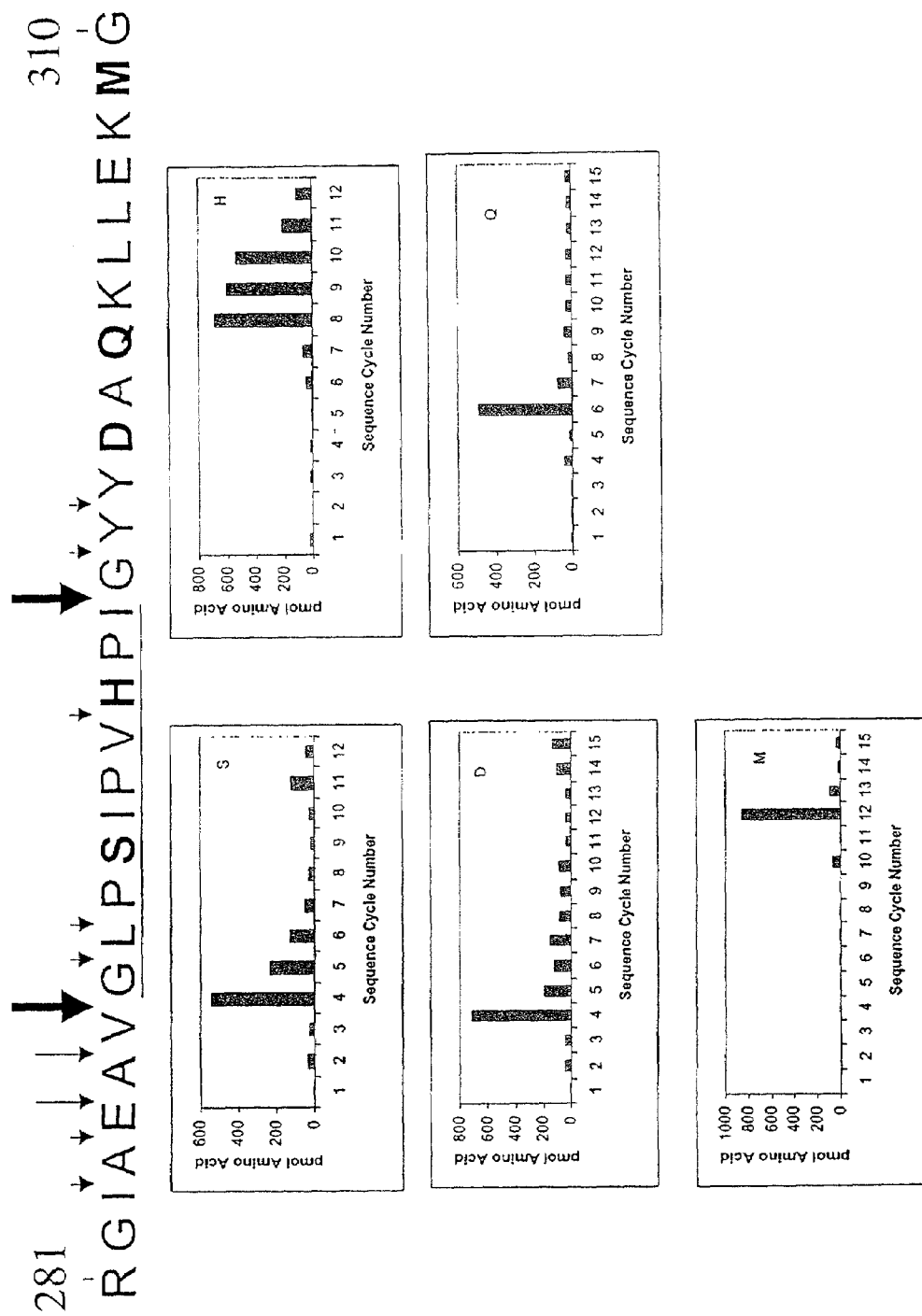
FIG. 3 shows results of N-terminal pool sequencing of a T=60 min. time point aliquot of the $PSMA_{281-310}$ proteasomal digest.

For $PSMA_{281-310}$ (SEQ ID NO. 18) this pool sequencing supports two major cleavage sites after $V_{287}$ and $I_{297}$ among other minor cleavage sites. Reviewing the results presented in FIG. 3 reveals the following:

TABLE 3

$PSMA_{281-310}$ Mass Peak Identification.

| SEQ ID NO. | PEPTIDE SEQUENCE | | CALCULATED MASS ($MH^+$) |
|---|---|---|---|
| 125 | 281-297 | RGIAEAVGLPSIPVHPI\* | 1727.07 |
| 126 | 286-297 | AVGLPSIPVHPI\*\* | 1200.46 |
| 127 | 287-297 | VGLPSIPVHPI | 1129.38 |
| 128 | 288-297 | GLPSIPVHPI† | 1030.25 |
| 129 | 298-310 | GYYDAQKLLEKMG‡ | 1516.5 |
| 130 | 298-305 | GYYDAQKL§ | 958.05 |
| 131 | 281-305 | RGIAEAVGLPSIPVHPIGYYDAQKL | 2666.12 |
| 132 | 281-307 | RGIAEAVGLPSIPVHPIGYYDAQKLLE | 2908.39 |
| 133 | 286-307 | AVGLPSIPVHPIGYYDAQKLLE¶ | 2381.78 |
| 134 | 287-307 | VGLPSIPVHPIGYYDAQKLLE | 2310.70 |
| 135 | 288-307 | GLPSIPVHPIGYYDAQKLLE# | 2211.57 |
| 136 | 281-299 | RGIAEAVGLPSIPVHPIGY | 1947 |
| 137 | 286-299 | AVGLPSIPVHPIGY | 1420.69 |
| 138 | 287-299 | VGLPSIPVHPIGY | 1349.61 |
| 139 | 288-299 | GLPSIPVHPIGY | 1250.48 |
| 140 | 287-310 | VGLPSIPVHPIGYYDAQKLLEKMG | 2627.14 |
| 141 | 288-310 | GLPSIPVHPIGYYDAQKLLEKMG | 2528.01 |

Boldface sequences correspond to peptides to bind to MHC, see Table 4.
\*By mass alone this peak could also have been 296-310 or 288-303.
\*\*By mass alone this peak could also have been 298-307. Combination of HPLC and mass spectrometry show that at some later time points this peak is a mixture of both species.
†By mass alone this peak could also have been 289-298.
‡By mass alone this peak could also have been 281-295 or 294-306.
§By mass alone this peak could also have been 297-303.
¶By mass alone this peak could also have been 285-306.
By mass alone this peak could also have been 288-303.
None of these alternate assignments are supported N-terminal pool sequence analysis.

S at the 4$^{th}$ and 11$^{th}$ cycles indicating cleavage after V$_{287}$ and presence of the N-terminus of the substrate, respectively.

H at the 8$^{th}$ cycle indicating cleavage after V$_{287}$. The lack of decay in peak height at positions 9 and 10 versus the drop in height present going from 10 to 11 can suggest cleavage after A$_{286}$ and E$_{285}$ as well, rather than the peaks representing latency in the sequencing reaction.

D at the 2$^{nd}$, 4$^{th}$, and 7$^{th}$ cycles indicating cleavages after Y$_{299}$, I$_{297}$, and V$_{294}$, respectively. This last cleavage is not observed in any of the fragments in Table 4 or in the alternate assignments in the notes below.

Q at the 6$^{th}$ cycle indicating cleavage after I$_{297}$.

M at the 10$^{th}$ and 12$^{th}$ cycle indicating cleavages after Y$_{299}$ and I$_{297}$, respectively.

Epitope Identification

Fragments co-C-terminal with 8-10 amino acid long sequences predicted to bind HLA by the SYFPEITHI or NIH algorithms were chosen for further study. The digestion and prediction steps of the procedure can be usefully practiced in any order. Although the substrate peptide used in proteasomal digest described here was specifically designed to include a predicted HLA-A1 binding sequence, the actual products of digestion can be checked after the fact for actual or predicted binding to other MHC molecules. Selected results are shown in Table 4.

TABLE 4

Predicted HLA binding by proteasomally generated fragments: PSMA$_{281-310}$

| III. SEQ ID NO. | IV. PEPTIDE | HLA | SYFPEITHI | NIH |
|---|---|---|---|---|
| 20 & (21) | (G)LPSIPVHPI | A*0201 | 16(24) | (24) |
| | | B*0702/B7 | 23 | 12 |
| | | B*5101 | 24 | 572 |
| | | Cw*0401 | NP† | 20 |
| 22 & (23) | (P)IGYYDAQKL | A*0201 | (16) | <5 |
| | | A26 | (20) | NP |
| | | B*2705 | 16 | 25 |
| | | B*2709 | 15 | NP |
| | | B*5101 | 21 | 57 |
| | | Cw*0301 | NP | 24 |

TABLE 4-continued

Predicted HLA binding by proteasomally generated fragments: PSMA$_{281-310}$

| III. SEQ ID NO. | IV. PEPTIDE | HLA | SYFPEITHI | NIH |
|---|---|---|---|---|
| 24 & (25) | (P)SIPVHPIGY | A1 | 21(27) | <5 |
| | | A26 | 22 | NP |
| | | A3 | 16 | <5 |
| 26 | IPVHPIGY | B*5101 | 16 | NP |
| 27 | YYDAQKLLE | A1 | 22 | <5 |

†No prediction

As seen in Table 4, N-terminal addition of authentic sequence to epitopes can often generate still useful, even better epitopes, for the same or different MHC restriction elements. Note for example the pairing of (G)LPSIPVHPI with HLA-A*0201, where the 10-mer can be used as a vaccine useful with several MHC types by relying on N-terminal trimming to create the epitopes for HLA-B7, -B*5101, and Cw*0401.

HLA-A*0201 Binding Assay:

HLA-A*0201 binding studies were preformed with PSMA$_{288-297}$, GLPSIPVHPI, (SEQ ID NO. 21) essentially as described in Example 1.1 above. As seen in FIG. 2, this epitope exhibits significant binding at even lower concentrations than the positive control peptides.

Example 1.3

Cluster Analysis (PSMA$_{454-481}$).

Another peptide, SSIEGNYTLRVDCTPLMYSLVHLTKEL, PSMA$_{454-481}$, (SEQ ID NO. 28) containing an epitope cluster from prostate specific membrane antigen, was synthesized by MPS (purity>95%) and subjected to proteasome digestion and mass spectrum analysis as described above. Prominent peaks from the mass spectra are summarized in Table 5.

TABLE 5

PSMA$_{454-481}$ Mass Peak Identification.

| SEQ ID NO. | MS PEAK (measured) | PEPTIDE | SEQUENCE | CALCULATED MASS (MH$^+$) |
|---|---|---|---|---|
| 142 | 1238.5 | 454-464 | SSIEGNYTLRV | 1239.78 |
| 143 | 1768.38 ± 0.60 | 454-469 | SSIEGNYTLRVDCTPL | 1768.99 |
| 144 | 1899.8 | 454-470 | SSIEGNYTLRVDCTPLM | 1900.19 |
| 145 | 1097.63 ± 0.91 | 463-471 | RVDCTPLMY | 1098.32 |
| 146 | 2062.87 ± 0.68 | 454-471* | SSIEGNYTRVDCTPLMY | 2063.36 |

TABLE 5-continued

PSMA$_{454-481}$ Mass Peak Identification.

| SEQ ID NO. | MS PEAK (measured) | PEPTIDE | SEQUENCE | CALCULATED MASS (MH$^+$) |
|---|---|---|---|---|
| 147 | 1153 | 472-481** | SLVHNLTKEL | 1154.36 |
| 148 | 1449.93 ± 1.79 | 470-481 | MYSLVHNLTKEL | 1448.73 |

Boldface sequence correspond to peptides predicted to bind to MHC, see Table 6.
*On the basis of mass alone this peak could equally well be assigned to the peptide 455-472 however proteasomal removal of just the N-terminal amino acid is considered unlikely. If the issue were important it could be resolved by N-terminal sequencing.
**On the basis of mass this fragment might also represent 455-464.

Epitope Identification

Fragments co-C-terminal with 8-10 amino acid long sequences predicted to bind HLA by the SYFPEITHI or NIH algorithms were chosen for further study. The digestion and prediction steps of the procedure can be usefully practiced in any order. Although the substrate peptide used in proteasomal digest described here was specifically designed to include predicted HLA-A2.1 binding sequences, the actual products of digestion can be checked after the fact for actual or predicted binding to other MHC molecules. Selected results are shown in Table 6.

B*5101 by relying on N-terminal trimming to create the epitope.

HLA-A*0201 Binding Assay

Figure 4:
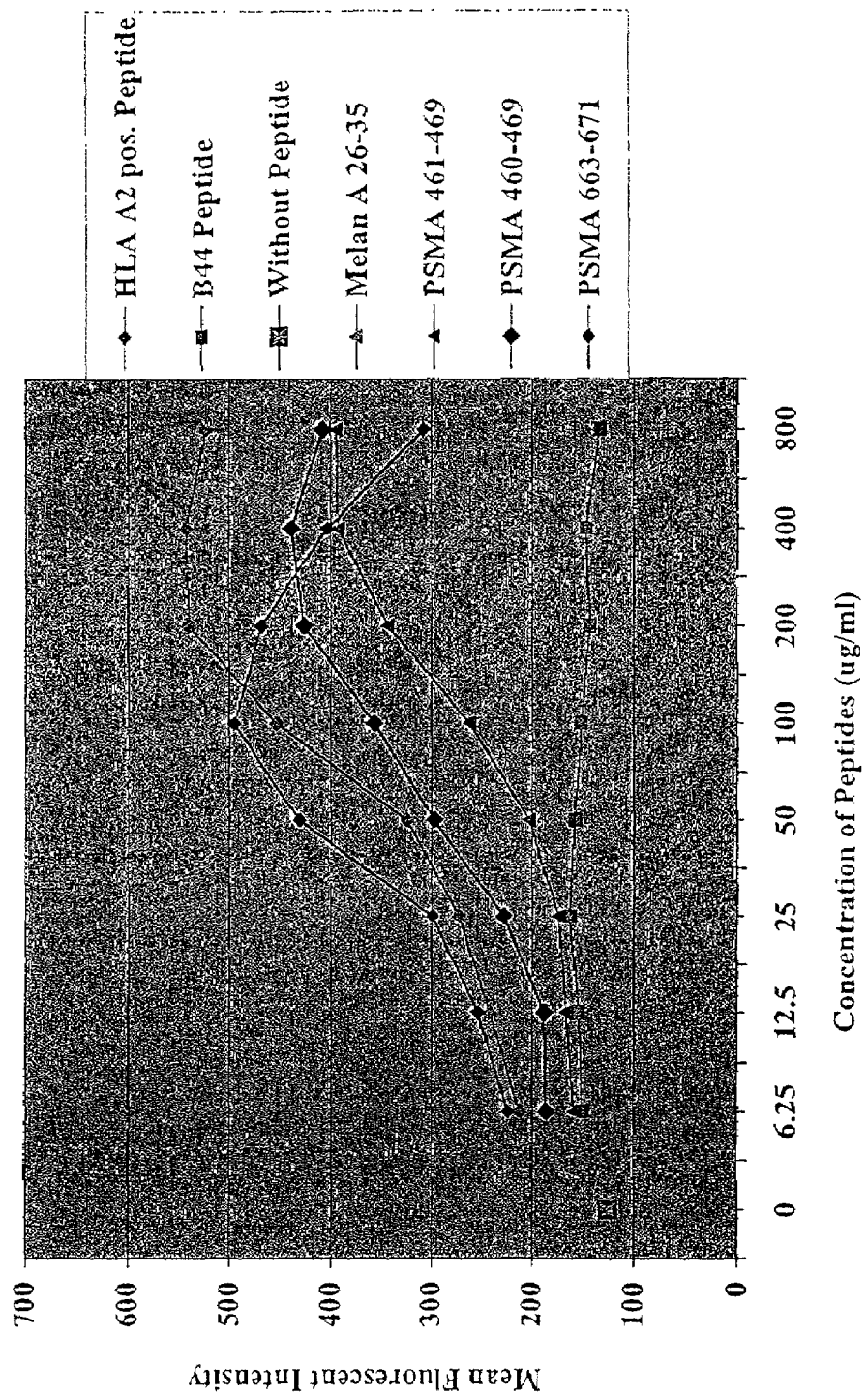
FIG. 4 shows binding curves for HLA-A2:$PSMA_{461-469}$, HLA-A2:$PSMA_{460-469}$, and HLA-A2:$PSMA_{663-671}$, with controls.

HLA-A*0201 binding studies were preformed, essentially as described in Example 1.1 above, with PSMA$_{460-469}$, YTLRVDCTPL, (SEQ ID NO.33). As seen in FIG. 4, this epitope was found to bind HLA-A2.1 to a similar extent as the known A2.1 binder FLPSDYFPSV (HBV$_{18-27}$; SEQ ID NO: 108) used as a positive control. Additionally, PSMA$_{461-469}$, (SEQ ID NO. 32) binds nearly as well.

TABLE 6

Predicted HLA binding by proteasomally generated fragments

| V. SEQ ID NO | VI. PEPTIDE | HLA | SYFPEITHI | NIH |
|---|---|---|---|---|
| 29 & (30) | (S)IEGNYTLRV | A1 | (19) | <5 |
|  |  | A*0201 | 16(22) | <5 |
| 31 | EGNYTLRV | B*5101 | 15 | NP† |
| 32 & (33) | (Y)TLRVDCTPL | A*0201 | 20(18) | (5) |
|  |  | A26 | 16(18) | NP |
|  |  | B7 | 14 | 40 |
|  |  | B8 | 23 | <5 |
|  |  | B*2705 | 12 | 30 |
|  |  | Cw*0301 | NP | (30) |
| 34 | LRVDCTPLM | B*2705 | 20 | 600 |
|  |  | B*2709 | 20 | NP |
| 35 & (36) | (L)RVDCTPLMY | A1 | 32(22) | 125(13.5) |
|  |  | A3 | 25 | <5 |
|  |  | A26 | 22 | NP |
|  |  | B*2702 | NP | (200) |
|  |  | B*2705 | 13(NP) | (1000) |

†No prediction

As seen in Table 6, N-terminal addition of authentic sequence to epitopes can often generate still useful, even better epitopes, for the same or different MHC restriction elements. Note for example the pairing of (L)RVDCTPLMY (SEQ ID NOS 35 and (36)) with HLA-B*2702/5, where the 10-mer has substantial predicted halftimes of dissociation and the co-C-terminal 9-mer does not. Also note the case of SIEGNYTLRV (SEQ ID NO 30) a predicted HLA-A*0201 epitope which can be used as a vaccine useful with HLA- ELISPOT Analysis: PSMA$_{463-471}$ (SEQ ID NO. 35)

The wells of a nitrocellulose-backed microtiter plate were coated with capture antibody by incubating overnight at 4° C. using 50 µl/well of 4 µg/ml murine anti-human –IFN monoclonal antibody in coating buffer (35 mM sodium bicarbonate, 15 mM sodium carbonate, pH 9.5). Unbound antibody was removed by washing 4 times 5 min. with PBS. Unbound sites on the membrane then were blocked by adding 200 µl/well of RPMI medium with 10% serum and incubating 1 hr. at room temperature. Antigen stimulated CD8$^+$ T cells, in 1:3 serial dilutions, were seeded into the wells of the microtiter plate using 100 µl/well, starting at $2 \times 10^5$ cells/well. (Prior antigen stimulation was essentially as described in Scheibenbogen, C. et al. *Int. J. Cancer* 71:932-936, 1997; which is incorporated herein by reference in its entirety.) $PSMA_{462-471}$ (SEQ ID NO. 36) was added to a final concentration of 10 µg/ml and IL-2 to 100 U/ml and the cells cultured at 37° C. in a 5% $CO_2$, water-saturated atmosphere for 40 hrs. Following this incubation the plates were washed with 6 times 200 µl/well of PBS containing 0.05% Tween-20 (PBS-Tween). Detection antibody, 50 µl/well of 2 µg/ml biotinylated murine anti-human –IFN monoclonal antibody in PBS+10% fetal calf serum, was added and the plate incubated at room temperature for 2 hrs. Unbound detection antibody was removed by washing with 4 times 200 µl of PBS-Tween. 100 µl of avidin-conjugated horseradish peroxidase (Pharmingen, San Diego, Calif.) was added to each well and incubated at room temperature for 1 hr. Unbound enzyme was removed by washing with 6 times 200 µl of PBS-Tween. Substrate was prepared by dissolving a 20 mg tablet of 3-amino 9-ethylcoarbasole in 2.5 ml of N,N-dimethylformamide and adding that solution to 47,5 ml of 0.05 M phosphate-citrate buffer (pH 5.0). 25 µl of 30% $H_2O_2$ was added to the substrate solution immediately before distributing substrate at 100 µl/well and incubating the plate at room temperature. After color development (generally 15-30 min.), the reaction was stopped by washing the plate with water. The plate was air dried and the spots counted using a stereomicroscope.

Figure 5:
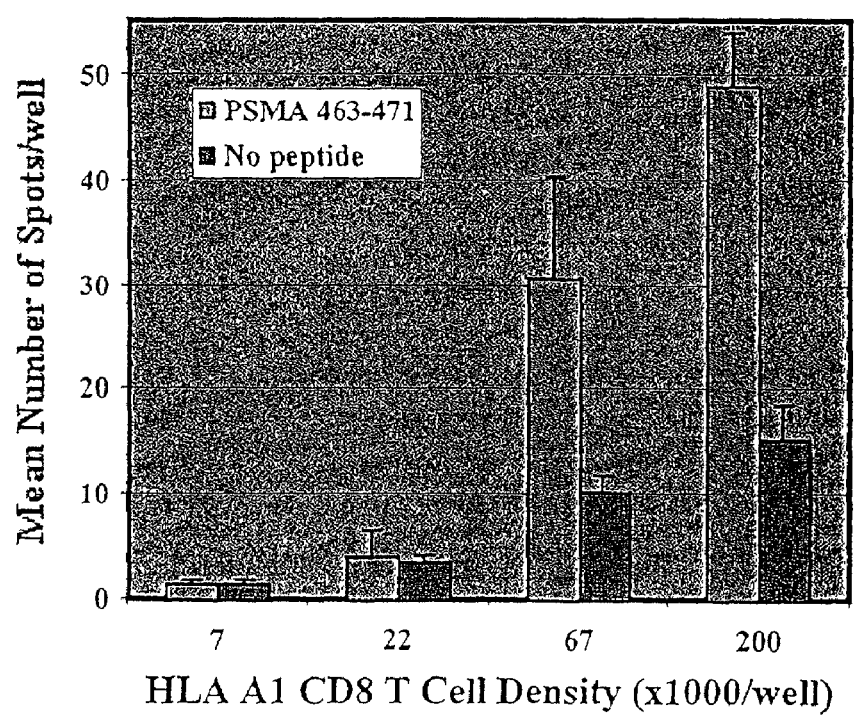
FIG. 5 shows the results of a γ (gamma)-IFN-based ELISPOT assay detecting $PSMA_{463-471}$-reactive $HLA-A1^{30}$ $CD8^{30}$ T cells.
Figure 6:
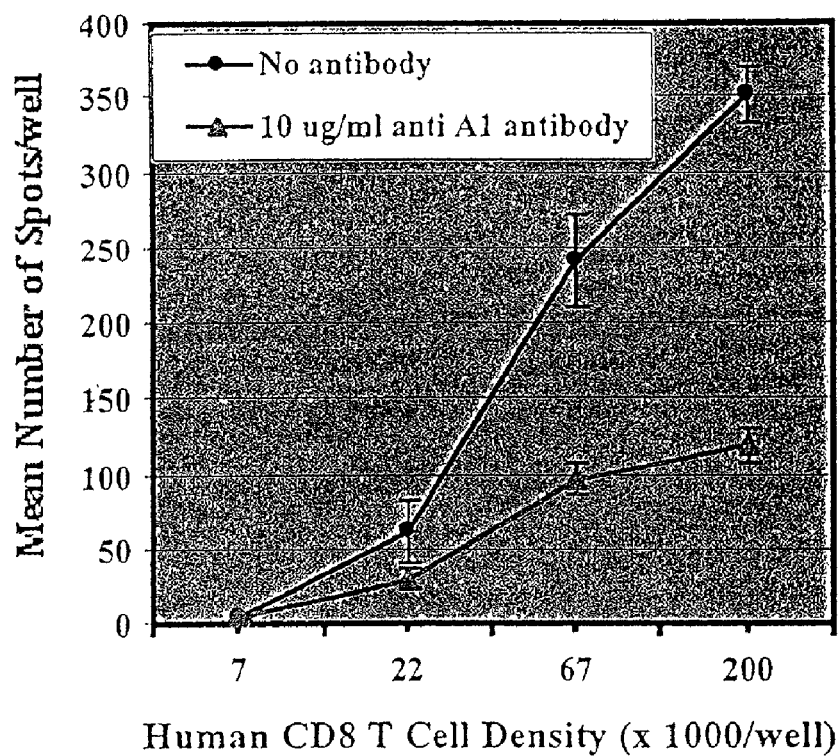
FIG. 6 shows blocking of reactivity of the T cells used in FIG. 10 by anti-HLA-A1 mAb, demonstrating HLA-A1-restricted recognition.

FIG. 5 shows the detection of $PSMA_{463-471}$ (SEQ ID NO. 35)-reactive HLA-A1$^+$ CD8$^+$ T cells previously generated in cultures of HLA-A1$^+$ CD8$^+$ T cells with autologous dendritic cells plus the peptide. No reactivity is detected from cultures without peptide (data not shown). In this case it can be seen that the peptide reactive T cells are present in the culture at a frequency between 1 in $2.2 \times 10^4$ and 1 in $6.7 \times 10^4$. That this is truly an HLA-A1-restricted response is demonstrated by the ability of anti-HLA-A1 monoclonal antibody to block –IFN production; see FIG. 6.

Example 1.4

Cluster Analysis ($PSMA_{653-687}$).

Another peptide, FDKSNPIVLRMMNDQLMFLERAFIDPLGLPDRPFY $PSMA_{653-687}$, (SEQ ID NO. 37) containing an A2 epitope cluster from prostate specific membrane antigen, $PSMA_{660-681}$ (SEQ ID NO. 38), was synthesized by MPS (purity>95%) and subjected to proteasome digestion and mass spectrum analysis as described above. Prominent peaks from the mass spectra are summarized in Table 7.

TABLE 7

$PSMA_{653-687}$ Mass Peak Identification.

| SEQ ID NO. | MS PEAK (measured) | PEPTIDE | SEQUENCE | CALCULATED MASS (MH$^+$) |
|---|---|---|---|---|
| 149 | 906.17 ± 0.65 | 681-687** | LPDRPFY | 908.05 |
| 150 | 1287.73 ± 0.76 | 677-687** | DPLGLPDRPFY | 1290.47 |
| 151 | 1400.3 ± 1.79 | 676-687 | IDPLGLPDRPFY | 1403.63 |
| 152 | 1548.0 ± 1.37 | 675-687 | FIDPLGLPDRPFY | 1550.80 |
| 153 | 1619.5 ± 1.51 | 674-687** | AFIDPLGLPDRPFY | 1621.88 |
| 154 | 1775.48 ± 1.32 | 673-687* | RAFIDPLGLPDRPFY | 1778.07 |
| 155 | 2440.2 ± 1.3 | 653-672 | FDKSNPIVLRMMNDQLMFLE | 2442.932313.82 |
| 156 | 1904.63 ± 1.56 | 672-687* | ERAFIDPLGLPDRPFY | 1907.19 |
| 157 | 2310.6 ± 2.5 | 653-671 | FDKSNPIVLRMMNDQLMFL | 2313.82 |
| 158 | 2017.4 ± 1.94 | 671-687 | LERAFIDPLGLPDRPFY | 2020.35 |
| 159 | 2197.43 ± 1.78 | 653-670 | FDKSNPIVLRMMNDQLMF | 2200.66 |

Boldface sequence correspond to peptides predicted to bind to MHC, see Table 7.
*On the basis of mass alone this peak could equally well be assigned to a peptide beginning at 654, however proteasonal removal of just the N-terminal amino acid is considered unlikely. If the issue were important it could be resolved by N-terminal sequencing.
**On the basis of mass alone these peaks could have been assigned to internal fragments, but given the overall pattern of digestion it was considered unlikely.

Epitope Identification

Fragments co-C-terminal with 8-10 amino acid long sequences predicted to bind HLA by the SYFPEITHI or NIH algorithms were chosen for further study. The digestion and prediction steps of the procedure can be usefully practiced in any order. Although the substrate peptide used in proteasomal digest described here was specifically designed to include predicted HLA-A2.1 binding sequences, the actual products of digestion can be checked after the fact for actual or predicted binding to other MHC molecules. Selected results are shown in Table 8.

TABLE 8

Predicted HLA binding by proteasomally generated fragments

| VII. SEQ ID NO | VIII. PEPTIDE | HLA | SYFPEITHI | NIH |
|---|---|---|---|---|
| 39 & (40) | (R)MMNDQLMFL | A*0201 | 24(23) | 1360 (722) |
|  |  | A*0205 | NP† | 71(42) |
|  |  | A26 | 15 | NP |
|  |  | B*2705 | 12 | 50 |
| 41 | RMMNDQLMF | B*2705 | 17 | 75 |

†No prediction

As seen in Table 8, N-terminal addition of authentic sequence to epitopes can generate still useful, even better epitopes, for the same or different MHC restriction elements. Note for example the pairing of (R)MMNDQLMFL (SEQ ID NOS. 39 and (40)) with HLA-A*02, where the 10-mer retains substantial predicted binding potential.

HLA-A*0201 Binding Assay

Figure 7:
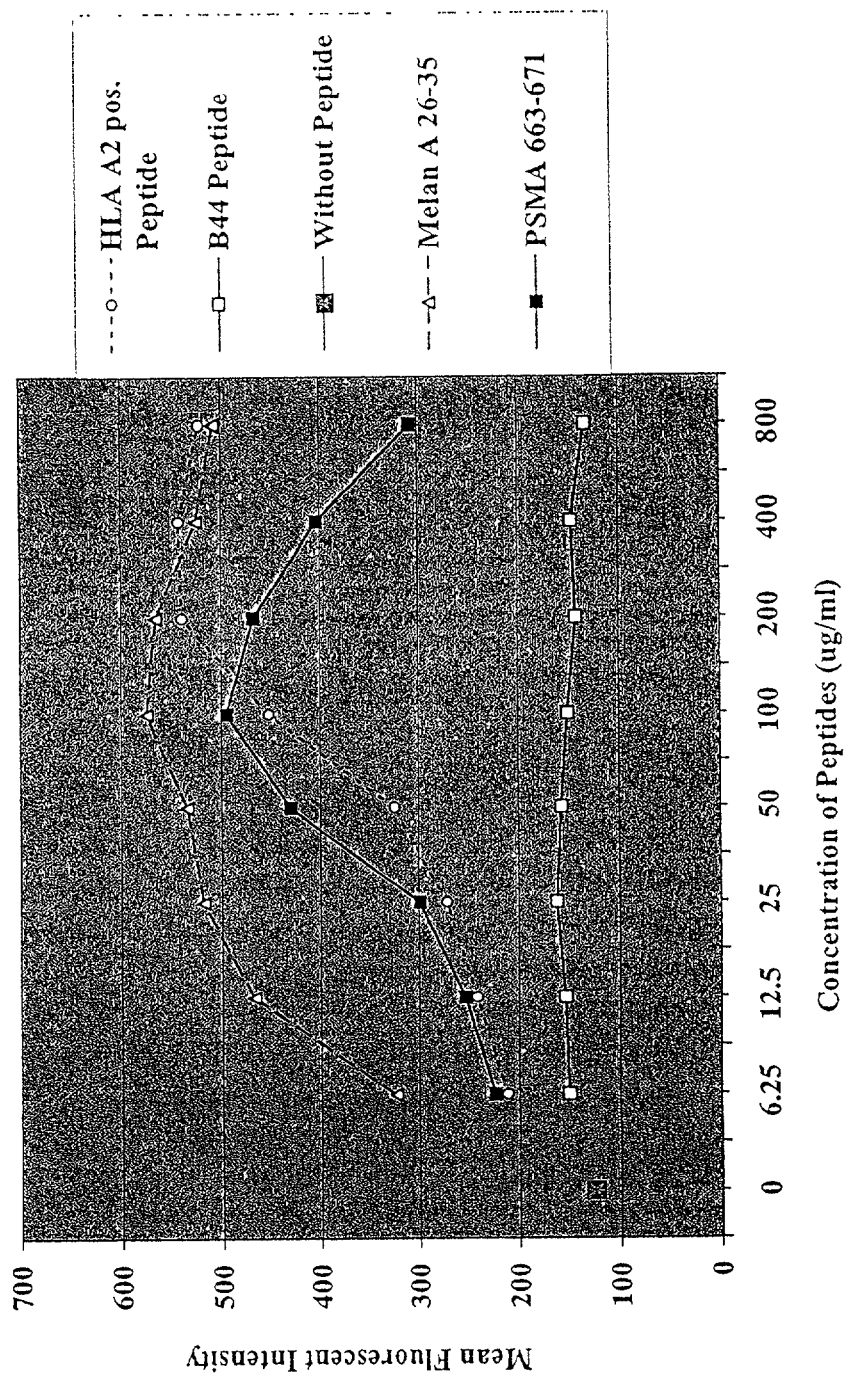
FIG. 7 shows a binding curve for HLA-A2:$PSMA_{663-671}$, with controls.
Figure 8:
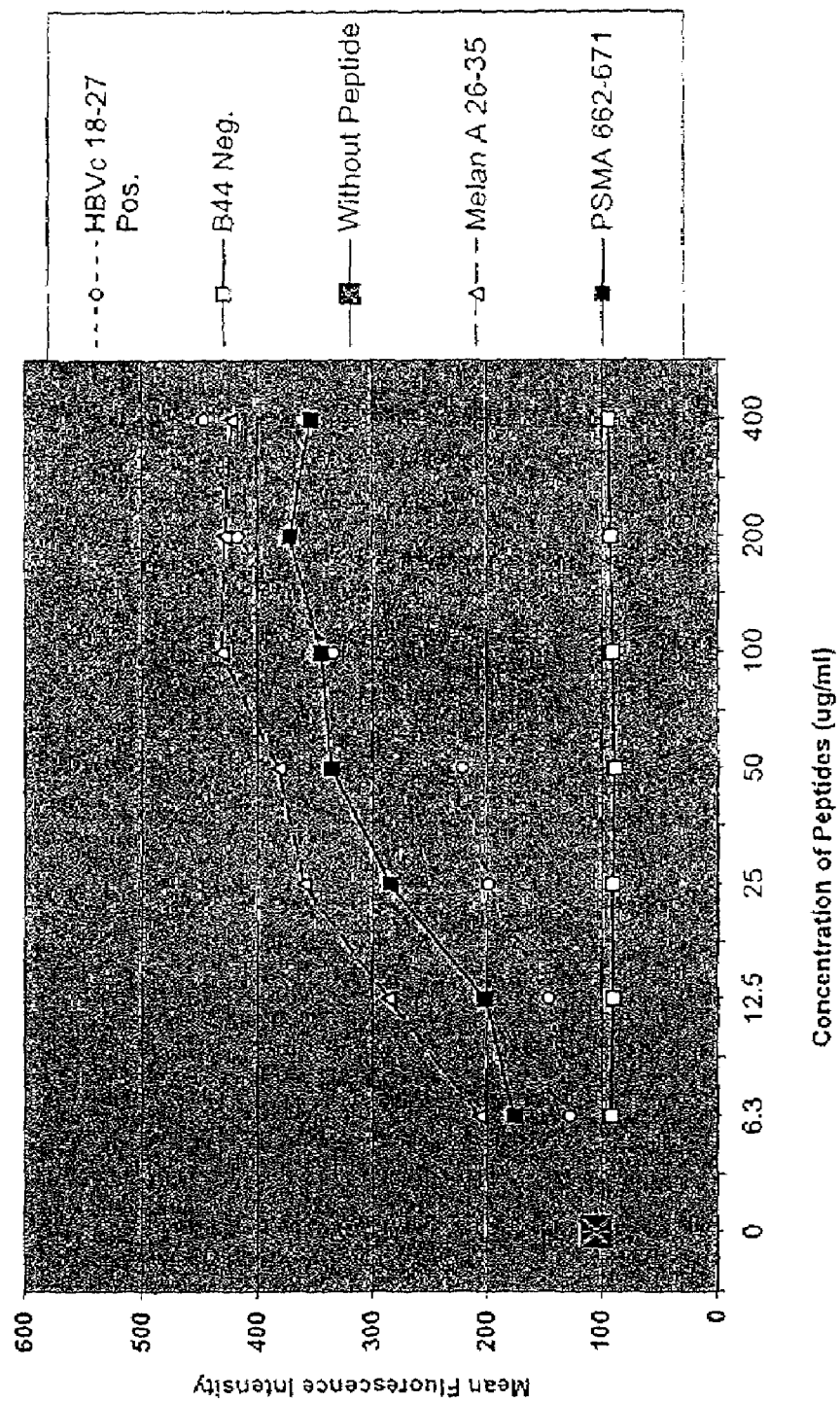
FIG. 8 shows a binding curve for HLA-A2:$PSMA_{662-671}$, with controls.

HLA-A*0201 binding studies were preformed, essentially as described in Example 1.1 above, with $PSMA_{663-671}$, (SEQ ID NO. 39) and $PSMA_{662-671}$, RMMNDQLMFL (SEQ NO. 67). As seen in FIGS. 4, 7 and 8, this epitope exhibits significant binding at even lower concentrations than the positive control peptide (FLPSDYFPSV ($HBV_{18-27}$); SEQ ID NO. 108). Though not run in parallel, comparison to the controls suggests that $PSMA_{662-671}$ (which approaches the Melan A peptide in affinity) has the superior binding activity of these two PSMA peptides.

Example 2

A multi-center clinical study is carried out using compositions as disclosed herein. The results of the study show the compositions to be useful and effective for debulking solid tumors and for generally inducing anti-angiogenic activity.

Example 3

Evaluation of a PSMA Composition in the Xenotransplanted Human Vasculature Model Generation of Target Antigen-Reactive CTL A. In Vivo Immunization of Mice.

HHD1 transgenic A*0201 mice (Pascolo, S., et al. *J. Exp. Med.* 185:2043-2051, 1997) were anesthetized and injected subcutaneously at the base of the tail, avoiding lateral tail veins, using 100 μl containing 100 nmol of $PSMA_{288-297}$ (SEQ ID NO. 21) and 20 μg of a HTL epitope peptide in PBS emulsified with 50 μl of IFA (incomplete Freund's adjuvant).

B. Preparation of Stimulating Cells (LPS Blasts).

Using spleens from 2 naïve mice for each group of immunized mice, un-immunized mice were sacrificed and their carcasses placed in alcohol. Using sterile instruments, the top dermal layer of skin on the mouse's left side (lower mid-section) was cut through, exposing the peritoneum. The peritoneum was saturated with alcohol, and the spleen aseptically extracted. The spleens were placed in a petri dish with serum-free media. Splenocytes were isolated by using sterile plungers from 3 ml syringes to mash the spleens. Cells were collected in a 50 ml conical tubes in serum-free media, rinsing dish well. Cells were centrifuged (12000 rpm, 7 min) and washed one time with RPMI. Fresh spleen cells were resuspended to a concentration of $1 \times 10^6$ cells per ml in RPMI-10% FCS (fetal calf serum). 25 g/ml lipopolysaccharide and 7 μg/ml Dextran Sulfate were added. Cell were incubated for 3 days in T-75 flasks at 37° C., with 5% $CO_2$. Splenic blasts were collected in 50 ml tubes pelleted (12,000 rpm, 7 min) and resuspended to $3 \times 10^7$/ml in RPMI. The blasts were pulsed with the priming peptide at 50 μg/ml, RT 4 hr. mitomycin C-treated at 25 μg/ml, 37° C., 20 min and washed three times with DMEM.

C. In vitro Stimulation.

Three days after LPS stimulation of the blast cells and the same day as peptide loading, the primed mice were sacrificed (at 14 days post immunization) to remove spleens as above. $3 \times 10^6$ splenocytes were co-cultured with $1 \times 10^6$ LPS blasts/well in 24-well plates at 37° C., with 5% $CO_2$ in DMEM media supplemented with 10% FCS, $5 \times 10^{-5}$ M β (beta)-mercaptoethanol, 100 μg/ml streptomycin and 100 IU/ml penicillin. Cultures were fed 5% (vol/vol) ConA supernatant on day 3 and can be transferred on day 7. An aliquot of the CTL are also tested in a standard chromium release assay to ensure activity.

Implantation and Adoptive Transfer $1 \times 10^6$ telomerase-transformed HDMEC in 10 μl of EGM-2-VM medium (Clonetics, San Diego, Calif.) are mixed with 0.5 ml of MATRIGEL (Becton Dickinson) on ice. The mixture is injected subcutaneously, through a 25 gauge needle, along the ventral midline of the thorax of SCID mice. One week later $1 \times 10^7$ T cells (target epitope-reactive or sham-immunized) in 0.2 ml are injected intravenously (alternatively they can be injected intraperitoneally).

Assessment (Micromorphometry)

At one and two weeks after transfer remove implants, fix in 10% buffered overnight, embed in paraffin, and section. For immunofluorescence detection of human microvessels using anti-human type IV collagen IgG and fluorescently-labeled secondary antibody, deparifinize and retrieve antigen by microwaving thin sections 2×7 minutes in 10 mM citric acid, pH 6.0. Vessel density is assessed as a function of the average number of positively stained annular structures observed in five separate, randomly selected 20× fields-of-view, from at least three sections per implant.

Example 4

A Fibronectin ED-B Vaccine in the HLA-transgenic Mouse Model

A. Establishment of Tumor

M1 tumor cells grown in complete RPMI plus 10% serum were harvested and washed with PBS by centrifugation. The cells were suspended in PBS at $5 \times 10^6$ cells/ml and 0.5 ml of the suspension (early passage) was injected subcutaneously into the abdomen.

B. Vaccination

A nucleotide sequence encoding an HLA-A2-restricted fibronectin ED-B domain-derived housekeeping epitope, for example ED-B$_{29-38}$ (SEQ ID NO. 103), is inserted into an appropriate vaccine vector (e.g. pVAX1 (Invitrogen Inc, Carlsbad, Calif.) or one of the vectors described in U.S. patent application Ser. No. 09/561,572 entitled "EXPRESSION VECTORS ENCODING EPITOPES OF TARGET-ASSOCIATED ANTIGENS," filed on Apr. 28, 2001, and incorporated by reference above. HHD-A2 mice are injected intranodally in the inguinal lymph node with 0, 2, 10, 50, 100, and 200 µg of vector in PBS every other day over 8 days (4 injections) alternating sides for each injection (single dosage per mouse or group of mice). Injection series are started the day of tumor cell injection, at 2 weeks before, and at 4 and 10 weeks after.

C. Evaluation

At approximately 12 weeks after injection of tumor cells visible tumors are observed in the mice receiving the vehicle instead of the vaccine. Effectiveness of the vaccine is expressed as the proportion of vaccinated animals that fail to develop a tumor in the same time frame, the relative size of tumors at the same time point, the delay in time before tumors appear in the vaccinated animals, and the dose and number of composition cycles needed to inhibit or prevent the establishment of tumor.

D. Alternative Schedule

The availability of more aggressive later passage M1 cells enables a more compressed experimental schedule. Instead mice are vaccinated on the day of tumor cell inoculation, 1 and 2 weeks before, and 3 or 4 days after injections of 1×10$^6$ cells. Effectiveness of vaccination is assessed at approximately 10 days after tumor cell inoculation.

Immunization with Peptide

HHD-A2 mice were immunized with ED-B29-38 (SEQ ID NO. 103) in complete Freund's adjuvants and spleen cells were harvested and re-stimulated in vitro using standard methodology. The resulting CTL were able to specifically lyse peptide pulsed T2 cells, which are HLA-A2+ (FIG. 9).

Example 5

Epitopes and Epitope Clusters

Table 9 discloses epitopes and epitope clusters from PSMA and ED-B that can be useful in construction of compositions according to the present invention.

TABLE 9

SEQ ID NOS.*

| SEQ ID NO | IDENTITY | SEQUENCE |
|---|---|---|
| 1 | PSMA protein | Accession number**: NP_004467 |
| 2 | PSMA cDNA | Accession number: NM_004476 |
| 3 | PSMA 163-192 | AFSPQGMPEGDLVYVNYARTEDFFKLERDM |
| 4 | PSMA 168-190 | GMPEGDLVYVNYARTEDFFKLER |
| 5 | PSMA 169-177 | MPEGDLVYV |
| 6 | PSMA 168-177 | GMPEGDLVYV |
| 7 | PSMA 168-176 | GMPEGDLVY |
| 8 | PSMA 167-176 | QGMPEGDLVY |
| 9 | PSMA 169-176 | MPEGDLVY |
| 10 | PSMA 171-179 | EGDLVYVNY |
| 11 | PSMA 170-179 | PEGDLVYVNY |
| 12 | PSMA 174-183 | LVYVNYARTE |
| 13 | PSMA 177-185 | VNYARTEDF |
| 14 | PSMA 176-185 | YVNYARTEDF |
| 15 | PSMA 178-186 | NYARTEDFF |
| 16 | PSMA 179-186 | YARTEDFF |
| 17 | PSMA 181-189 | RTEDFFKLE |
| 18 | PSMA 281-310 | RGIAEAVGLPSIPVHPIGYYDAQKLLEKMG |
| 19 | PSMA 283-307 | IAEAVGLPSIPVHPIGYYDAQKLLE |
| 20 | PSMA 289-297 | LPSIPVHPI |
| 21 | PSMA 288-297 | GLPSIPVIHPI |

TABLE 9-continued

SEQ ID NOS.*

| SEQ ID NO | IDENTITY | SEQUENCE |
|---|---|---|
| 22 | PSMA 297-305 | IGYYDAQKL |
| 23 | PSMA 296-305 | PIGYYDAQKL |
| 24 | PSMA 291-299 | SIPVHPIGY |
| 25 | PSMA 290-299 | PSIPVHPIGY |
| 26 | PSMA 292-299 | IPVHPIGY |
| 27 | PSMA 299-307 | YYDAQKLLE |
| 28 | PSMA 454-481 | SSIEGNYTLRVDCIPLMYSLVHLTKEL |
| 29 | PSMA 456-464 | IEGNYTLRV |
| 30 | PSMA 455-464 | SIEGNYTLRV |
| 31 | PSMA 457-464 | EGNYTLRV |
| 32 | PSMA 461-469 | TLRVDCTPL |
| 33 | PSMA 460-469 | YTLRVDCTPL |
| 34 | PSMA 462-470 | LRVDCTPLM |
| 35 | PSMA 463-471 | RVDCTPLMY |
| 36 | PSMA 462-471 | LRVDCTPLMY |
| 37 | PSMA 653-687 | FDKSNPIVLRMMNDQLMFLERAFIDPLGLPDRPFY |
| 38 | PSMA 660-681 | VLRMMNDQLMFLERAFIDPLGL |
| 39 | PSMA 663-671 | MMNDQLMFL |
| 40 | PSMA 662-671 | RMMNDQLMFL |
| 41 | PSMA 662-670 | RMMNDQLMF |
| 42 | PSMA 4-12 | LLHETDSAV |
| 43 | PSMA 13-21 | ATARRPRWL |
| 44 | PSMA 53-61 | TPKHNMKAF |
| 45 | PSMA 64-73 | ELKAENIKKF |
| 46 | PSMA 69-77 | NIKKFLH[1]NF |
| 47 | PSMA 68-77 | ENIKKFLH[1]NF |
| 48 | PSMA 220-228 | AGAKGVILY |
| 49 | PSMA 468-477 | PLMYSLVHNL |
| 50 | PSMA 469-477 | LMYSLVHNL |
| 51 | PSMA 463-471 | RVDCTPLMY |
| 52 | PSMA 465-473 | DCTPLMYSL |
| 53 | PSMA 507-515 | SGMPRISKL |
| 54 | PSMA 506-515 | FSGMPRISKL |
| 55 | PSMA 211-218 | GNKVKNAQ |
| 56 | PSMA 202-209 | IARYGKVF |
| 57 | PSMA 217-225 | AQLAGAKGV |
| 58 | PSMA 207-215 | KVFRGNKVK |

TABLE 9-continued

SEQ ID NOS.*

| SEQ ID NO | IDENTITY | SEQUENCE |
|---|---|---|
| 59 | PSMA 211-219 | GNKVKNAQL |
| 60 | PSMA 269-277 | TPGYPANEY |
| 61 | PSMA 268-277 | LTPGYPANEY |
| 62 | PSMA 271-279 | GYPANEYAY |
| 63 | PSMA 270-279 | PGYPANEYAY |
| 64 | PSMA 266-274 | DPLTPGYPA |
| 65 | PSMA 492-500 | SLYESWTKK |
| 66 | PSMA 491-500 | KSLYESWTKK |
| 67 | PSMA 486-494 | EGFEGKSLY |
| 68 | PSMA 485-494 | DEGFEGKSLY |
| 69 | PSMA 498-506 | TKKSPSPEF |
| 70 | PSMA 497-506 | WTKKSPSPEF |
| 71 | PSMA 492-501 | SLYESWTKKS |
| 72 | PSMA 725-732 | WGEVKRQI |
| 73 | PSMA 724-732 | AWGEVKRQI |
| 74 | PSMA 723-732 | KAWGEVKRQI |
| 75 | PSMA 723-730 | KAWGEVKR |
| 76 | PSMA 722-730 | SKAWGEVKR |
| 77 | PSMA 731-739 | QIYVAAFTV |
| 78 | PSMA 733-741 | YVAAFTVQA |
| 79 | PSMA 725-733 | WGEVKRQIY |
| 80 | PSMA 727-735 | EVKRQIYVA |
| 81 | PSMA 738-746 | TVQAAAETL |
| 82 | PSMA 737-746 | FTVQAAAETL |
| 83 | PSMA 729-737 | KRQIYVAAF |
| 84 | PSMA 721-729 | PSKAWGEVK |
| 85 | PSMA 723-731 | KAWGEVKRQ |
| 86 | PSMA 100-108 | WKEFGLDSV |
| 87 | PSMA 99-108 | QWKEFGLDSV |
| 88 | PSMA 102-111 | EFGLDSVELA |
| 89 | ED-B domain of Fibronectin | EVPQLTDLSFVDITDSSIGLRWTPLNSSTIIGYRI TVVAAGEGIPIFEDFVDSSVGYYTVTGLEPGID YDISVITLINGGESAPTTLTQQT |
| 90 | ED-B domain of Fibronectin with flanking sequence from Fribronectin | CTFDNLSPGLEYNVSVYTVKDDKESVPISDTIIP EVPQLTDLSFVDITDSSIGLRWTPLNSSTIIGYRI TVVAAGEGIPIFEDFVDSSVGYYTVTGLEPGID YDISVITLINGGESAPTTLTQQT AVPPPTDLRFTNIGPDTMRVTW |
| 91 | ED-B domain of Fibronectin cds | Accession number: X07717 |
| 92 | ED-B 4'-5 | TIIPEVPQL |

TABLE 9-continued

| SEQ ID NO | IDENTITY | SEQUENCE |
|---|---|---|
| 93 | ED-B 5'-5 | DTIIPEVPQL |
| 94 | ED-B 1-10 | EVPQLTDLSF |
| 95 | ED-B 23-30 | TPLNSSTI |
| 96 | ED-B 18-25 | IGLRWTPL |
| 97 | ED-B 17-25 | SIGLRWTPL |
| 98 | ED-B 25-33 | LNSSTIIGY |
| 99 | ED-B 24-33 | PLNSSTIIGY |
| 100 | ED-B 23-31 | TPLNSSTII |
| 101 | ED-B 31-38 | IGYRITVV |
| 102 | ED-B 30-38 | IIGYRITVV |
| 103 | ED-B 29-38 | TIIGYRITVV |
| 104 | ED-B 31-39 | IGYRITVVA |
| 105 | ED-B 30-39 | IIGYRITVVA |
| 106 | Melan-A 26-35$_{A>L}$ | ELAGIGILTV |
| 107 | Melan-A 26-35 | EAAGIGILTV |
| 108 | HBV 18-27 | FLPSDYFPSV |
| 109 | HLA-B44 binder | AEMGKYSFY |

[1]This H was reported as Y in the SWISSPROT database.
*Any of SEQ ID NOS. 5-17, 20-27, 29-36, 39-88, and 92-105 can be useful as epitopes in the various embodiments of the invention. Any of SEQ ID NOS. 3, 4, 18, 19, 28, 37, 38, 89 and 90 can be useful as sequences containing epitopes or epitope clusters, as described in various embodiments of the invention.
**All accession numbers used here and throughout can be accessed though the NCBI databases, for example, though the Entrez seek and retrieval system on the world wide web.

PSMA

| | | | | | |
|---|---|---|---|---|---|
| LOCUS | NM_004476 | 2653 bp | mRNA | PRI | 01-NOV-2000 |

DEFINITION  Homo sapiens folate hydrolase (prostate-specific membrane antigen)
            1 (FOLH1), mRNA.
ACCESSION   NM_004476
VERSION     NM_004476.1  GI:4758397
KEYWORDS    .
SOURCE      human.
  ORGANISM  Homo sapiens
            Eukaryota; Metazoa; Chordata; Craniata; Vertebrata; Euteleostomi;
            Mammalia; Eutheria; Primates; Catarrhini; Hominidae; Homo.
REFERENCE   1  (bases 1 to 2653)
  AUTHORS   Israeli,R.S., Powell,C.T., Fair,W.R. and Heston,W.D.
  TITLE     Molecular cloning of a complementary DNA encoding a
            prostate-specific membrane antigen
  JOURNAL   Cancer Res. 53 (2), 227-230 (1993)
  MEDLINE   93113576
REFERENCE   2  (bases 1 to 2653)
  AUTHORS   Rinker-Schaeffer CW, Hawkins AL, Su SL, Israeli RS, Griffin CA,
            Isaacs JT and Heston WD.
  TITLE     Localization and physical mapping of the prostate-specific membrane
            antigen (PSM) gene to human chromosome 11
  JOURNAL   Genomics 30 (1), 105-108 (1995)
  MEDLINE   96129312
   PUBMED   8595888
REFERENCE   3  (bases 1 to 2653)
  AUTHORS   O'Keefe DS, Su SL, Bacich DJ, Horiguchi Y, Luo Y, Powell CT,
            Zandvliet D, Russell PJ, Molloy PL, Nowak NJ, Shows TB, Mullins C,
            Vonder Haar RA, Fair WR and Heston WD.
  TITLE     Mapping, genomic organization and promoter analysis of the human
            prostate-specific membrane antigen gene
  JOURNAL   Biochim. Biophys. Acta 1443 (1-2), 113-127 (1998)
  MEDLINE   99057588
   PUBMED   9838072
REFERENCE   4  (bases 1 to 2653)
  AUTHORS   Maraj BH, Leek JP, Karayi M, Ali M, Lench NJ and Markham AF.
  TITLE     Detailed genetic mapping around a putative prostate-specific
            membrane antigen locus on human chromosome 11p11.2
  JOURNAL   Cytogenet. Cell Genet. 81 (1), 3-9 (1998)
  MEDLINE   98358137
   PUBMED   9691167
COMMENT     PROVISIONAL REFSEQ: This record has not yet been subject to final
            NCBI review. The reference sequence was derived from M99487.1.
FEATURES             Location/Qualifiers
     source          1..2653
                     /organism="Homo sapiens"
                     /db_xref="taxon:9606"
                     /chromosome="11"
                     /map="11p11.2"
                     /sex="male"

```
                        /cell_line="LNCaP-ATCC"
                        /cell_type="prostate"
                        /tissue_type="prostatic carcinoma metastatic
     lymph node"
                        /tissue_lib="LNCaP cDNA of Ron Israeli"
     gene               1..2653
                        /gene="FOLH1"
                        /note="FOLH; PSM; PSMA"
                        /db_xref="LocusID:2346"
                        /db_xref="MIM:600934"
     CDS                262..2514
                        /gene="FOLH1"
                        /note="folate hydrolase 1 (prostate-specific
     membrane
                        antigen)"
                        /codon_start=1
                        /db_xref="LocusID:2346"
                        /db_xref="MIM:600934"
                        /evidence=experimental
                        /product="folate hydrolase (prostate-specific
     membrane
                        antigen) 1"
                        /protein_id="NP_004467.1"
                        /db_xref="GI:4758398"
/translation="MWNLLHETDSAVATARRPRWLCAGALVLAGGFFLLGFLFGWFIK
SSNEATNITPKHNMKAFLDELKAENIKKFLYNFTQIPHLAGTEQNFQLAKQIQSQWKE
FGLDSVELAHYDVLLSYPNKTHPNYISIINEDGNEIFNTSLFEPPPPGYENVSDIVPP
FSAFSPQGMPEGDLVYVNYARTEDFFKLERDMKINCSGKIVIARYGKVFRGNKVKNAQ
LAGAKGVILYSDPADYFAPGVKSYPDGWNLPGGGVQRGNILNLNGAGDPLTPGYPANE
YAYRRGIAEAVGLPSIPVHPIGYYDAQKLLEKMGGSAPPDSSWRGSLKVPYNVGPGFT
GNFSTQKVKMHIHSTNEVTRIYNVIGTLRGAVEPDRYVILGGHRDSWVFGGIDPQSGA
AVVHEIVRSFGTLKKEGWRPRRTILFASWDAEEFGLLGSTEWAEENSRLLQERGVAYI
NADSSIEGNYTLRVDCTPLMYSLVHNLTKELKSPDEGFEGKSLYESWTKKSPSPEFSG
MPRISKLGSGNDFEVFFQRLGIASGRARYTKNWETNKFSGYPLYHSVYETYELVEKFY
DPMFKYHLTVAQVRGGMVFELANSIVLPFDCRDYAVVLRKYADKIYSISMKHPQEMKT
YSVSFDSLFSAVKNFTEIASKFSERLQDFDKSNPIVLRMMNDQLMFLERAFIDPLGLP
DRPFYRHVIYAPSSHNKYAGESFPGIYDALFDIESKVDPSKAWGEVKRQIYVAAFTVQ
AAAETLSEVA" (SEQ ID NO. 1)
     misc_feature    778..1029
                        /note="PA; Region: PA domain"
BASE COUNT        782 a      524 c      640 g      707 t
ORIGIN
        1 ctcaaaggg gccggatttc cttctcctgg aggcagatgt tgcctctctc
tctcgctcgg
       61 attggttcag tgcactctag aaacactgct gtggtggaga actggaccc
caggtctgga
      121 gcgaattcca gcctgcaggg ctgataagcg aggcattagt gagattgaga
gagactttac
      181 cccgccgtgg tggttggagg gcgcgcagta gagcagcagc acaggcgcgg
gtcccgggag
      241 gccggctctg ctcgcgccga gatgtggaat ctccttcacg aaaccgactc
ggctgtggcc
      301 accgcgcgcc gcccgcgctg gctgtgcgct ggggcgctgg tgctggcggg
tggcttcttt
      361 ctcctcggct ccctcttcgg gtggtttata aaatcctcca atgaagctac
taacattact
      421 ccaaagcata atatgaaagc ttttggat gaattgaaag ctgagaacat
caagaagttc
      481 ttatataatt ttacacagat accacattta gcaggaacag aacaaaactt
tcagcttgca
      541 aagcaaattc aatcccagtg gaaagaattt ggcctggatt ctgttgagct
agcacattat
```

```
  601 gatgtcctgt tgtcctaccc aaataagact catcccaact acatctcaat
aattaatgaa
  661 gatggaaatg agattttcaa cacatcatta tttgaaccac ctcctccagg
atatgaaaat
  721 gtttcggata ttgtaccacc tttcagtgct ttctctcctc aaggaatgcc
agagggcgat
  781 ctagtgtatg ttaactatgc acgaactgaa gacttcttta aattggaacg
ggacatgaaa
  841 atcaattgct ctgggaaaat tgtaattgcc agatatggga agttttcag
aggaaataag
  901 gttaaaaatg cccagctggc aggggccaaa ggagtcattc tctactccga
ccctgctgac
  961 tactttgctc ctggggtgaa gtcctatcca gatggttgga atcttcctgg
aggtggtgtc
 1021 cagcgtggaa atatcctaaa tctgaatggt gcaggagacc ctctcacacc
aggttaccca
 1081 gcaaatgaat atgcttatag gcgtggaatt gcagaggctg ttggtcttcc
aagtattcct
 1141 gttcatccaa ttggatacta tgatgcacag aagctcctag aaaaaatggg
tggctcagca
 1201 ccaccagata gcagctggag aggaagtctc aaagtgccct acaatgttgg
acctggcttt
 1261 actggaaact tttctacaca aaaagtcaag atgcacatcc actctaccaa
tgaagtgaca
 1321 agaatttaca atgtgatagg tactctcaga ggagcagtgg aaccagacag
atatgtcatt
 1381 ctggaggtc accgggactc atgggtgttt ggtggtattg accctcagag
tggagcagct
 1441 gttgttcatg aaattgtgag gagctttgga acactgaaaa aggaagggtg
gagacctaga
 1501 agaacaattt gtttgcaag ctgggatgca gaagaatttg gtcttcttgg
ttctactgag
 1561 tgggcagagg agaattcaag actccttcaa gagcgtggcg tggcttatat
taatgctgac
 1621 tcatctatag aaggaaacta cactctgaga gttgattgta caccgctgat
gtacagcttg
 1681 gtacacaacc taacaaaaga gctgaaaagc cctgatgaag ctttgaagg
caaatctctt
 1741 tatgaaagtt ggactaaaaa aagtccttcc ccagagttca gtggcatgcc
caggataagc
 1801 aaattgggat ctggaaatga ttttgaggtg ttcttccaac gacttggaat
tgcttcaggc
 1861 agagcacggt atactaaaaa ttgggaaaca aacaaattca gcggctatcc
actgtatcac
 1921 agtgtctatg aaacatatga gttggtggaa aagtttttatg atccaatgtt
taaatatcac
 1981 ctcactgtgg cccaggttcg aggagggatg gtgtttgagc tagccaattc
catagtgctc
 2041 cctttgatt gtcgagatta tgctgtagtt ttaagaaagt atgctgacaa
aatctacagt
 2101 atttctatga acatccaca ggaaatgaag acatacagtg tatcatttga
ttcactttt
 2161 tctgcagtaa agaattttac agaaattgct tccaagttca gtgagagact
ccaggacttt
 2221 gacaaaagca acccaatagt attaagaatg atgaatgatc aactcatgtt
tctggaaaga
 2281 gcatttattg atccattagg gttaccagac aggcctttt ataggcatgt
catctatgct
 2341 ccaagcagcc acaacaagta tgcaggggag tcattcccag gaatttatga
tgctctgttt
 2401 gatattgaaa gcaaagtgga cccttccaag gcctggggag aagtgaagag
acagatttat
```

2461 gttgcagcct tcacagtgca ggcagctgca gagactttga gtgaagtagc ctaagaggat
2521 tctttagaga atccgtattg aatttgtgtg gtatgtcact cagaaagaat cgtaatgggt
2581 atattgataa attttaaaat tggtatattt gaaataaagt tgaatattat atataaaaaa
2641 aaaaaaaaaa aaa (SEQ ID NO. 2)

ED-B domain of Fibronectin

LOCUS     HSFIBEDB     2823 bp   DNA   linear   PRI 09-AUG-1999

DEFINITION   Human fibronectin gene ED-B region.

ACCESSION   X07717

VERSION     X07717.1 GI:31406

KEYWORDS   alternate splicing; fibronectin.

SOURCE   human.

ORGANISM  Homo sapiens

Eukaryota; Metazoa; Chordata; Craniata; Vertebrata; Euteleostomi;

Mammalia; Eutheria; Primates; Catarrhini; Hominidae; Homo.

REFERENCE   1 (bases 1 to 2823)

AUTHORS   Paolella,G., Henchcliffe,C., Sebastio,G. and Baralle,F.E.

TITLE    Sequence analysis and *in vivo* expression show that alternative splicing of ED-B and ED-A regions of the human fibronectin gene are independent events JOURNAL   Nucleic Acids Res. 16 (8), 3545-3557 (1988)

MEDLINE   88233940

FEATURES          Location/Qualifiers source       1..2823

/organism="Homo sapiens"

/db_xref="taxon:9606"

/clone="MA10"

exon         1..104

/number=1

/product="fibronectin"

CDS         join(<2..104,1375..1647,2758..>2823)

/codon_start=1

/product="fibronectin"

/protein_id="CAB52437.1"

/db_xref="GI:5725425"

/translation="CTFDNLSPGLEYNVSVYTVKDDKESVPISDTIIPEVPQLTDLSF
VDITDSSIGLRWTPLNSSTIIGYRITVVAAGEGIPIFEDFVDSSVGYYTVTGLEPGID
YDISVITLINGGESAPTTLTQQTAVPPPTDLRFTNIGPDTMRVTW" (SEQ ID NO. 90)

| | | |
|---|---|---|
| intron | 105..1374 | |
| | /number=1 | |
| exon | 1375..1647 | |
| | /note="ED-B exon" | |
| | /number=2 | |
| | /product="fibronectin" | |
| intron | 1648..2757 | |
| | /number=2 | |
| exon | 2758..2823 | |
| | /number=3 | |
| | /product="fibronectin" | |

BASE COUNT     824 a     556 c     528 g     915 t
ORIGIN 1 ctgcactttt gataacctga gtcccggcct ggagtacaat gtcagtgttt acactgtcaa
   61 ggatgacaag gaaagtgtcc ctatctctga taccatcatc ccaggtaata gaaaataagc
  121 tgctatcctg agagtgacat tccaataaga gtggggatta gcatcttaat ccccagatgc
  181 ttaagggtgt caactatatt tgggatttaa ttccgatctc ccagctgcac tttccaaaac
  241 caagaagtca agcagcgat ttggacaaaa tgcttgctgt taacactgct ttactgtctg
  301 tgcttcactg ggatgctgtg tgttgcagcg agtatgtaat ggagtggcag ccatggcttt
  361 aactctgtat tgtctgctca catggaagta tgactaaaac actgtcacgt gtctgtactc
  421 agtactgata ggctcaaagt aatatggtaa atgcatccca tcagtacatt tctgcccgat
  481 tttacaatcc atatcaattt ccaacagctg cctatttcat cttgcagttt caaatccttc
  541 tttttgaaaa ttggattta aaaaaaagtt aagtaaaagt cacaccttca gggttgttct
  601 ttcttgtggc cttgaaagac aacattgcaa aggcctgtcc taaggatagg cttgtttgtc
  661 cattgggtta aacataatg aaagcattgg acagatcgtg tcccccttttg gactcttcag
  721 tagaatgctt ttactaacgc taattacatg ttttgattat gaatgaacct aaaatagtgg
  781 caatggcctt aacctaggcc tgtctttcct cagcctgaat gtgcttttga atggcacatt
  841 tcacaccata cattcataat gcattagcgt tatggccatg atgttgtcat gagttttgta
  901 tgggagaaaa aaaatcaatt tatcacccat ttattatttt ttccggttgt tcatgcaagc
  961 ttattttcta ctaaaacagt tttggaatta ttaaaagcat tgctgatact tacttcagat
 1021 attatgtcta ggctctaaga atggtttcga catcctaaac agccatatga tttttaggaa
 1081 tctgaacagt tcaaattgta cccttttaagg atgttttcaa aatgtaaaaa atatatatat
 1141 atatatatat tccctaaaag aatattcctg tttattcttc tagggaagca aactgttcat
 1201 gatgcttagg aagtcttttc agagaattta aaacagattg catattacca tcattgcttt 1261 aacattccac caattttact actagtaacc tgatatacac tgctttattt tttcctcttt 1321 ttttccctct attttccttt tgcctccccc tccctttgct ttgtaactca atagaggtgc 1381 cccaactcac tgacctaagc tttgttgata taaccgattc aagcatcggc ctgaggtgga 1441 ccccgctaaa ctcttccacc attattgggt accgcatcac agtagttgcg gcaggagaag 1501 gtatccctat ttttgaagat tttgtggact cctcagtagg atactacaca gtcacagggc 1561 tggagccggg cattgactat gatatcagcg ttatcactct cattaatggc ggcgagagtg 1621 cccctactac actgacacaa caaacgggtg aattttgaaa acttctgcgt ttgagacata 1681 gatggtgttg catgctgcca ccagttactc cggttaaata tggatgtttc atgggggaag 1741 tcagcaattg gccaaagatt cagataggtg gaattggggg gataaggaat caaatgcatc 1801 tgctaaactg attggagaaa aacacatgca atatcttcag tacactctca tttaaaccac 1861 aagtagatat aaagcctaga gaaatacaga tgtctgctct gttaaatata aaatagcaaa 1921 tgttcattca atttgaagac ctagaatttt tcttcttaaa taccaaacac gaataccaaa 1981 ttgcgtaagt accaattgat aagaatatat caccaaaatg taccatcatg ctcttccttc 2041 tacccttga taaactctac catgctcctt ctttgtagct aaaaacccat caaaatttag 2101 ggtagagtgg atgggcattg ttttgaggta ggagaaaagt aaacttggga ccattctagg 2161 ttttgttgct gtcactaggt aaagaaacac ctctttaacc acagtctggg gacaagcatg 2221 caacatttta aaggttctct gctgtgcatg ggaaaagaaa catgctgaga accaatttgc 2281 atgaacatgt tcacttgtaa gtagaattca ctgaatggaa ctgtagctct agatatctca 2341 catgggggga agtttaggac cctcttgtct ttttgtctgt gtgcatgtat ttctttgtaa 2401 agtactgcta tgtttctctt tgctgtgtgg caacttaagc ctcttcggcc tgggataaaa 2461 taatctgcag tggtattaat aatgtacata aagtcaacat atttgaaagt agattaaaat 2521 cttttttaaa tatatcaatg atggcaaaaa ggttaaaggg ggcctaacag tactgtgtgt 2581 agtgttttat ttttaacagt agtacactat aacttaaaat agacttagat tagactgttt 2641 gcatgattat gattctgttt cctttatgca tgaaatattg attttacctt tccagctact 2701 tcgttagctt taattttaaa atacattaac tgagtcttcc ttcttgttcg aaaccagctg 2761 ttcctcctcc cactgacctg cgattcacca acattggtcc agacaccatg cgtgtcacct 2821 ggg  (SEQ ID NO. 91)

//

What is claimed is:

1. A method of treating neoplastic disease comprising the step of immunizing a mammal to induce a cellular immune response directed against an antigen differentially expressed by tumor-associated neovasculature, wherein the immunization comprises delivering a therapeutic nucleic acid vaccine, comprising at least one immunogen corresponding to an antigen expressed by tumor-associated neovasculature to a mammal having a neoplastic disease, wherein said antigen is vascular endothelial growth factor receptor 2 (VEGFR2).

2. The method of claim 1, wherein the immunogen comprises a nucleic acid capable of conferring expression of at least a portion of said antigen.

3. The method of claim 1, further comprising the step of treating the mammal with an anti-tumor therapy active directly against cancerous cells.

4. The method of claim 3, wherein the anti-tumor therapy comprises immunization against a tumor-associated antigen.

5. The method of claim 1, wherein the cellular immune response comprises a CTL response.

6. The method of claim 1, further comprising the step of detecting the cellular immune response.

7. The method of claim 6, wherein the detecting step comprises detection of tumor growth inhibition, tumor size reduction, inhibition of tumor. metastasis, or increase in life expectancy of the mammal.

8. The method of claim 6, wherein the detecting step comprises an assay selected from the group consisting of a cytokine assay, a chromium release assay, an immunofluorescence assay, a cytotoxic T lymphocyte (CTL) assay, an Elispot assay, and observation of the health of the mammal.

9. A method of treating neoplastic disease comprising the step of immunizing a mammal to induce a cellular immune response directed against a first antigen differentially expressed by tumor-associated neovasculature and a second antigen associated with a tumor, wherein the immunization comprises delivering a therapeutic nucleic acid vaccine comprising at least a first immunogen corresponding to the first antigen and a second immunogen corresponding to the second antigen to a mammal having a neoplastic disease, wherein the first antigen is vascular endothelial growth factor receptor 2 (VEGFR2).

10. The method of claim 9, wherein the first immunogen comprises a nucleic acid capable of conferring expression of at least a portion of said antigen.

11. The method of claim 9, wherein the cellular immune response comprises a CTL response.

12. The method of claim 9, further comprising the step of detecting the cellular immune response.

13. The method of claim 12, wherein the detecting step comprises detection of tumor growth inhibition, tumor size reduction, inhibition of tumor metastasis, or increase in life expectancy of the mammal.

14. The method of claim 12, wherein the detecting step comprises an assay selected from the group consisting of a cytokine assay, a chromium release assay, an immunofluorescence assay, a cytotoxic T lymphocyte (CTL) assay, an Elispot assay, and observation of the health of the mammal.

15. A method of treating neoplastic disease comprising the step of immunizing a mammal to induce a cellular immune response directed against an antigen differentially expressed by tumor-associated neovasculature, wherein the immunization comprises delivering a therapeutic nucleic acid vaccine comprising a first immunogen comprising at least one housekeeping epitope and a second immunogen comprising at least one immune epitope to a mammal having a neoplastic disease, wherein the housekeeping and immune epitopes are derived from said antigen differentially expressed by tumor-associated neovasculature, wherein the antigen is vascular endothelial growth factor receptor 2 (VEGFR2).

16. The method of claim 15, wherein delivery of said first or second immunogen, or both, comprises delivery of a nucleic acid capable of conferring expression of at least a portion of said antigen.

17. The method of claim 15, further comprising the step of treating the mammal with an anti-tumor therapy active directly against cancerous cells.

18. The method of claim 17, wherein the anti-tumor therapy comprises immunization against a tumor-associated antigen.

19. The method of claim 15, wherein the cellular immune response comprises a CTL response.

20. The method of claim 15, further comprising the step of detecting the cellular immune response.

21. The method of claim 20, wherein the detecting step comprises detection of tumor growth inhibition, tumor size reduction, inhibition of tumor metastasis, or increase in life expectancy of the mammal.

22. The method of claim 20, wherein the detecting step comprises an assay selected from the group consisting of a cytokine assay, a chromium release assay, an immunofluorescence assay, a cytotoxic T lymphocyte (CTL) assay, an Elispot assay, and observation of the health of the mammal.

23. A method of treating neoplastic disease comprising the step of immunizing a mammal to induce a cellular immune response directed against an antigen differentially expressed by tumor-associated neovasculature, wherein the immunization comprises delivering a therapeutic nucleic acid vaccine comprising an immunogen comprising at least one housekeeping epitope derived from said antigen differentially expressed by tumor-associated neovasculature to a mammal having a neoplastic disease, wherein the antigen is vascular endothelial growth factor receptor 2 (VEGFR2).

24. The method of claim 23, wherein delivery of said immunogen comprises delivery of a nucleic acid capable of conferring expression of at least a portion of said antigen.

25. The method of claim 23, further comprising the step of treating the mammal with an anti-tumor therapy active directly against cancerous cells.

26. The method of claim 25, wherein the anti-tumor therapy comprises immunization against a tumor-associated antigen.

27. The method of claim 23, wherein the cellular immune response comprises a CTL response.

28. The method of claim 23, further comprising the step of detecting the cellular immune response.

29. The method of claim 28, wherein the detecting step comprises detection of tumor growth inhibition, tumor size reduction, inhibition of tumor metastasis, or increase in life expectancy of the mammal.

30. The method of claim 28, wherein the detecting step comprises an assay selected from the group consisting of a cytokine assay, a chromium release assay, an immunofluorescence assay, a cytotoxic T lymphocyte (CTL) assay, an Elispot assay, and observation of the health of the mammal.

31. The method of claim 15, wherein the first immunogen and the second immunogen are the same.

* * * * *